(12) United States Patent
Low et al.

(10) Patent No.: US 12,397,069 B2
(45) Date of Patent: *Aug. 26, 2025

(54) FIBROBLAST ACTIVATION PROTEIN (FAP)-TARGETED IMAGING AND THERAPY

(71) Applicant: PURDUE RESEARCH FOUNDATION, West Lafayette, IN (US)

(72) Inventors: Philip Stewart Low, West Lafayette, IN (US); Jyoti Roy, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 662 days.

This patent is subject to a terminal disclaimer.

(21) Appl. No.: 17/553,113

(22) Filed: Dec. 16, 2021

(65) Prior Publication Data

US 2022/0105208 A1   Apr. 7, 2022

Related U.S. Application Data

(63) Continuation of application No. 17/245,872, filed on Apr. 30, 2021, now Pat. No. 11,872,291, which is a continuation of application No. 16/469,907, filed as application No. PCT/US2017/065995 on Dec. 13, 2017, now abandoned.

(60) Provisional application No. 62/434,380, filed on Dec. 14, 2016, provisional application No. 62/575,050, filed on Oct. 20, 2017.

(51) Int. Cl.
  *A61K 51/04* (2006.01)
  *A61K 47/55* (2017.01)
  *A61K 49/00* (2006.01)
  *G01N 33/569* (2006.01)

(52) U.S. Cl.
  CPC .......... *A61K 51/0497* (2013.01); *A61K 47/55* (2017.08); *A61K 49/0032* (2013.01); *A61K 49/0043* (2013.01); *A61K 49/0052* (2013.01); *G01N 33/56966* (2013.01)

(58) Field of Classification Search
  CPC .................. A61K 47/55; A61K 51/04
  See application file for complete search history.

(56) References Cited

U.S. PATENT DOCUMENTS

| | | | |
|---|---|---|---|
| 7,998,997 | B2 | 8/2011 | Bachovchin et al. |
| 9,333,270 | B2 * | 5/2016 | Low ............... A61K 49/0032 |
| 11,872,291 | B2 * | 1/2024 | Low ............... A61K 49/0032 |
| 2003/0138432 | A1 | 7/2003 | Glazier |
| 2004/0033979 | A1 | 2/2004 | Dean et al. |
| 2006/0276435 | A1 | 12/2006 | Cohen et al. |
| 2008/0280856 | A1 | 11/2008 | Cohen et al. |
| 2011/0117025 | A1 | 5/2011 | Dacosta et al. |
| 2012/0021929 | A1 | 1/2012 | Karl et al. |
| 2014/0099340 | A1 | 4/2014 | June et al. |
| 2014/0271482 | A1 | 9/2014 | Low et al. |
| 2014/0357650 | A1 * | 12/2014 | Jansen ............... C07D 413/12 548/200 |
| 2015/0119330 | A1 | 4/2015 | McGee et al. |
| 2016/0296612 | A1 | 10/2016 | Ertl et al. |
| 2016/0303251 | A1 | 10/2016 | Vlahov et al. |
| 2017/0370937 | A1 | 12/2017 | Blume et al. |

FOREIGN PATENT DOCUMENTS

| | | |
|---|---|---|
| CN | 1303430 A | 7/2001 |
| CN | 103267852 | 2/2014 |
| CN | 105120903 A | 12/2015 |
| CN | 105949282 | 9/2016 |
| CN | 106046121 | 10/2016 |
| CN | 108152258 | 6/2018 |
| CN | 108333365 | 7/2018 |
| CN | 105407911 B | 5/2020 |
| CN | 111235221 | 6/2020 |
| CN | 111574634 | 8/2020 |
| CN | 110368496 | 12/2020 |
| EP | 1760076 | 3/2007 |
| EP | 3269740 | 1/2018 |
| WO | 1997034927 | 9/1997 |
| WO | 1998041631 | 9/1998 |
| WO | 1999047152 | 9/1999 |
| WO | 1999057151 A2 | 11/1999 |
| WO | 2000036420 | 6/2000 |
| WO | 2001068708 | 9/2001 |
| WO | 2006010517 | 2/2006 |
| WO | 2006042282 | 4/2006 |
| WO | 2006047635 | 5/2006 |
| WO | 2006125227 | 11/2006 |

(Continued)

OTHER PUBLICATIONS

PCT International Search Report for PCT/US2017/065995, completed Apr. 23, 2018.
Extended European Search Report for EP 17880889.5, completed Jul. 8, 2020.
Fischer, E., et al., "Radioimmunotherapy of Fibroblast Activation Protein Positive Tumors by Rapidly Internalizing Antibodies," 2012, Clinical Cancer Research, 18(22) pp. 6208-6218.
Ostermann, et al., "Effective Immunoconjugate Therapy in Cancer Models Targeting a Serine Protease of Tumor Fibroblasts," 2008, Clinical Cancer Research, 14(14) pp. 4584-4592.
Ruger, R., et al., . "In vivo near-infrared fluorescence imaging of FAP-expressing tumors with activatable FAP-targeted single-chain Fv-immunoliposomes," 2014, Journal of Controlled Release, 186(28) pp. 1-10.

(Continued)

*Primary Examiner* — Michael G. Hartley
*Assistant Examiner* — Jagadishwar R Samala
(74) *Attorney, Agent, or Firm* — Barnes & Thornburg LLP

(57) ABSTRACT

The present teachings relate generally to conjugates and methods for imaging a tumor microenvironment in a patient, and to conjugates and methods for imaging cancer-associated fibroblasts (CAFs) in the tumor microenvironment of a patient. The present teachings relate generally to method of making conjugates comprising a fibroblast activation protein (FAP) inhibitor.

22 Claims, 33 Drawing Sheets

(56) References Cited

FOREIGN PATENT DOCUMENTS

| WO | 2007085895 | | 8/2007 | |
| WO | 2007087131 | | 8/2007 | |
| WO | 2007111657 | | 10/2007 | |
| WO | 2007146104 | | 12/2007 | |
| WO | 2007149518 | | 12/2007 | |
| WO | 2008012693 | | 1/2008 | |
| WO | 2008028000 | | 3/2008 | |
| WO | 2008116053 | | 9/2008 | |
| WO | 2008116054 | | 9/2008 | |
| WO | 2009024542 | | 2/2009 | |
| WO | 2009026177 | | 2/2009 | |
| WO | 2009074275 | | 6/2009 | |
| WO | 2009139915 | | 11/2009 | |
| WO | 2010036814 | | 4/2010 | |
| WO | WO-2010036814 | A1 * | 4/2010 | .............. A61P 35/00 |
| WO | 2010083570 | | 7/2010 | |
| WO | 2011040972 | | 4/2011 | |
| WO | 2011040973 | A2 | 4/2011 | |
| WO | 2011158189 | | 12/2011 | |
| WO | 2012025633 | | 3/2012 | |
| WO | 2013033396 | | 3/2013 | |
| WO | 2013107820 | | 7/2013 | |
| WO | WO-2014001538 | A1 * | 1/2014 | ......... A61K 51/0478 |
| WO | 2014022636 | | 2/2014 | |
| WO | 2014072465 | | 5/2014 | |
| WO | 2014149069 | A1 | 9/2014 | |
| WO | 2014161845 | | 10/2014 | |
| WO | 2014167083 | | 10/2014 | |
| WO | 2014186301 | A1 | 11/2014 | |
| WO | 2015192124 | | 6/2015 | |
| WO | 2015114166 | | 8/2015 | |
| WO | 2015192123 | | 12/2015 | |
| WO | 2016055432 | | 4/2016 | |
| WO | 2016089879 | A1 | 6/2016 | |
| WO | 2016110598 | | 7/2016 | |
| WO | 2016146174 | | 9/2016 | |
| WO | 2016146639 | | 9/2016 | |
| WO | 2017165473 | | 9/2017 | |
| WO | 2017189569 | | 11/2017 | |
| WO | 2018111989 | | 6/2018 | |
| WO | 2018187418 | | 10/2018 | |
| WO | 2019083990 | | 5/2019 | |
| WO | 2019096261 | | 5/2019 | |
| WO | 2019118932 | | 6/2019 | |
| WO | 2019154859 | | 8/2019 | |
| WO | 2020081522 | | 4/2020 | |
| WO | 2020120979 | | 6/2020 | |
| WO | 2020142742 | | 7/2020 | |

OTHER PUBLICATIONS

Roy, J., "Small Molecule Targeted Imaging and Therapeutic Agent for Luteinizing Hormone Releasing Hormone Receptor and Fibroblast Activation Protein Alpha," 2017, A Dissertation Submitted to the Faculty of Purdue University in Partial fulfilment of the Requirements for the degree of Doctor of Philosophy, pp. 1-148.

Meletta, R., "Evaluation of the Radiolabeled Boronic Acid-Based FAP inhibitor MIP-1232 for Atherosclerotic Plaque Imaging," 2015, Molecules, 20(2) pp. 2081-2099.

Li, J., "An Activatable Near Infrared Fluorescent Probe for In Vivo Imaging of Fibroblast Activation Protein-alpha," 2012, Bioconjugate Chemistry, 23(8) pp. 1704-1711.

Brennen, W.N., "Targeting Carcinoma-Associated Fibroblasts Within the Tumor Stroma With a Fibroblast Activation Protein-Activated Prodrug," 2012, Journal of the National Cancer Institute, 104(17) pp. 1320-1334.

Dvorakova, P., et al., "Inhibitor-Decorated Polymer Conjugates Targeting Fibroblast Activation Protein," 2017, Journal of Medicinal Chemistry, 60(20) pp. 8385-8393.

Marquis, J., et al., "Targeting tumor microenvironment with radiolabeled inhibitors of seprase(FAP\#945;)," 2009, Proceedings of the American Association for Cancer Research, Abstract No. 4467.

Jammaz, A., et al., "Rapid and efficient synthesis of [18F]fluoronicotinamides, [18F]fluoroisonicotinamides and [18F]fluorobenzamides as potential pet radiopharmaceuticals for melanoma imaging," 2011, Journal of Labelled Compounds and Radiopharmaceuticals, 54(6) pp. 312-317.

Jansen, K., et al., "Selective Inhibitors of Fibroblast Activation Protein (FAP) with a (4-Quinolinoyl)-glycyl-2-cyanopyrrolidine Scaffold," 2013, ACS Medicinal Chemistry Letters, 4(5) pp. 491-496.

* cited by examiner

FIBROBLAST ACTIVATION PROTEIN (FAP)-TARGETED IMAGING AND THERAPY

CROSS REFERENCE TO RELATED APPLICATIONS

This application is a continuation application of U.S. application Ser. No. 17/245,873 filed Apr. 30, 2021, which is a continuation application of U.S. application Ser. No. 16/469,907 filed Jun. 14, 2019, which is a U.S. national stage application under 35 U.S.C. § 371 (b) of International Application No. PCT/US2017/065995 filed Dec. 13, 2017, which claims priority under 35 U.S.C. § 119 (e) to U.S. Provisional Application Ser. No. 62/434,380, filed Dec. 14, 2016 and U.S. Provisional Application Ser. No. 62/575,050, filed Oct. 20, 2017, in which both all of which are incorporated herein by reference in their entirety.

TECHNICAL FIELD

The present teachings relate generally to conjugates and methods for imaging a tumor microenvironment in a patient and, in some embodiments, to conjugates and methods for imaging cancer-associated fibroblasts (CAFs) in the tumor microenvironment of a patient. The present teachings also relate to conjugates and methods for therapeutically treating cancer cells and/or CAFs in a patient.

BACKGROUND

The tumor microenvironment plays an important role in the growth and development of the tumor. In addition to cancer cells, tumors include infiltrating immune and inflammatory cells such as T cells, tumor associated macrophages, myeloid-suppressor cells, cancer associated fibroblasts (CAF), blood and lymphatic vasculature networks, and extracellular matrix (ECM). Without the help of these cells, a tumor will fail to acquire immune-escaping, metastatic, and resistance properties.

CAFs are one of the major type of cells present in the tumor microenvironment and play a role in secretion of many chemokines, cytokines, growth factor, along with modification and degradation of ECM. CAFs overexpress fibroblast activation protein alpha (FAP) which has a limited expression on the healthy cells.

FAP is a type II membrane integral protein which belongs to a larger family of proteases which are capable of cleaving the proline-amino acid peptide bond. Other members of the same family are dipeptidyl peptidase IV (DPPIV) and proyloligopeptidase (POP). FAP exhibits both endo and exopeptidase activity. FAP is primarily found to be localized on the cell surface but a soluble form of the protein in human plasma has also been reported. FAP exists as a homodimer. FAP is found to be expressed in CAFs of more than 90% of the epithelial solid tumors, tissues involved in wound healing, and remodeling.

Efficient surgical removal of tumor mass has been improved by fluorescence guided surgery. However, NIR dye conjugates targeted to receptors/proteins overexpressed in cancer cells can image only the antigen positive cancer cells but not the stromal cells. Currently, there is no method available to efficiently image the tumor microenvironment. As such, there is no efficient way of imaging and surgically removing these cells.

SUMMARY

The scope of the present invention is defined solely by the appended claims, and is not affected to any degree by the statements within this summary.

Several embodiments of the invention are described in the following enumerated clauses:

1. A conjugate, or a pharmaceutically acceptable salt thereof, having a structure

B-L-X, wherein B comprises a fibroblast activation protein (FAP) inhibitor;
   L comprises a bivalent linker; and
   X comprises a near infrared (NIR) dye, a radioactive imaging agent, or a therapeutic agent effective against cancer cells and/or cancer-associated fibroblasts (CAF).

2. The conjugate of clause 1, wherein B has a structure

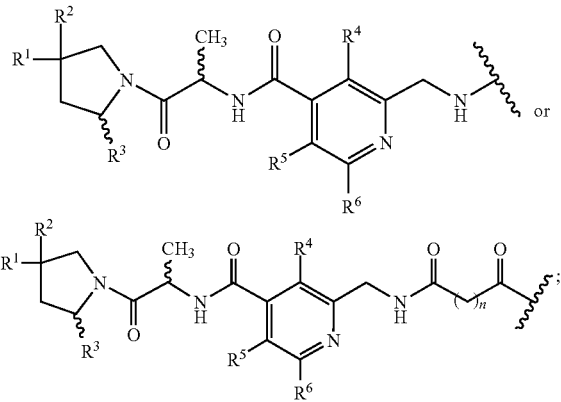

wherein $R^1$ and $R^2$ are the same or different, and are each independently selected from the group consisting of hydrogen, halogen, and $C_1$-$C_4$ alkyl;
   $R^3$ is a $C_1$-$C_4$ alkyl, nitrile, or isonitrile;
   $R^4$, $R^5$, and $R^6$ are the same or different, and are each independently selected from the group consisting of hydrogen, halogen, and $C_1$-$C_4$ alkyl; and
   n is an integer from 1 to 8.

3. The conjugate of clause 2, or a pharmaceutically acceptable salt thereof, wherein each of $R^1$ and $R^2$ is a halogen.

4. The conjugate of clause 2 or 3, or a pharmaceutically acceptable salt thereof, wherein each of $R^1$ and $R^2$ is fluorine.

5. The conjugate of any one of clauses 2 to 4, or a pharmaceutically acceptable salt thereof, wherein $R^3$ is nitrile.

6. The conjugate of any one of clauses 2 to 5, or a pharmaceutically acceptable salt thereof, wherein each of $R^4$, $R^5$, and $R^6$ is hydrogen.

7. The conjugate of any one of clauses 2 to 6, or a pharmaceutically acceptable salt thereof, wherein B has a structure

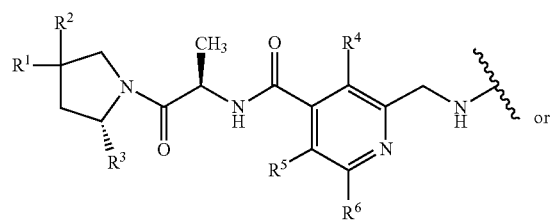

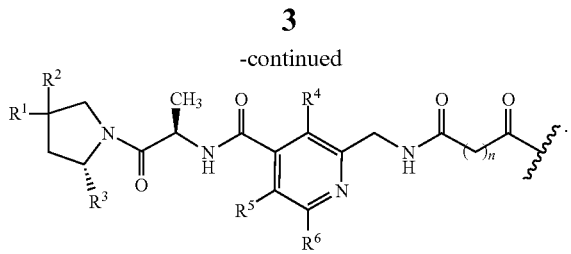

8. The conjugate of any one of clauses 2 to 7, or a pharmaceutically acceptable salt thereof, wherein B has a structure

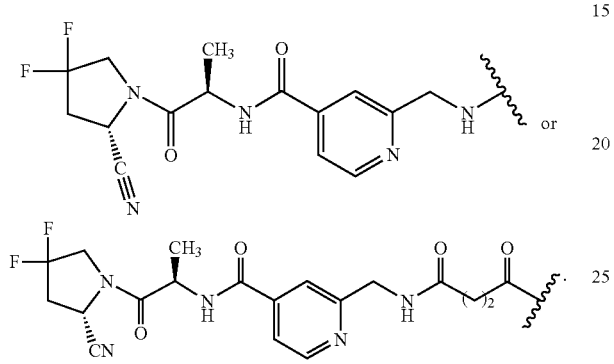

9. The conjugate of any one of the preceding clauses, or a pharmaceutically acceptable salt thereof, wherein the linker comprises at least one amino acid in the D- or L-configuration, or a derivative thereof, selected from the group consisting of Lys, Asn, Thr, Ser, Ile, Met, Pro, His, Gln, Arg, Gly, Asp, Glu, Ala, Val, Phe, Leu, Tyr, Cys, and Trp.

10. The conjugate of any one of the preceding clauses, or a pharmaceutically acceptable salt thereof, wherein the linker comprises at least two amino acids, or a derivative thereof, independently selected from the group consisting of Glu and Cys.

11. The conjugate of clause 9 or 10, or a pharmaceutically acceptable salt thereof, wherein the amino acid derivative is a glutamic acid having an amino sugar moiety covalently attached to the side chain carboxylic acid to form an amide bond.

12. The conjugate of clause 11, or a pharmaceutically acceptable salt thereof, wherein the amino sugar moiety is 1-deoxy-1-amino-D-glucitol.

13. The conjugate of clause 9 or 10, or a pharmaceutically acceptable salt thereof, wherein the linker comprises an amino acid portion of the formula Glu-Glu-Glu, wherein the glutamic acids are optionally substituted with an amino sugar moiety covalently attached to the side chain carboxylic acid to form an amide bond.

14. The conjugate of clause 14, or a pharmaceutically acceptable salt thereof, wherein the amino sugar moiety is 1-deoxy-1-amino-D-glucitol.

15. The conjugate of clauses 13 or 14, wherein the Glu-Glu-Glu are covalently bonded to each other through the carboxylic acid side chains.

16. The conjugate of any one of the preceding clauses, or a pharmaceutically acceptable salt thereof, wherein the linker comprises a moiety of the formula

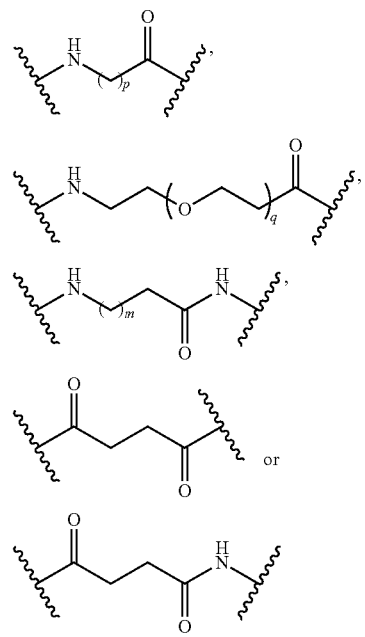

wherein m is an integer from 0 to 9, p is an integer from 3 to 10, q is an integer from 3 to 100.

17. The conjugate of any one of the preceding clauses, or a pharmaceutically acceptable salt thereof, wherein the linker comprises a portion selected from the group consisting of

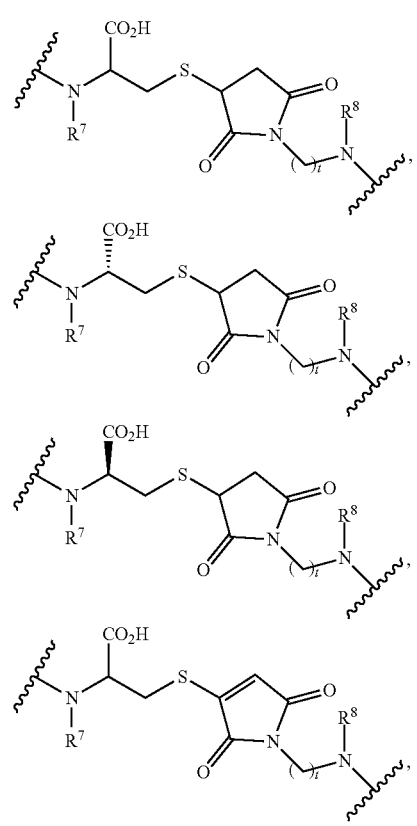

-continued

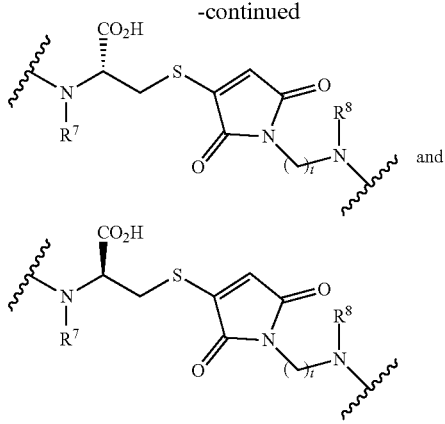

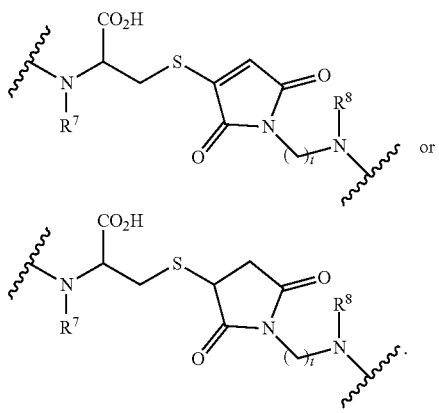

wherein
each of $R^7$ and $R^8$ is independently H or $C_1$-$C_6$ alkyl;
t is an integer from 1 to 8.

18. The conjugate of clause 17, or a pharmaceutically acceptable salt thereof, wherein the linker is of the formula 19. The conjugate of clause 17 or 18, or a pharmaceutically acceptable salt thereof, wherein $R^7$ and $R^8$ are H; and t is 2.

20. The conjugate of any one of the preceding clauses, or a pharmaceutically acceptable salt thereof, wherein the linker comprises a hydrazine 21. The conjugate of any one of the preceding clauses, or a pharmaceutically acceptable salt thereof, wherein L comprises a structure

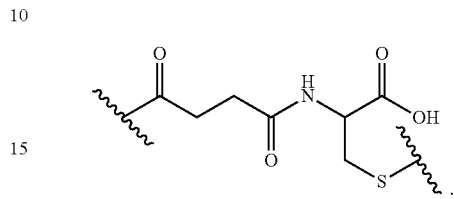

22. The conjugate of any one of the preceding clauses, or a pharmaceutically acceptable salt thereof, wherein the linker comprises a portion selected from the group consisting of

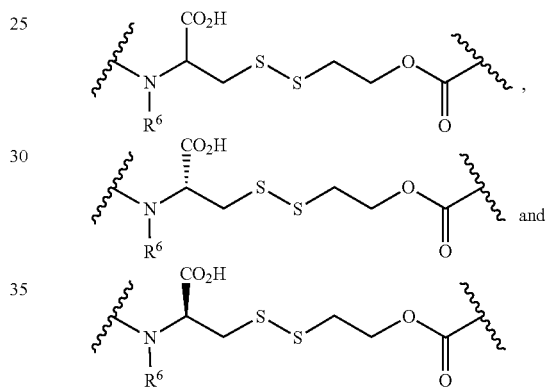

wherein $R^6$ is H or $C_1$-$C_6$ alkyl.

23. The conjugate of clause 1, or a pharmaceutically acceptable salt thereof, comprising the formula

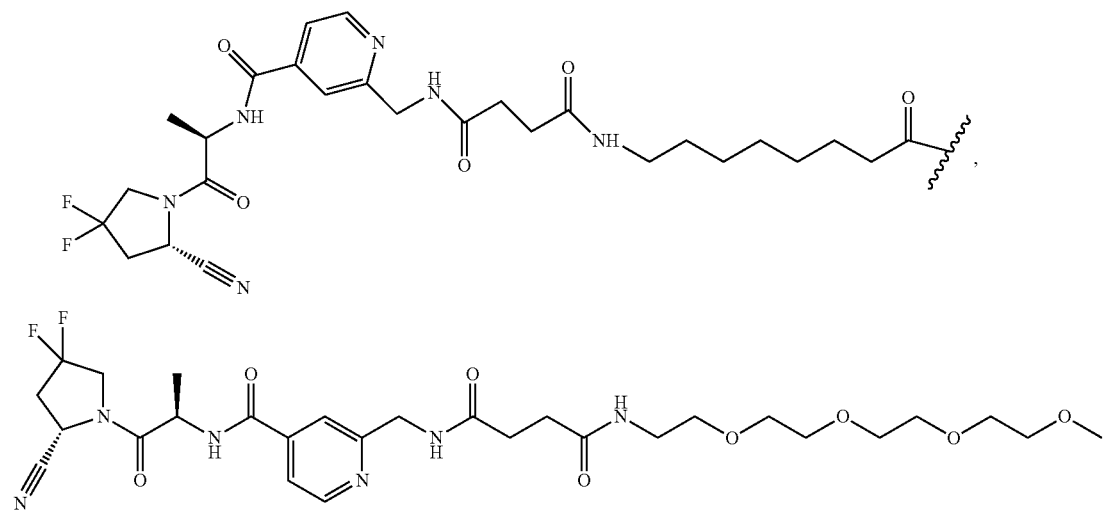

-continued

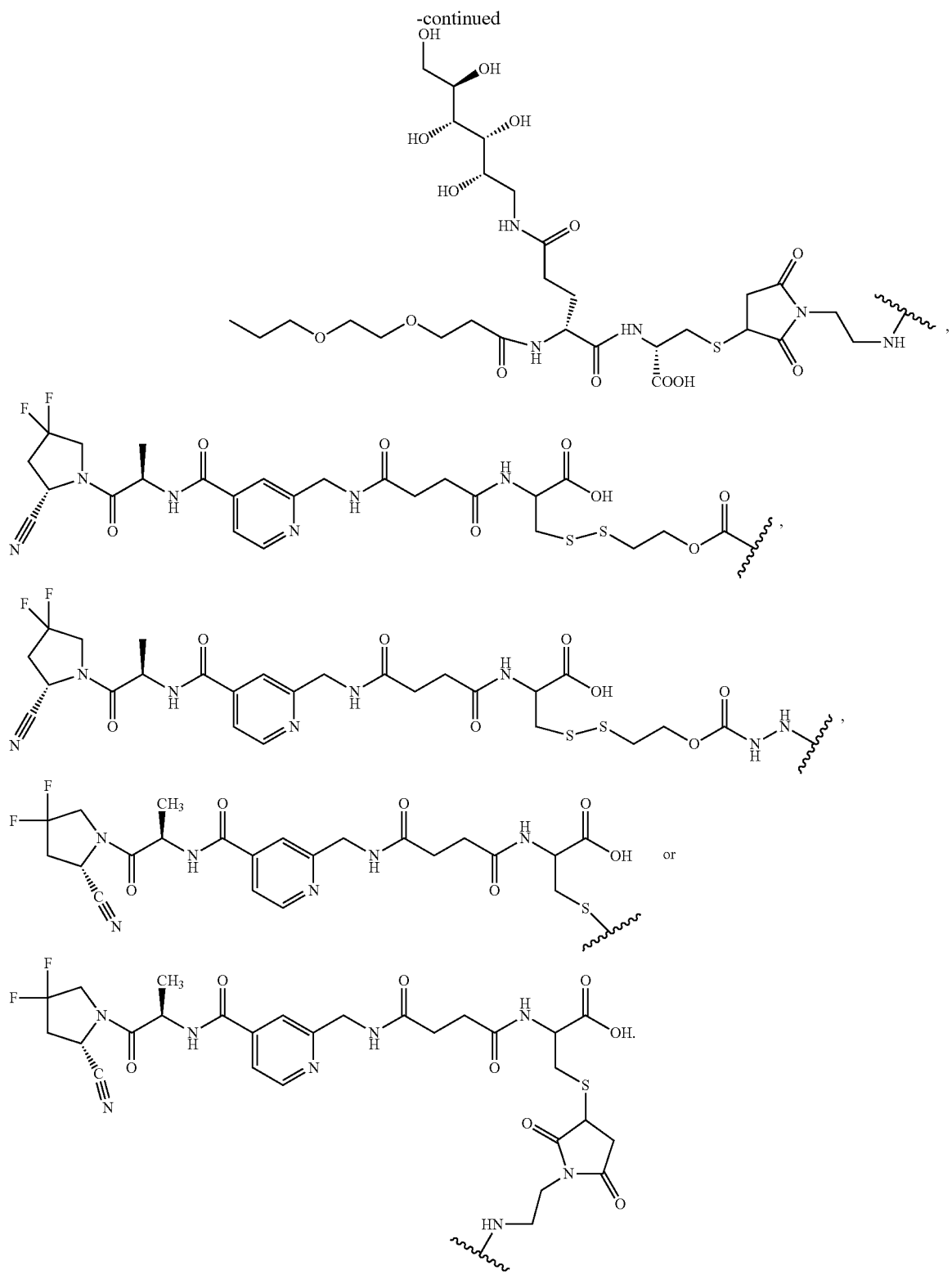

24. The conjugate of any one of the preceding clauses, or a pharmaceutically acceptable salt thereof, wherein X comprises a fluorescent dye.

25. The conjugate of any one of the preceding clauses, or a pharmaceutically acceptable salt thereof, wherein X comprises a NIR dye.

26. The conjugate of clause 24, or a pharmaceutically acceptable salt thereof, wherein the fluorescent dye is fluorescein maleimide or fluorescein isothiocyanate (FITC).

27. The conjugate of clause 25, or a pharmaceutically acceptable salt thereof, wherein the NIR dye is S0456.

28. The conjugate of any one of clauses 1 to 24 or 26, or a pharmaceutically acceptable salt thereof, clause 1 wherein X has a structure
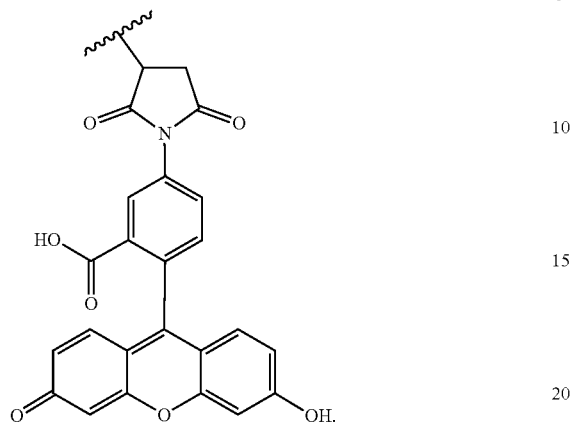
29. The conjugate of any one of clauses 1 to 23 or 25, or a pharmaceutically acceptable salt thereof, wherein X has a structure
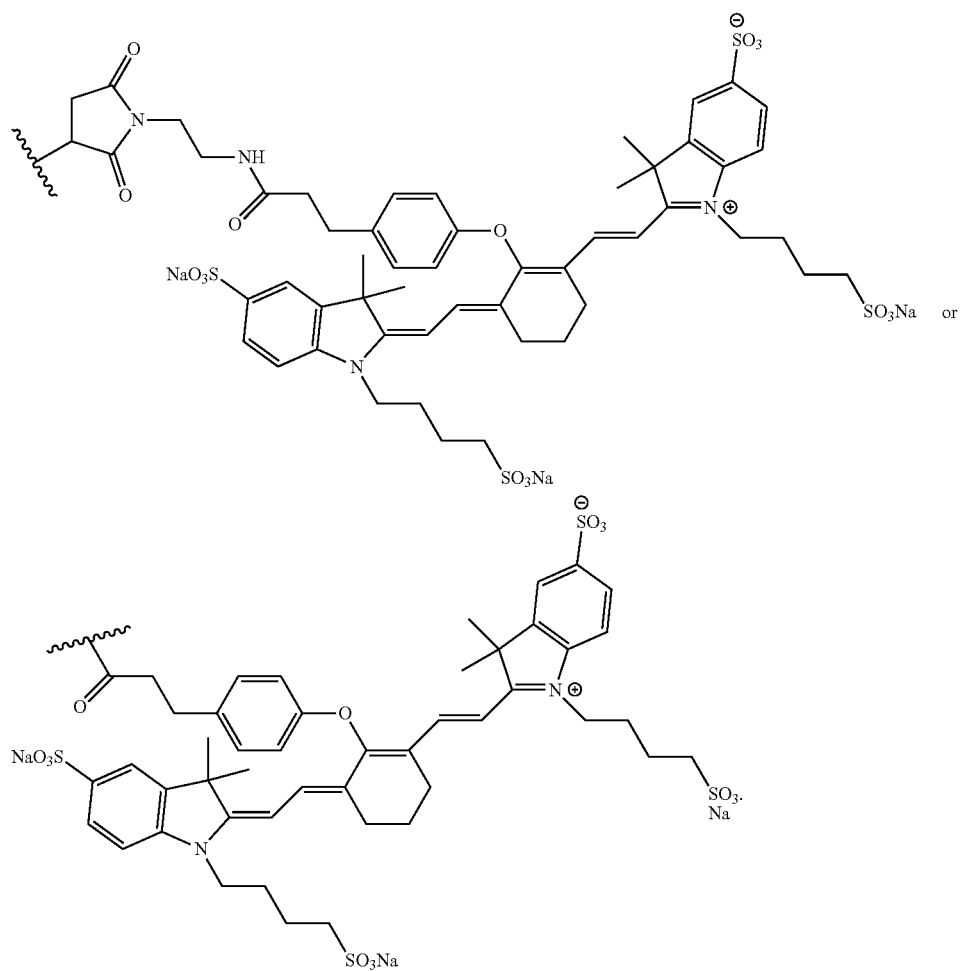

30. The conjugate of clause 1 having a structure
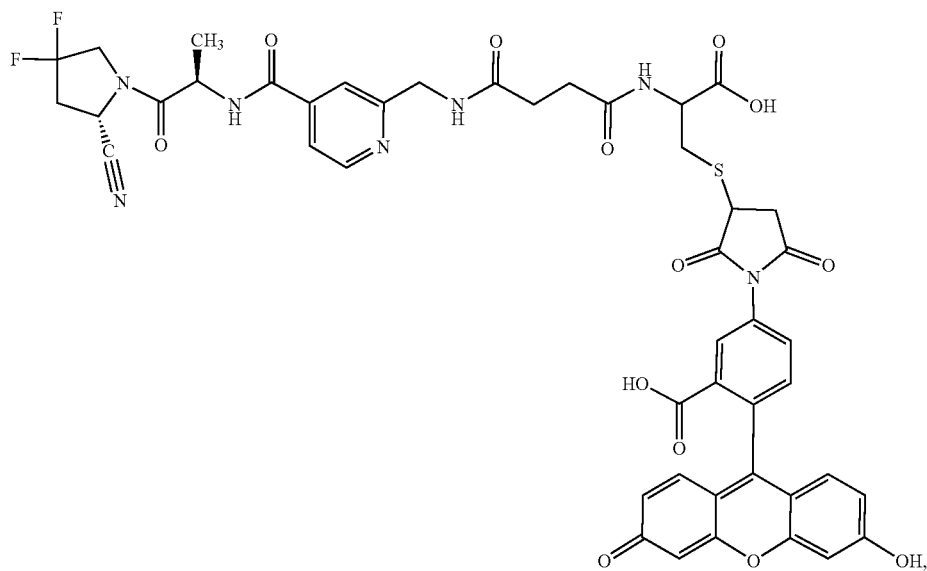 [SMILES: C[C@@H](NC(=O)c1ccnc(CNC(=O)CCC(=O)NC(CSC2CC(=O)N(c3ccc(-c4c5ccc(=O)cc-5oc5cc(O)ccc45)c(C(=O)O)c3)C2=O)C(=O)O)c1)C(=O)N1CC(F)(F)C[C@H]1C#N]
30
or a pharmaceutically acceptable salt thereof.
31. The conjugate of clause 1 having a structure
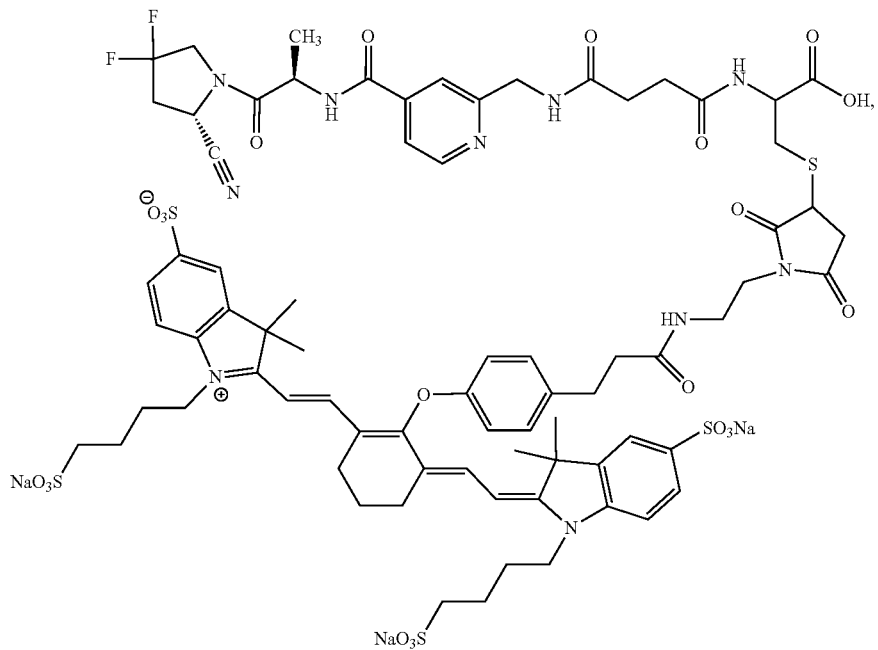
60
or a pharmaceutically acceptable salt thereof.
32. The conjugate of any one of clauses 1 to 23, or a pharmaceutically acceptable salt thereof, wherein X is a chelating agent of the formula

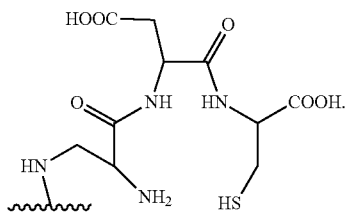 [SMILES: *NCC(N)C(=O)NC(CC(=O)O)C(=O)NC(CS)C(=O)O]

33. The conjugate of clause 32, or a pharmaceutically acceptable salt thereof, wherein X comprises a radioactive metal isotope coordinated to the chelating agent.

34. A conjugate having a structure

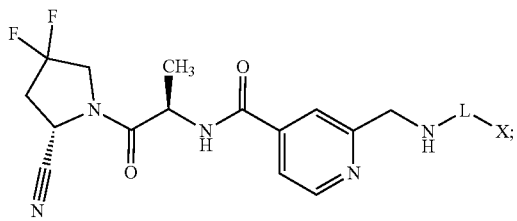

wherein L comprises a bivalent linker; and
X comprises a near infrared (NIR) dye.

35. The conjugate of clause 34 having a structure

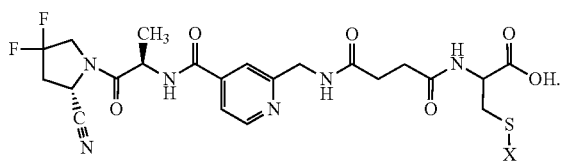

36. A method of surgically removing cancer-associated fibroblasts (CAFs) from a patient, the method comprising:
delivering a conjugate to a tumor microenvironment of the patient, the tumor microenvironment comprising at least one CAF, the conjugate having a structure

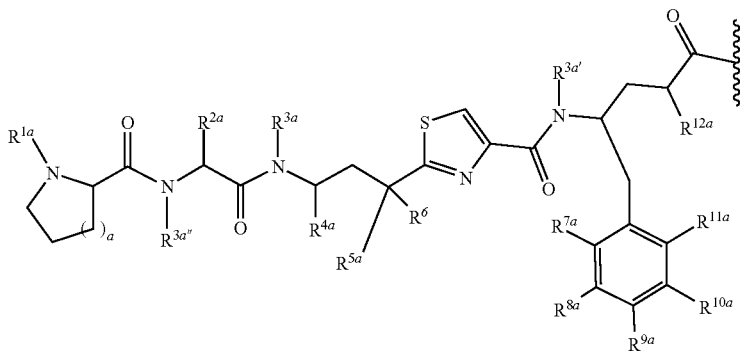

wherein L comprises a bivalent linker and X comprises a near infrared (NW) dye;
causing the NIR dye to fluoresce through an application of an optical stimulus thereto; and
cutting CAF-containing tissue of the patient based on a result of the fluorescence.

37. The method of clause 22 wherein the CAF-containing tissue imaged by the conjugate comprises stromal cells.

38. The conjugate of any one of clauses 1 to 23, or a pharmaceutically acceptable salt thereof, wherein A is a drug selected from the group consisting of a vinca alkaloid, a cryptophycin, bortezomib, thiobortezomib, a tubulysin, aminopterin, rapamycin, paclitaxel, docetaxel, doxorubicin, daunorubicin, everolimus, α-amanatin, verucarin, didemnin B, geldanomycin, purvalanol A, ispinesib, budesonide, dasatinib, an epothilone, a maytansine, and a tyrosine kinase inhibitor.

39. The conjugate of any one of clauses 1 to 23, or a pharmaceutically acceptable salt thereof, wherein the drug is a tubulysin.

40. The conjugate of any one of clauses 1 to 23, or a pharmaceutically acceptable salt thereof, wherein the drug is a tetrapeptide of the formula wherein
$R^{1a}$, $R^{3a}$, $R^{3a'}$ and $R^{3a''}$ are each independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{13a}$, —$OC(O)R^{13a}$, —$OC(O)NR^{13a}R^{13a'}$, —$OS(O)R^{13a}$, —$OS(O)_2R^{13a}$, —$SR^{13a}$, —$SC(O)R^{13a}$, —$S(O)R^{13a}$, —$S(O)_2R^{13a}$, —$S(O)_2OR^{13a}$, —$S(O)NR^{13a}R^{13a'}$, —$S(O)_2NR^{13a}R^{13a'}$, —$OS(O)NR^{13a}R^{13a'}$, —$NR^{13a}R^{13a'}$, —$NR^{13a}C(O)R^{14a}$, —$NR^{13a}C(O)OR^{14a}$, —$NR^{13a}C(O)NR^{14a}R^{14a'}$, —$NR^{13a}S(O)R^{14a}$, —$NR^{13a}S(O)_2R^{14a}$, —$NR^{13a}S(O)$ $NR^{13a}R^{14a'}$, $-NR^{13a}S(O)_2NR^{14a}R^{14a'}$, $-P(O)(OR^{13a})_2$, $-C(O)R^{13a}$, $-C(O)OR^{13a}$ or $-C(O)NR^{13a}R^{13a'}$;

$R^{2a}$, $R^{4a}$ and $R^{12a}$ are each independently selected from the group consisting of H, $C_1$-$C_6$ alkyl, $C_2$-$C_6$ alkenyl, $C_2$-$C_6$ alkynyl;

$R^{5a}$ and $R^{6a}$ are each independently selected from the group consisting of H, halogen, $C_1$-$C_6$ alkyl, $C_2$-$C_6$ alkenyl, $C_2$-$C_6$ alkynyl, $-OR^{15a}$, $-SR^{15a}$ and $-NR^{15a}R^{15a'}$, wherein each hydrogen atom in $C_1$-$C_6$ alkyl, $C_2$-$C_6$ alkenyl and $C_2$-$C_6$ alkynyl is independently optionally substituted by halogen, $-OR^{16a}$, $-SR^{16a}$, $-NR^{16a}R^{16a'}$, $-C(O)R^{16a}$, $-C(O)OR^{16a}$ or $-C(O)NR^{16a}R^{16a'}$; or $R^{5a}$ and $R^{6a}$ taken together with the carbon atom to which they are attached form a $-C(O)-$;

each $R^{7a}$, $R^{8a}$, $R^{9a}$, $R^{10a}$ and $R^{11a}$ is independently selected from the group consisting of H, halogen, $C_1$-$C_6$ alkyl, $C_2$-$C_6$ alkenyl, $C_2$-$C_6$ alkynyl, $-CN$, $-NO_2$, $-NCO$, $-OR^{17a}$, $-SR^{17a}$, $-S(O)_2OR^{17a}$, $-NR^{17a}R^{17a'}$, $-P(O)(OR^{17a})_2$, $-C(O)R^{17a}$, $-C(O)OR^{17a}$ and $-C(O)NR^{17a}R^{17a'}$, wherein each hydrogen atom in $C_1$-$C_6$ alkyl, $C_2$-$C_6$ alkenyl and $C_2$-$C_6$ alkynyl is independently optionally substituted by halogen, $-OR^{18a}$, $-SR^{18a}$, $-NR^{18a}R^{18a'}$, $-C(O)R^{18a}$, $-C(O)OR^{18a}$ or $-C(O)NR^{18a}R^{18a'}$;

each $R^{13a}$, $R^{13a'}$, $R^{14a}$, $R^{14a'}$, $R^{15a}$, $R^{15a'}$, $R^{16a}$, $R^{16a'}$, $R^{17a}$ and $R^{17a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, $-OH$, $-SH$, $-NH_2$ or $-CO_2H$;

each $R^{18a}$ and $R^{18a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl $-C(O)R^{19a}$, $-P(O)(OR^{19a})_2$, and $-S(O)_2OR^{19a}$, each $R^{19a}$ is independently selected from H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl; and a is 1, 2 or 3.

41. The conjugate of any one of clauses 1 to 23, or a pharmaceutically acceptable salt thereof, wherein D is a tetrapeptide of the formula

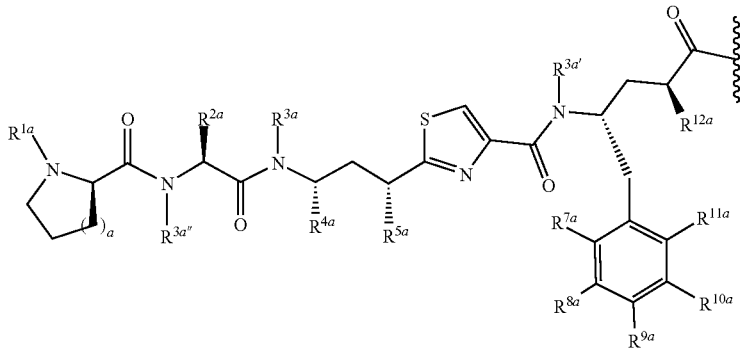

wherein $R^{1a}$, $R^{3a}$, $R^{3a'}$ and $R^{3a''}$ are each dependently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, $-OR^{13a}$, $-OC(O)R^{13a}$, $-OC(O)NR^{13a}R^{13a'}$, $-OS(O)R^{13a}$, $-OS(O)_2R^{13a}$, $-SR^{13a}$, $-SC(O)R^{13a}$, $-S(O)R^{13a}$, $-S(O)_2R^{13a}$, $-S(O)_2OR^{13a}$, $-S(O)NR^{13a}R^{13a'}$, $-S(O)_2NR^{13a}R^{13a'}$, $-OS(O)NR^{13a}R^{13a'}$, $-OS(O)_2NR^{13a}R^{13a'}$, $-NR^{13a}R^{13a'}$, $-NR^{13a}C(O)R^{14a}$, $-NR^{13a}C(O)OR^{14a}$, $-NR^{13a}C(O)NR^{14a}R^{14a'}$, $-NR^{13a}S(O)R^{14a}$, $-NR^{13a}S(O)_2R^{14a}$, $-NR^{13a}S(O)NR^{13a}R^{14a'}$, $-NR^{13a}S(O)_2NR^{14a}R^{14a'}$, $-P(O)(OR^{13a})_2$, $-C(O)R^{13a}$, $-C(O)OR^{13a}$ or $-C(O)NR^{13a}R^{13a'}$;

$R^{2a}$, $R^{4a}$ and $R^{12a}$ are each independently selected from the group consisting of H, $C_1$-$C_6$ alkyl, $C_2$-$C_6$ alkenyl, $C_2$-$C_6$ alkynyl;

$R^{5a}$ is selected from the group consisting of H, halogen, $C_1$-$C_6$ alkyl, $C_2$-$C_6$ alkenyl, $C_2$-$C_6$ alkynyl, $-OR^{15a}$, $-SR^{15a}$ and $-NR^{15a}R^{15a'}$, wherein each hydrogen atom in $C_1$-$C_6$ alkyl, $C_2$-$C_6$ alkenyl and $C_2$-$C_6$ alkynyl is independently optionally substituted by halogen, $-OR^{16a}$, $-SR^{16a}$, $-NR^{16a}R^{16a'}$, $-C(O)R^{16a}$, $-C(O)OR^{16a}$ or $-C(O)NR^{16a}R^{16a'}$;

each $R^{7a}$, $R^{8a}$, $R^{9a}$, $R^{10a}$ and $R^{11a}$ selected from the group consisting of H, halogen, $C_1$-$C_6$ alkyl, $C_2$-$C_6$ alkenyl, $C_2$-$C_6$ alkynyl, $-CN$, $-NO_2$, $-NCO$, $-OR^{17a}$, $-SR^{17a}$, $-S(O)_2OR^{17a}$, $-NR^{17a}R^{17a'}$, $-P(O)(OR^{17a})_2$, $-C(O)R^{17a}$, $-C(O)OR^{17a}$ and $-C(O)NR^{17a}R^{17a'}$, wherein each hydrogen atom in $C_1$-$C_6$ alkyl, $C_2$-$C_6$ alkenyl and $C_2$-$C_6$ alkynyl is independently optionally substituted by halogen, $-OR^{18a}$, $-SR^{18a}$, $-NR^{18a}R^{18a'}$, $-C(O)R^{18a}$, $-C(O)OR^{18a}$ or $-C(O)NR^{18a}R^{18a'}$;

each $R^{13}$, $R^{13a'}$, $R^{14a}$, $R^{14a'}$, $R^{15a}$, $R^{15a'}$, $R^{16a}$, $R^{16a'}$, $R^{17a}$ and $R^{17a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, —OH, —SH, —NH$_2$ or —CO$_2$H;

each $R^{18a}$ and $R^{18a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl —C(O)$R^{19a}$, —P(O)(O$R^{19a}$)$_2$, and —S(O)$_2$O$R^{19a}$, each $R^{19a}$ is independently selected from H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl; and a is 1, 2 or 3.

42. The conjugate of any one of clauses 1 to 23, or a pharmaceutically acceptable salt thereof, wherein D is a tetrapeptide of the formula

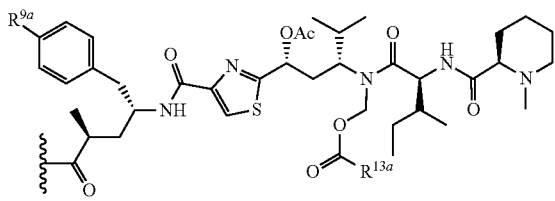

wherein $R^{9a}$ is selected from the group consisting of H, halogen, $C_1$-$C_6$ alkyl, $C_2$-$C_6$ alkenyl, $C_2$-$C_6$ alkynyl, —CN, —NO$_2$, —NCO, —O$R^{17a}$, —S$R^{17a}$, —S(O)$_2$O$R^{17a}$, —N$R^{17a}R^{17a'}$, —P(O)(O$R^{17a}$)$_2$, —C(O)$R^{17a}$, —C(O)O$R^{17a}$ and —C(O)N$R^{17a}$N$R^{17a'}$, wherein each hydrogen atom in $C_1$-$C_6$ alkyl, $C_2$-$C_6$ alkenyl and $C_2$-$C_6$ alkynyl is independently optionally substituted by halogen, —O$R^{18a}$, —S$R^{18a}$, —N$R^{18a}R^{18a'}$, —C(O)$R^{18a}$, —C(O)O$R^{18a}$ or —C(O)N$R^{18a}R^{18a'}$;

each $R^{13a}$, $R^{17a}$ and $R^{17a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, —OH, —SH, —NH$_2$ or —CO$_2$H;

each $R^{18a}$ and $R^{18a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl —C(O)$R^{19a}$, —P(O)(O$R^{19a}$)$_2$, and —S(O)$_2$O$R^{19a}$, each $R^{19a}$ is independently selected from H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl.

43. The conjugate of any one of clauses 1 to 23, or a pharmaceutically acceptable salt thereof, wherein A is a naturally occurring tubulysin.

44. The conjugate of any one of clauses 1 to 23, or a pharmaceutically acceptable salt thereof, wherein A is selected from the group consisting of tubulysin A, tubulysin B, tubulysin C, tubulysin D, tubulysin E, tubulysin F, tubulysin G, tubulysin H and tubulysin I.

45. The conjugate of any one of clauses 1 to 23, or a pharmaceutically acceptable salt thereof, wherein the drug is tubulysin B.

46. The conjugate of any one of clauses 1 to 23, or a pharmaceutically acceptable salt thereof, wherein A is of the formula

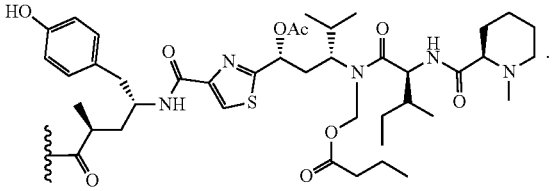 [SMILES: *C(=O)[C@@H](C)C[C@H](Cc1ccc(O)cc1)NC(=O)c1csc([C@@H](C[C@H](C(C)C)N(COC(=O)CCC)C(=O)[C@@H](NC(=O)[C@H]2CCCCN2C)C(C)CC)OC(C)=O)n1]

47. The conjugate of any one of the preceding clauses, or a pharmaceutically acceptable salt thereof, wherein A is of the formula

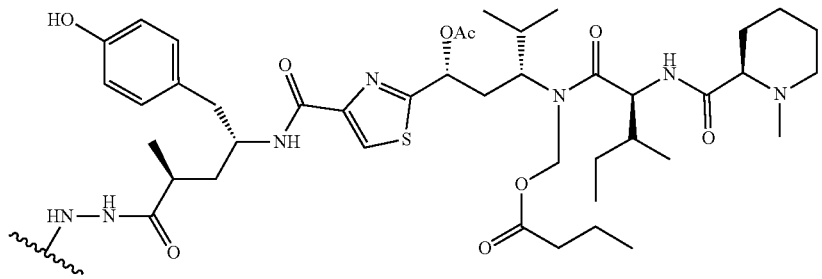 [SMILES: *NNC(=O)[C@@H](C)C[C@H](Cc1ccc(O)cc1)NC(=O)c1csc([C@@H](C[C@H](C(C)C)N(COC(=O)CCC)C(=O)[C@@H](NC(=O)[C@H]2CCCCN2C)C(C)CC)OC(C)=O)n1]

48. A conjugate of the formula

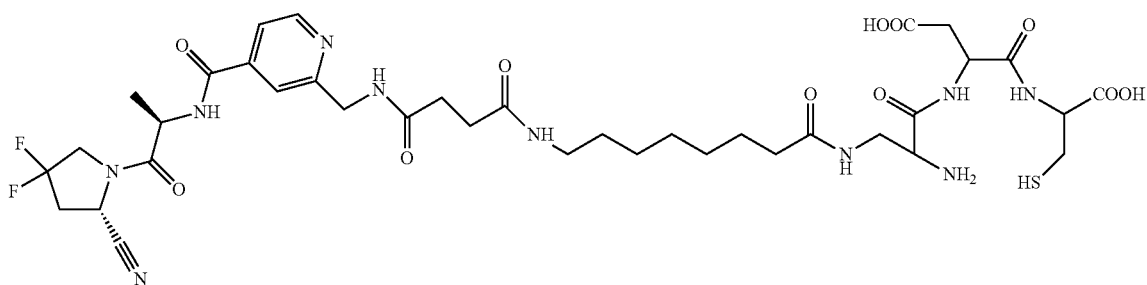 [SMILES: C[C@@H](NC(=O)c1ccnc(CNC(=O)CCC(=O)NCCCCCCCC(=O)NCC(N)C(=O)NC(CC(=O)O)C(=O)NC(CS)C(=O)O)c1)C(=O)N1CC(F)(F)C[C@H]1C#N]

or a pharmaceutically acceptable salt thereof.

49. The conjugate of clause 48, or a pharmaceutically acceptable salt thereof, wherein the conjugate comprises a radioactive metal isotope selected from the group consisting of $^{111}$In, $^{99m}$Tc, $^{64}$Cu, $^{67}$Cu, $^{67}$Ga and $^{68}$Ga coordinated thereto.

50. The conjugate of clause 49, wherein the radioactive metal isotope is $^{99m}$Tc.

51. A conjugate of the formula

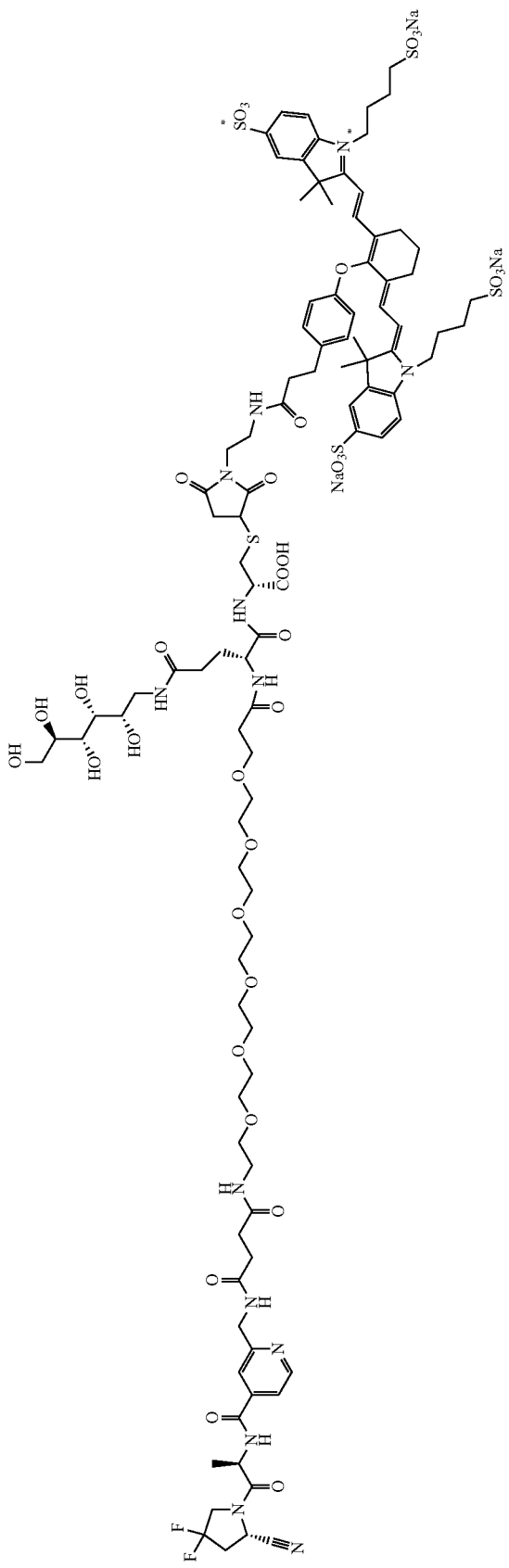

or a pharmaceutically acceptable salt thereof.

52. A conjugate of the formula

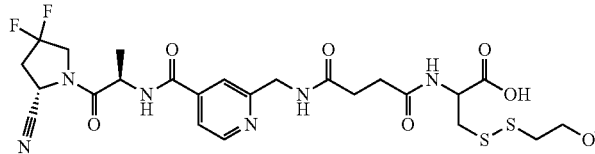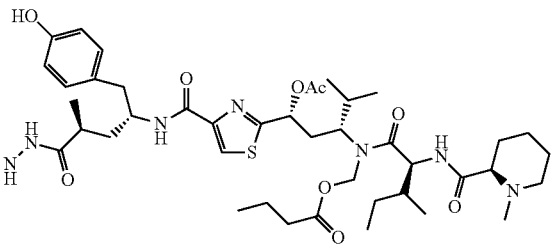

or a pharmaceutically acceptable salt thereof.

53. A pharmaceutical composition comprising a conjugate of any of the preceding clauses, or a pharmaceutically acceptable salt thereof, and optionally at least one pharmaceutically acceptable excipient.

54. A method of treating cancer in a subject, comprising,
   a. administering to the subject an effective amount of a conjugate or composition according to any one of clauses 1 to 23, 38 to 47 or 51; or a pharmaceutically acceptable salt thereof.

55. The method of clause 54, wherein the subject has a FAP expressing cancer.

56. The method of clause 54 or 55, wherein FAP expressing cancer is primary or metastatic.

57. The method of any one of clauses 44 to 56, wherein the cancer is selected from the group consisting of prostate, endometrial, skin, pancreatic, breast, kidney, ovarian and brain cancer.

58. A conjugate according to any one of clause 1 to 23, 38 to 47 or 51, or a pharmaceutically acceptable salt thereof, for use in a method of treating FAP expressing cancer in a subject.

59. The conjugate of clause 58, wherein the method comprises administering to the subject an amount of the conjugate effective for treating the FAP expressing cancer.

60. The conjugate of clause 58 or 59, wherein the FAP expressing cancer is selected from the group consisting of prostate, endometrial. skin, pancreatic, breast, kidney, ovarian and brain cancer.

61. Use of a conjugate according to any one of clauses 1 to 23, 38 to 47 or 51, or a pharmaceutically acceptable salt thereof, in the preparation of a medicament useful for treating FAP expressing cancer in a subject.

62. The use of clause 61, wherein the FAP expressing cancer is selected from the group consisting of prostate, endometrial, skin, pancreatic, breast, kidney, ovarian and brain cancer.

63. A method of imaging a population of cells in vitro, comprising
   a. contacting the cells with a conjugate according to any one of clauses 1 to 31, to provide labelled cells, and
   b. visualizing the labelled cells.

64. A conjugate according to any one of clauses 1 to 31, for use in a method of imaging a population of cells in vitro.

65. The conjugate of clause 63, wherein the method comprises
   a. contacting the cells with a conjugate according to any one of clauses 1 to 31, to provide labelled cells, and
   b. visualizing the labelled cells.

66. A method of imaging a population of cells in vivo, comprising
   a. administering to a patient an effective amount of a conjugate according to any one of clauses 1 to 23, 32, 33, 48 or 49, or a pharmaceutically acceptable salt thereof, to provide labelled cells; and
   b. visualizing the labelled cells by imaging.

67. A conjugate according to any one of clauses 1 to 23, 32, 33, 48 or 49, for use in a method of imaging a population of cells in vitro.

68. The conjugate of clause 67, wherein the method comprises
   a. administering to a patient an effective amount of a conjugate according to any one of clauses 1 to 23, 32, 33, 48 or 49, or a pharmaceutically acceptable salt thereof, to provide labelled cells; and
   b. visualizing the labelled cells by imaging.

DETAILED DESCRIPTION

Figure 1:
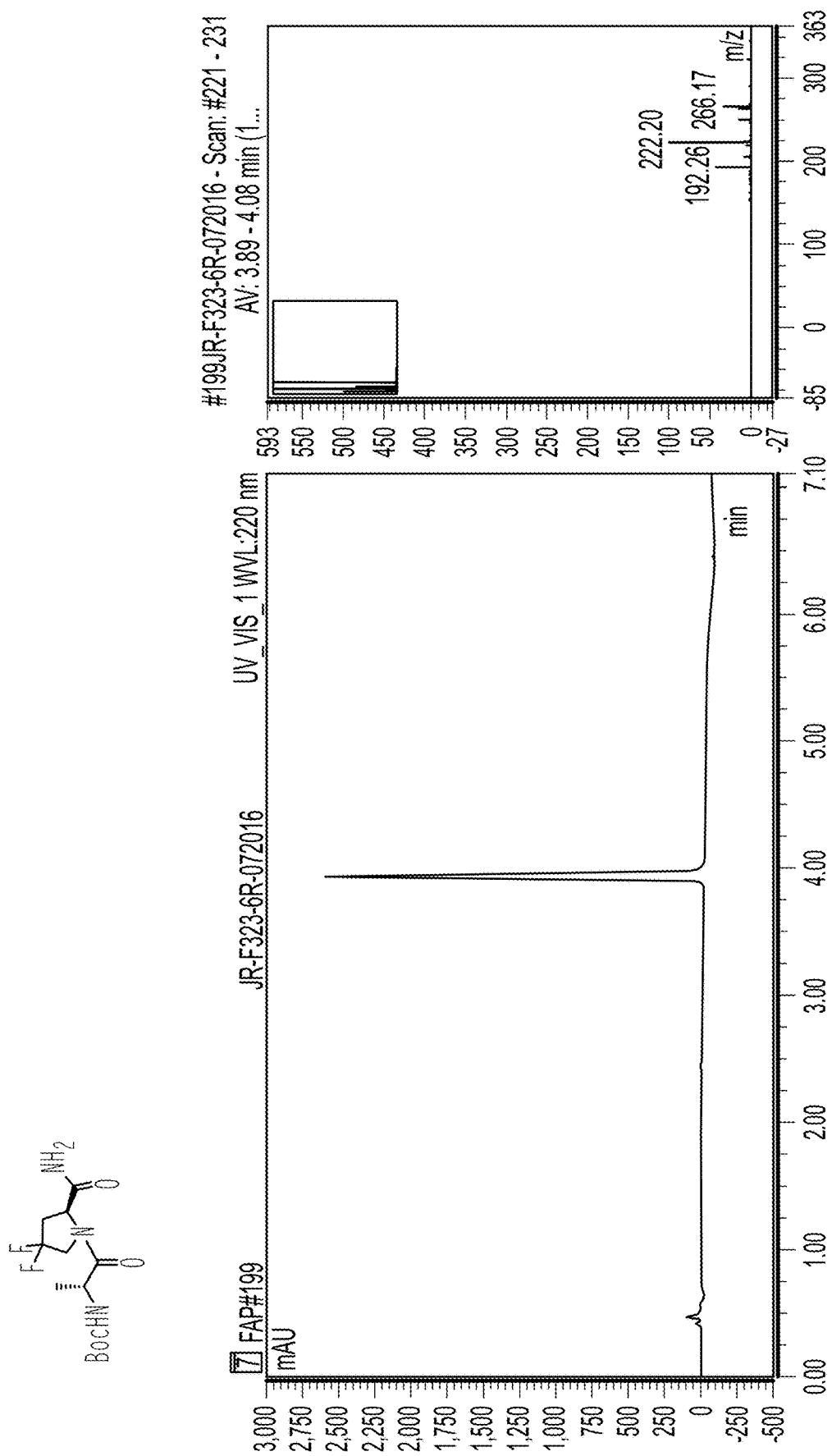
FIG. 1 shows the chemical structure and an LC/MS trace for Compound 3.

Several embodiments of the invention are described by the following enumerated clauses and any combination of these embodiments with the embodiments described in this Detailed Description section is contemplated. It is to be understood that elements and features of the various representative embodiments described below may be combined in different ways to produce new embodiments that likewise fall within the scope of the present teachings.

1. A conjugate having a structure

B-L-X, wherein B comprises a fibroblast activation protein (FAP) inhibitor; L comprises a bivalent linker; and X comprises a near infrared (NIR) dye, a radioactive imaging agent, or a therapeutic agent effective against cancer cells and/or cancer-associated fibroblasts (CAF).

2. The conjugate of clause 1 wherein B has a structure

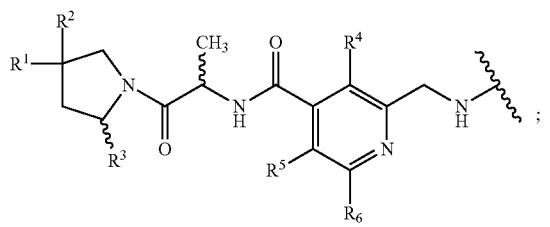

wherein $R^1$ and $R^2$ are the same or different, and are each independently selected from the group consisting of hydrogen, halogen, and $C_1$-$C_4$ alkyl; $R^3$ is a $C_1$-$C_4$ alkyl, nitrile, or isonitrile; and $R^4$, $R^5$, and $R^6$ are the same or different, and are each independently selected from the group consisting of hydrogen, halogen, and $C_1$-$C_4$ alkyl.

3. The conjugate of any preceding clause wherein each of $R^1$ and $R^2$ is a halogen.

4. The conjugate of any preceding clause wherein each of $R^1$ and $R^2$ is fluorine.

5. The conjugate of any preceding clause wherein $R^3$ is nitrile.

6. The conjugate of any preceding clause wherein each of $R^4$, $R^5$, and $R^6$ is hydrogen.

7. The conjugate of any preceding clause wherein B has a structure

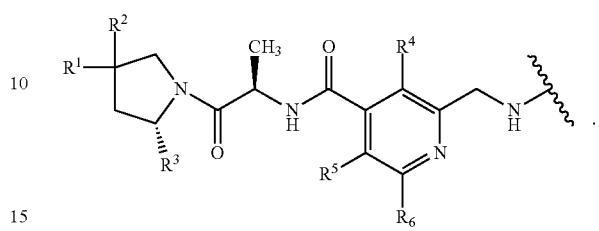

8. The conjugate of any preceding clause wherein B has a structure

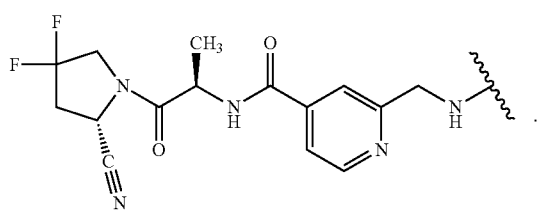 [SMILES: *NCc1cc(C(=O)N[C@H](C)C(=O)N2CC(F)(F)C[C@H]2C#N)ccn1]

9. The conjugate of any preceding clause wherein L comprises a structure

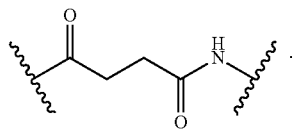 [SMILES: *NC(=O)CCC(*)=O]

10. The conjugate of any preceding clause wherein L comprises a structure

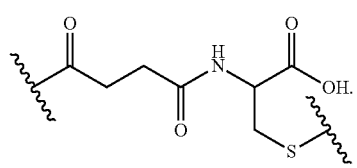 [SMILES: *SCC(NC(=O)CCC(*)=O)C(=O)O]

11. The conjugate of any preceding clause wherein X comprises a NIR dye.

12. The conjugate of any preceding clause wherein the NIR dye is fluorescein isothiocyanate (FITC).

13. The conjugate of any preceding clause wherein the NIR dye is S0456.

14. The conjugate of any preceding clause wherein X has a structure

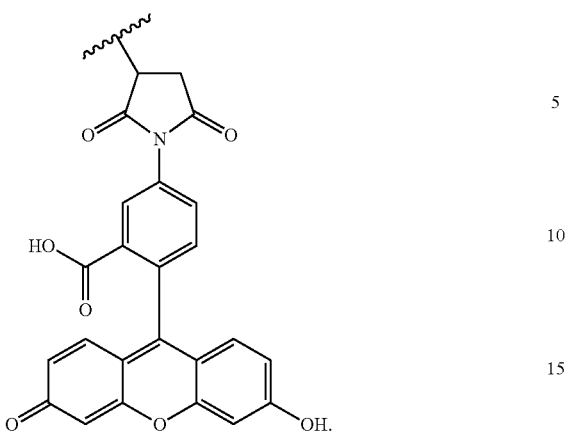
15. The conjugate of any preceding clause wherein X has a structure
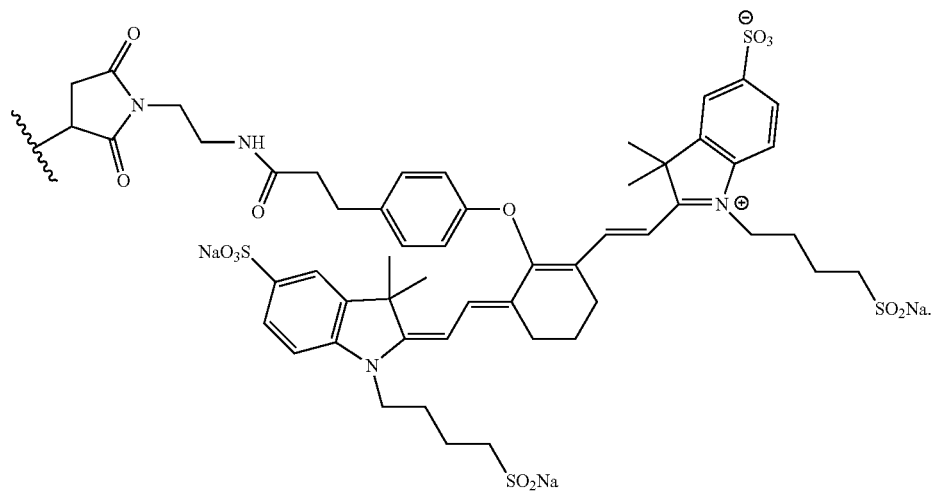
16. The conjugate of any preceding clause having a structure
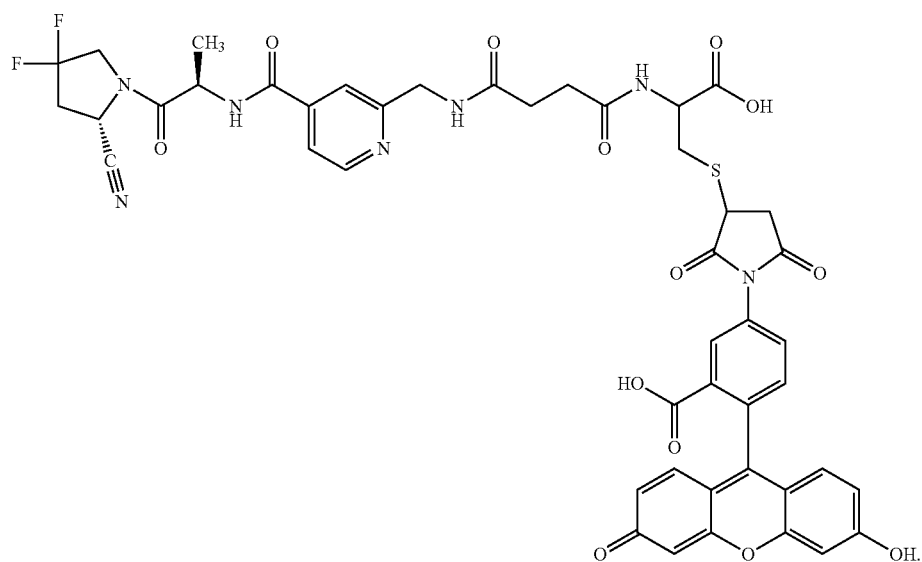 [SMILES: C[C@@H](NC(=O)c1ccnc(CNC(=O)CCC(=O)NC(CSC2CC(=O)N(c3ccc(-c4c5ccc(=O)cc-5oc5cc(O)ccc45)c(C(=O)O)c3)C2=O)C(=O)O)c1)C(=O)N1CC(F)(F)C[C@H]1C#N]

17. The conjugate of any preceding clause having a structure

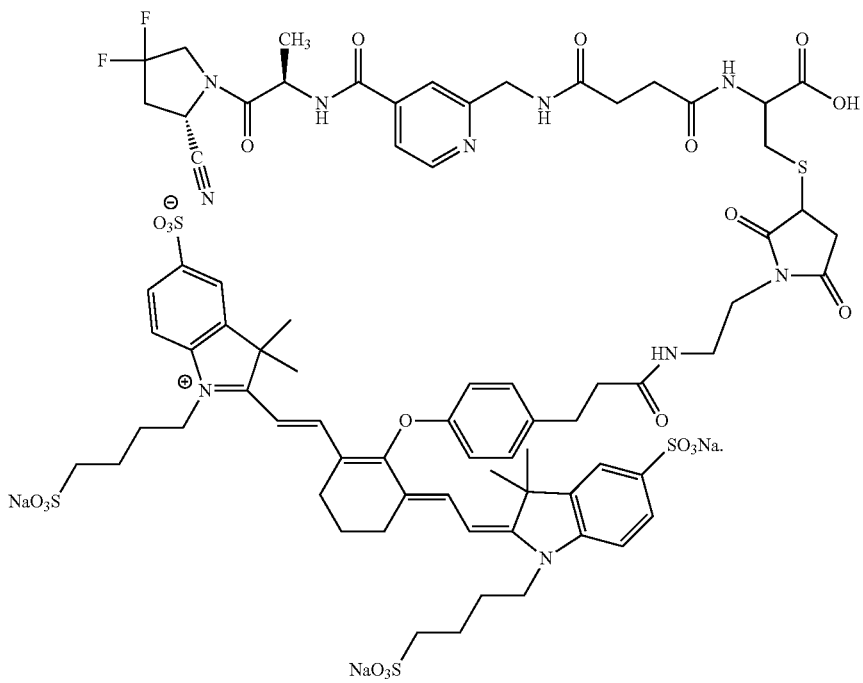

18. The conjugate of any one of clauses 1-10 wherein X comprises a radioactive imaging agent.
19. The conjugate of any one of clauses 1-10 wherein X comprises a therapeutic agent effective against cancer cells and/or CAFs.
20. A conjugate having a structure

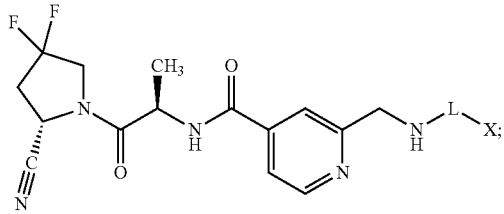

wherein L comprises a bivalent linker; and X comprises a near infrared (NIR) dye.

21. The conjugate of clause 20 having a structure

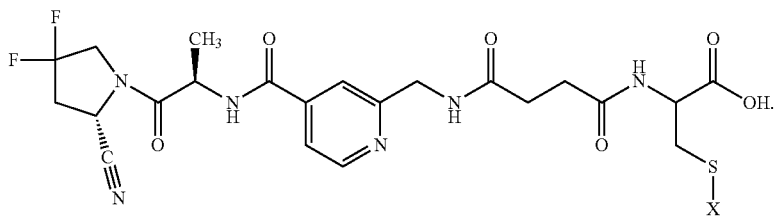

22. A method of surgically removing cancer-associated fibroblasts (CAFs) from a patient, the method comprising:

delivering a conjugate to a tumor microenvironment of the patient, the tumor microenvironment comprising at least one CAF, the conjugate having a structure

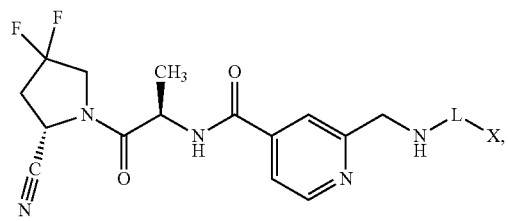

wherein L comprises a bivalent linker and X comprises a near infrared (NIR) dye; causing the NIR dye to fluoresce through an application of an optical stimulus thereto; and cutting CAF-containing tissue of the patient based on a result of the fluorescence.

23. The method of clause 22 wherein the CAF-containing tissue imaged by the conjugate comprises stromal cells.

In each of the foregoing and each of the following embodiments, it is to be understood that the formulae include and represent not only all pharmaceutically acceptable salts of the conjugates, but also include any and all hydrates and/or solvates of the conjugate formulae. It is appreciated that certain functional groups, such as the hydroxy, amino, and like groups form complexes and/or coordination conjugates with water and/or various solvents, in the various physical forms of the conjugates. Accordingly, the above formulae are to be understood to include and represent those various hydrates and/or solvates. It is also to be understood that the non-hydrates and/or non-solvates of the conjugate formulae are described by such formula, as well as the hydrates and/or solvates of the conjugate formulae.

Throughout this description and in the appended claims, the following definitions are to be understood:

As used herein, the phrase "$C_1$-$C_4$ alkyl" refers to a straight, branched or cyclic hydrocarbon chain containing from 1 to 4 carbon atoms. Representative examples of $C_1$-$C_4$ alkyl groups in accordance with the present teachings include but are not limited to methyl, ethyl, propyl, iso-propyl, cyclopropyl, butyl, iso-butyl, tert-butyl, sec-butyl, and cyclobutyl.

As used herein, the term "halogen" refers to fluorine, chlorine, iodine or bromine.

As used herein, "amino acid" (a.k.a. "AA") means any molecule that includes an alpha-carbon atom covalently bonded to an amino group and an acid group. The acid group may include a carboxyl group. "Amino acid" may include molecules having one of the formulas:

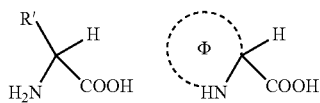

or a derivative thereof, wherein R' is a side group and Φ includes at least 3 carbon atoms. "Amino acid" includes stereoisomers such as the D-amino acid and L-amino acid forms. Illustrative amino acid groups include, but are not limited to, the twenty endogenous human amino acids and their derivatives, such as lysine (Lys), asparagine (Asn), threonine (Thr), serine (Ser), isoleucine (Ile), methionine (Met), proline (Pro), histidine (His), glutamine (Gln), arginine (Arg), glycine (Gly), aspartic acid (Asp), glutamic acid (Glu), alanine (Ala), valine (Val), phenylalanine (Phe), leucine (Leu), tyrosine (Tyr), cysteine (Cys), tryptophan (Trp), phosphoserine (PSER), sulfo-cysteine, arginosuccinic acid (ASA), hydroxyproline, phosphoethanolamine (PEA), sarcosine (SARC), taurine (TAU), carnosine (CARN), citrulline (CIT), anserine (ANS), 1,3-methyl-histidine (ME-HIS), alpha-amino-adipic acid (AAA), beta-alanine (BALA), ethanolamine (ETN), gamma-aminobutyric acid (GAB A), beta-amino-isobutyric acid (BAIA), alpha-amino-butyric acid (BABA), L-allo-cystathionine (cystathionine-A; CYSTA-A), L-cystathionine (cystathionine-B; CYSTA-B), cystine, allo-isoleucine (ALLO-ILE), DL-hydroxylysine (hydroxylysine (I)), DL-allo-hydroxylysine (hydroxylysine (2)), ornithine (ORN), homocystine (HCY), and derivatives thereof. In connection with the embodiments described herein, amino acids can be covalently attached to other portions of the conjugates described herein through their alpha-amino and carboxy functional groups (i.e. in a peptide bond configuration), or through their side chain functional groups (such as the side chain carboxy group in glutamic acid) and either their alpha-amino or carboxy functional groups. It will be understood that amino acids, when used in connection with the conjugates described herein, may exist as zwitterions in a conjugate in which they are incorporated.

In some embodiments, a derivative of an amino acid includes an amino acid that includes a substituent on the side-chain that is not present on a natural amino acid. Some examples of derivatives are provided above. In some embodiments, a derivative of glutamic acids includes the covalent attachment of an amine substituent through the carboxylic acid on the glutamic acid side-chain to form an amide bond. In some embodiments, the amine substituent is an amino sugar, such as 1-deoxy-1-amino-D-glucitol as shown below.

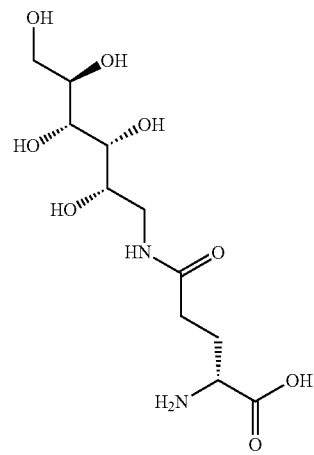 [SMILES: N[C@H](CCC(=O)NC[C@H](O)[C@@H](O)[C@H](O)[C@H](O)CO)C(=O)O]

As used herein, the phrase "therapeutically effective amount" refers to an amount of a drug or pharmaceutical agent that elicits the biological or medicinal response in a subject (i.e. a tissue system, animal or human) that is being sought by a researcher, veterinarian, medical doctor or other clinician, which includes, but is not limited to, alleviation of the symptoms of the disease or disorder being treated. In one aspect, the therapeutically effective amount is that amount of an active which may treat or alleviate the disease or symptoms of the disease at a reasonable benefit/risk ratio applicable to any medical treatment. In another aspect, the therapeutically effective amount is that amount of an inactive prodrug which when converted through normal metabolic processes to produce an amount of active drug capable of eliciting the biological or medicinal response in a subject that is being sought.

It is also appreciated that the dose, whether referring to monotherapy or combination therapy, is advantageously selected with reference to any toxicity, or other undesirable side effect, that might occur during administration of one or more of the conjugates described herein. Further, it is appreciated that the co-therapies described herein may allow for the administration of lower doses of conjugates that show such toxicity, or other undesirable side effect, where those lower doses are below thresholds of toxicity or lower in the therapeutic window than would otherwise be administered in the absence of a cotherapy.

As used herein, the term "administering" includes all means of introducing the conjugates and compositions described herein to the host animal, including, but are not limited to, oral (po), intravenous (iv), intramuscular (im), subcutaneous (sc), transdermal, inhalation, buccal, ocular, sublingual, vaginal, rectal, and the like. The conjugates and compositions described herein may be administered in unit dosage forms and/or formulations containing conventional nontoxic pharmaceutically-acceptable carriers, adjuvants, and/or vehicles.

As used herein, the phrase "pharmaceutical composition" or "composition" refers to a mixture of one or more of the conjugates in accordance with the present teachings, or pharmaceutically acceptable salts, solvates, hydrates thereof, with other chemical components, such as pharmaceutically acceptable excipients. The purpose of a pharmaceutical composition is to facilitate administration of a conjugate to a subject. Pharmaceutical compositions suitable for the delivery of conjugates in accordance with the present teachings and methods for their preparation will be readily apparent to those skilled in the art. Such compositions and methods for their preparation may be found, for example, in Remington's *Pharmaceutical Sciences*, 19th Edition (Mack Publishing Company, 1995).

Unless defined otherwise, all technical and scientific terms used herein have the same meaning as commonly understood to one of ordinary skill in the art to which this invention belongs. Although any methods, devices, and materials similar or equivalent to those described herein may be used in the practice or testing of the present teachings, the preferred methods, devices and materials are now described.

In some embodiments, a conjugate in accordance with the present teachings includes an imaging agent, such as a near infrared (NIR) dye or a radioactive imaging agent. Representative compounds that may be used as imaging agents in accordance with the present teachings include but are not limited to dyes (e.g., rhodamine dyes, cyanine dyes, fluorescein dyes, etc.), PET imaging agents, radiolabeled agents, and the like. Representative examples of rhodamine dyes include but are not limited to 5-carboxytetramethylrhodamine (5-TAMRA), rhodamine B, rhodamine 6G, TRITC, Texas Red, rhodamine 123, sulforhodamine 101, and the like. Examples of fluorescein dyes include but are not limited to fluorescein, fluorescein maleimide (FM), 5-amino-fluorescein, 6-amino-fluorescein, fluorescein isocyanate (FITC), NHS-fluorescein, Oregon Green, Tokyo Green, Singapore Green, Philadelphia Green, and the like. Representative near infrared dyes that may be used in accordance with the present teachings include but are not limited to LS288, IR800, SP054, S0121, KODAK, IRD28, S2076, S0456, and derivatives thereof.

In some embodiments, a radiolabeled agent may be used as an imaging agent in accordance with the present teachings. In some embodiments, a rhodamine dye or fluorescein dye may be isotopically labelled. Examples of isotopes suitable for inclusion in the conjugates include isotopes of hydrogen (e.g., $^2$H and $^3$H), carbon (e.g., $^{13}$C, $^{13}$C, and $^{14}$C), chlorine (e.g., $^{36}$Cl), fluorine (e.g., $^{18}$F), iodine (e.g., $^{123}$I and $^{125}$I) nitrogen (e.g., $^{13}$N and $^{15}$N), oxygen (e.g., $^{15}$O, $^{17}$O, and $^{18}$O), phosphorus (e.g., $^{32}$P), and sulfur (e.g., $^{35}$S).

Certain isotopically-labelled conjugates, for example, those incorporating a radioactive isotope, may be useful in drug and/or substrate tissue distribution studies. The radioactive isotopes tritium (i.e., $^3$H), and carbon-14 (i.e., $^{14}$C) are particularly useful for this purpose in view of their ease of incorporation and ready means of detection.

Substitution with positron emitting isotopes, such as $^{11}$C, $^{18}$F, and $^{13}$N, may be useful in Positron Emission Topography (PET) studies for examining substrate receptor occupancy. Isotopically-labeled conjugates may generally be prepared by conventional techniques known to those skilled in the art or by processes analogous to those described in the accompanying Examples using an appropriate isotopically-labeled reagents in place of the non-labeled reagent previously employed.

In some embodiments, the present disclosure provides methods for imaging a population of cell or tissue, either in vitro or in vivo. It will be appreciated that such in vitro methods may be carried out by any method known in the art. In some embodiments, in vitro imaging methods described herein may include (a) contacting a population of cells with a conjugate in accordance with the present teachings that is suitable for imaging to provide the conjugate bound to cells expressing a FAP protein, and (b) visualizing the conjugate bound to cells by irradiation with light. It will be appreciated that visualizing the conjugate bound to cells by irradiation with light may include irradiation at an excitation wavelength and detection at an emission wavelength. Thus, in some embodiments, in vitro imaging methods described herein may include (a) contacting a population of cells with a conjugate in accordance with the present teachings that is suitable for imaging to provide the conjugate bound to cells expressing a FAP protein, (b) irradiating the conjugate bound to cells expressing a FAP protein with an excitation wavelength light, and (c) detecting light emitted from the cancer cells at an emission wavelength.

In some embodiments, tissues, such as cancerous tumors, may be imaged according to the methods described herein. For example, in some embodiments, in vivo imaging methods in accordance with the present teachings may include (a) administering to the patient a conjugate in accordance with the present teachings that is suitable for imaging; or a pharmaceutically acceptable salt thereof, to provide the conjugate bound to cells expressing a FAP protein; and (b) visualizing the conjugate bound to cells expressing a FAP protein by irradiation with light. It will be appreciated that visualizing the conjugate bound to cells by irradiation with light may include irradiation at an excitation wavelength and detection at an emission wavelength. Thus, in some embodiments, in vivo imaging methods described herein may include (a) administering to the patient a conjugate as described herein that is suitable for imaging; or a pharmaceutically acceptable salt thereof, to provide the conjugate bound to cells expressing a FAP protein; (b) irradiating the conjugate bound to cells expressing a FAP protein with an excitation wavelength light; and (c) detecting light emitted from the cancer cells at an emission wavelength. It will be appreciated that visualizing the conjugate bound to cells by irradiation with light may be carried out using any known imaging techniques (diagnostic or otherwise) or instrumentation known in the art.

In some embodiments, a conjugate in accordance with the present teachings includes a therapeutic agent which, in some embodiments, is therapeutically effective against cancer cells and/or cancer-associated fibroblast (CAFs). The therapeutic agent used in accordance with the present teachings may be any molecule capable of modulating or otherwise modifying cell function, including pharmaceutically active compounds (e.g., a therapeutic agent), or any molecule capable of providing a measurable signal for imaging or visualized cells or tissues (e.g., an imaging agent).

Suitable molecules that may be useful as therapeutic agents include but are not limited to peptides, oligopeptides, retro-inverso oligopeptides, proteins, protein analogs in which at least one non-peptide linkage replaces a peptide linkage, apoproteins, glycoproteins, enzymes, coenzymes, enzyme inhibitors, amino acids and their derivatives, receptors and other membrane proteins; antigens and antibodies thereto; haptens and antibodies thereto; hormones, lipids, phospholipids, liposomes; toxins; antibiotics; analgesics; bronchodilators; beta-blockers; antimicrobial agents; anti-hypertensive agents; cardiovascular agents including antiarrhythmics, cardiac glycosides, antianginals and vasodilators; central nervous system agents including stimulants, psychotropics, antimanics, and depressants; antiviral agents; antihistamines; cancer drugs including chemotherapeutic agents; tranquilizers; anti-depressants; H-2 antagonists; anticonvulsants; antinauseants; prostaglandins and prostaglandin analogs; muscle relaxants; anti-inflammatory substances; stimulants; decongestants; antiemetics; diuretics; antispasmodics; antiasthmatics; anti-Parkinson agents; expectorants; cough suppressants; mucolytics; and mineral and nutritional additives.

In some embodiments, the therapeutic agent may be a tubulysin. Natural tubulysins are generally linear tetrapeptides consisting of N-methyl pipecolic acid (Mep), isoleucine (Ile), an unnatural aminoacid called tubuvaline (Tuv), and either an unnatural aminoacid called tubutyrosine (Tut, an analog of tyrosine) or an unnatural aminoacid called tubuphenylalanine (Tup, an analog of phenylalanine).

In some embodiments, the therapeutic agent is a tetrapeptide of the formula

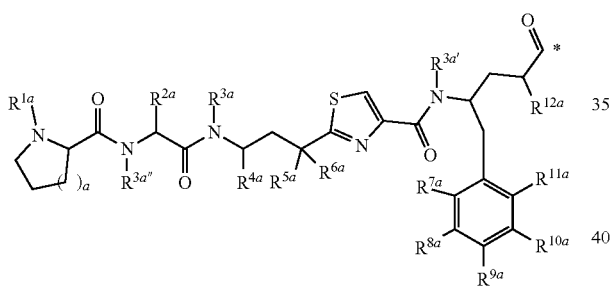

wherein $R^{1a}$, $R^{3a}$, $R^{3a'}$ and $R^{3a''}$ are each independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, $-OR^{13a}$, $-OC(O)R^{13a}$, $-OC(O)NR^{13a}R^{13a'}$, $-OS(O)R^{13a}$, $-OS(O)_2R^{13a}$, $-SR^{13a}$, $-SC(O)R^{13a}$, $-S(O)R^{13a}$, $-S(O)_2R^{13a}$, $-S(O)_2OR^{13a}$, $-S(O)NR^{13a}R^{13a'}$, $-S(O)_2NR^{13a}R^{13a'}$, $-OS(O)NR^{13a}R^{13a'}$, $-OS(O)_2NR^{13a}R^{13a'}$, $-NR^{13a}R^{13a'}$, $-NR^{13a}C(O)R^{14a}$, $-NR^{13a}C(O)OR^{14a}$, $-NR^{13a}C(O)NR^{14a}R^{14a'}$, $-NR^{13a}S(O)R^{14a}$, $-NR^{13a}S(O)_2R^{14a}$, $-NR^{13a}S(O)NR^{14a}R^{14a'}$, $-NR^{13a}S(O)_2NR^{14a}R^{14a'}$, $-P(O)(OR^{13a})_2$, $-C(O)R^{13a}$, $-C(O)OR^{13a}$ or $-C(O)NR^{13a}R^{13a'}$;

$R^{2a}$, $R^{4a}$ and $R^{12a}$ are each independently selected from the group consisting of H, $C_1$-$C_6$ alkyl, $C_2$-$C_6$ alkenyl, $C_2$-$C_6$ alkynyl;

$R^{5a}$ and $R^{6a}$ are each independently selected from the group consisting of H, halogen, $C_1$-$C_6$ alkyl, $C_2$-$C_6$ alkenyl, $C_2$-$C_6$ alkynyl, $-OR^{15a}$, $-SR^{15a}$ and $-NR^{15a}R^{15a'}$, wherein each hydrogen atom in $C_1$-$C_6$ alkyl, $C_2$-$C_6$ alkenyl and $C_2$-$C_6$ alkynyl is independently optionally substituted by halogen, $-OR^{16a}$, $-SR^{16a}$, $-NR^{16a}R^{16a'}$, $-C(O)R^{16a}$, $-C(O)OR^{16a}$ or $-C(O)NR^{16a}R^{16a'}$; or $R^{5a}$ and $R^{6a}$ taken together with the carbon atom to which they are attached form a $-C(O)-$;

each $R^{7a}$, $R^{8a}$, $R^{9a}$, $R^{10a}$ and $R^{11a}$ is independently selected from the group consisting of H, halogen, $C_1$-$C_6$ alkyl, $C_2$-$C_6$ alkenyl, $C_2$-$C_6$ alkynyl, $-CN$, $-NO_2$, $-NCO$, $-OR^{17a}$, $-SR^{17a}$, $-S(O)_2OR^{17a}$, $-NR^{17a}R^{17a'}$, $-P(O)(OR^{17a})_2$, $-C(O)R^{17a}$, $-C(O)OR^{17a}$ and $-C(O)NR^{17a}R^{17a'}$, wherein each hydrogen atom in $C_1$-$C_6$ alkyl, $C_2$-$C_6$ alkenyl and $C_2$-$C_6$ alkynyl is independently optionally substituted by halogen, $-OR^{18a}$, $-SR^{18a}$, $-NR^{18a}R^{18a'}$, $-C(O)OR^{18a}$, $-C(O)OR^{18a}$ or $-C(O)NR^{18a}R^{18a'}$;

each $R^{13a}$, $R^{13a'}$, $R^{14a}$, $R^{14a'}$, $R^{15a}$, $R^{15a'}$, $R^{16a}$, $R^{16a'}$, $R^{17a}$, and $R^{17a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, $-OH$, $-SH$, $-NH_2$ or $-CO_2H$;

each $R^{18a}$ and $R^{18a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl $-C(O)R^{19a}$, $-P(O)(OR^{19a})_2$, and $-S(O)_2OR^{19a}$, each $R^{19}$ is independently selected from H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl;

a is 1, 2 or 3; and

* represents a covalent bond to the rest of the conjugate.

In some embodiments, the therapeutic agent is of the formula

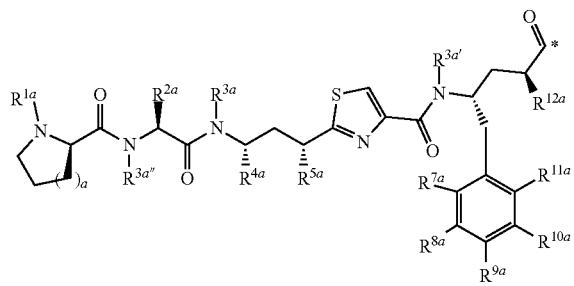

wherein $R^{1a}$, $R^{2a}$, $R^{3a}$, $R^{3a'}$, $R^{3a''}$, $R^{4a}$, $R^{5a}$, $R^{7a'}$, $R^{8a}$, $R^{9a}$, $R^{10a}$, $R^{11a}$ and $R^{12a}$ are as described herein, and * represents a covalent bond to the rest of the conjugate.

In another embodiment, the therapeutic agent may be a naturally occurring tubulysin, or analog or derivative thereof, of the following general formula

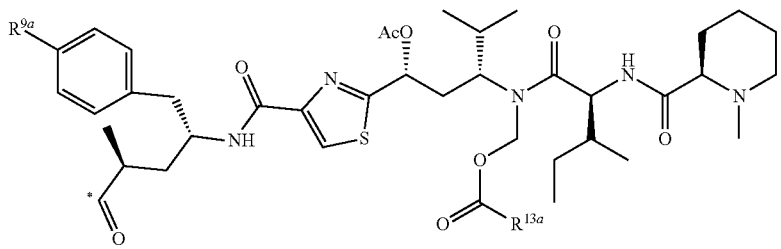

wherein $R^{9a}$ and $R^{13a}$ are as described herein, and * represents a covalent bond to the rest of the conjugate.

Conjugates of each of the foregoing tubulysins are described herein.

In some embodiments, the therapeutic agent may be a naturally occurring tubulysin of the following general formula

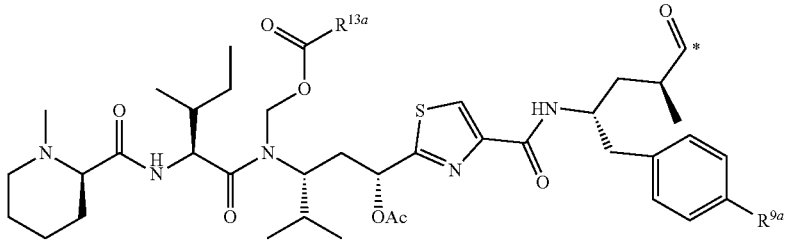

| Factor | $R^{13a}$ | $R^{9a}$ |
|---|---|---|
| A | (CH₃)₂CHCH₂ | OH |
| B | CH₃(CH₂)₂ | OH |
| C | CH₃CH₂ | OH |
| D | (CH₃)₂CHCH₂ | H |
| E | CH₃(CH₂)₂ | H |
| F | CH₂CH₃ | H |
| G | (CH₃)₂C=CH | OH |
| H | CH₃ | H |
| I | CH₃ | OH | and * represents a covalent bond to the rest of the conjugate

In some embodiments, the methods in accordance with the present teachings may be used for both human clinical medicine and veterinary applications as a "subject". Thus, a "subject" may be administered the conjugates in accordance with the present teachings, and may be human ("patient") or, in the case of veterinary applications, may be a laboratory, agricultural, domestic, or wild animal. In some embodiments, the subject may be a human patient, a laboratory animal such as a rodent (e.g., mice, rats, hamsters, etc.), a rabbit, a monkey, a chimpanzee, domestic animals such as dogs, cats, and rabbits, agricultural animals such as cows, horses, pigs, sheep, goats, and wild animals in captivity such as hears, pandas, lions, tigers, leopards, elephants, zebras, giraffes, gorillas, dolphins, and whales.

In some embodiments, the cancers described herein may be a cancer cell population that is tumorigenic, including benign tumors and malignant tumors, or the cancer may be non-tumorigenic. The cancer may arise spontaneously or by such processes as mutations present in the germline of the patient or somatic mutations, or the cancer may be chemically-, virally-, or radiation-induced. Cancers applicable to the present teachings include but are not limited to a carcinoma, a sarcoma, a lymphoma, a melanoma, a mesothelioma, a nasopharyngeal carcinoma, a leukemia, an adenocarcinoma, and a myeloma.

In some embodiments, the cancers may be lung cancer, bone cancer, pancreatic cancer, skin cancer, cancer of the head, cancer of the neck, cutaneous melanoma, intraocular melanoma uterine cancer, ovarian cancer, endometrial cancer, leiomyosarcoma, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, small cell lung cancer, cancer of the adrenal gland, sarcoma of soft tissue, cancer of the urethra, cancer of the penis, prostate cancer, chronic leukemia, acute leukemia, lymphocytic lymphomas, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, cholangiocarcinoma, Hurthle cell thyroid cancer or adenocarcinoma of the gastroesophageal junction.

In some embodiments of the methods described herein, pharmaceutically acceptable salts of conjugates in accordance with the present teachings are provided. Pharmaceutically acceptable salts of conjugates in accordance with the present teachings include acid addition and base salts thereof.

Suitable acid addition salts are formed from acids which form non-toxic salts. Illustrative examples include but are not limited to the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts of the conjugates described herein are formed from bases which form non-toxic salts. Illustrative examples include but are not limited to the arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

In some embodiments, conjugates in accordance with the present teachings may be administered as a formulation in association with one or more pharmaceutically acceptable carriers. The carriers may be excipients. The choice of carrier may depend on factors such as the particular mode of administration, the effect of the carrier on solubility and stability, and the nature of the dosage form. Pharmaceutical compositions suitable for the delivery of conjugates as described herein and methods for their preparation will be readily apparent to those skilled in the art. Such compositions and methods for their preparation may be found, for example, in *Remington: The Science & Practice of Pharmacy*, 21th Edition (Lippincott Williams & Wilkins, 2005).

In some embodiments, a pharmaceutically acceptable carrier includes any and all solvents, dispersion media, coatings, antibacterial and antifungal agents, isotonic and absorption delaying agents, and the like, and combinations thereof, that are physiologically compatible. In some embodiments, the carrier is suitable for parenteral administration. Pharmaceutically acceptable carriers include sterile aqueous solutions or dispersions and sterile powders for the extemporaneous preparation of sterile injectable solutions or dispersions. Supplementary active compounds may also be incorporated into compositions of the invention.

In some embodiments, liquid formulations may include suspensions and solutions. Such formulations may comprise a carrier, for example, water, ethanol, polyethylene glycol, propylene glycol, methylcellulose or a suitable oil, and one or more emulsifying agents and/or suspending agents. Liquid formulations may also be prepared by the reconstitution of a solid.

In some embodiments, an aqueous suspension may contain the active materials in admixture with appropriate excipients. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally-occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and a hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions may also contain one or more preservatives, for example, ascorbic acid, ethyl, n-propyl, or p-hydroxybenzoate; or one or more coloring agents.

In some embodiments, dispersible powders and granules suitable for preparation of an aqueous suspension by the addition of water provide the active ingredient in admixture with a dispersing or wetting agent, suspending agent and one or more preservatives. Additional excipients, for example, coloring agents, may also be present.

Suitable emulsifying agents may be naturally-occurring gums, for example, gum acacia or gum tragacanth; naturally-occurring phosphatides, for example, soybean lecithin; and esters including partial esters derived from fatty acids and hexitol anhydrides, for example, sorbitan mono-oleate, and condensation products of the said partial esters with ethylene oxide, for example, polyoxyethylene sorbitan monooleate.

In some embodiments, isotonic agents, for example, sugars, polyalcohols such as mannitol, sorbitol, or sodium chloride may be included in the composition. Prolonged absorption of injectable compositions may be brought about by including in the composition an agent which delays absorption, for example, monostearate salts and gelatin.

Illustrative formats for oral administration include but are not limited to tablets, capsules, elixirs, syrups, and the like.

Depending upon the cancer type as described herein, the route of administration and/or whether the conjugates are administered locally or systemically, a wide range of permissible dosages are contemplated herein, including doses falling in the range from about 1 µg/kg to about 1 g/kg. The dosages may be single or divided, and may administered according to a wide variety of protocols, including q.d., b.i.d., t.i.d., or even every other day, biweekly (b.i.w.), once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In some embodiments, a conjugate in accordance with the present teachings may be administered directly into the blood stream, into muscle, or into an internal organ. Suitable routes for such parenteral administration include intravenous, intraarterial, intraperitoneal, intrathecal, epidural, intracerebroventricular, intraurethral, intrasternal, intracranial, intratumoral, intramuscular and subcutaneous delivery. Suitable means for parenteral administration include needle (including microneedle) injectors, needle-free injectors and infusion techniques.

In some embodiments, parenteral formulations are typically aqueous solutions which may contain carriers or excipients such as salts, carbohydrates and buffering agents (preferably at a pH of from 3 to 9), but, for some applications, they may be more suitably formulated as a sterile non-aqueous solution or as a dried form to be used in conjunction with a suitable vehicle such as sterile, pyrogen-free water. In other embodiments, any of the liquid formulations described herein may be adapted for parenteral administration of the conjugates described herein. The preparation of parenteral formulations under sterile conditions, for example, by lyophilization under sterile conditions, may readily be accomplished using standard pharmaceutical techniques well known to those skilled in the art. In some embodiments, the solubility of a conjugate as described herein used in the preparation of a parenteral formulation may be increased by the use of appropriate formulation techniques, such as the incorporation of solubility-enhancing agents.

In some embodiments, formulations for parenteral administration may be formulated for immediate and/or modified release. In some embodiments, active agents in accordance with the present teachings (i.e., the conjugates described herein) may be administered in a time release formulation, for example in a composition which includes a slow release polymer. The active agents may be prepared with carriers that will protect the conjugate against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PGLA). Methods for the preparation of such formulations are generally known to those skilled in the art. In other embodiments, the conjugates in accordance with the present teachings or compositions comprising the conjugates may be continuously administered, where appropriate.

In some embodiments, a kit is provided. If a combination of active conjugates as described herein is to be administered, two or more pharmaceutical compositions may be combined in the form of a kit suitable for sequential administration or co-administration of the compositions. Such a kit may include two or more separate pharmaceutical compositions, at least one of which contains a conjugate in accordance with the present teachings, and means for separately retaining the compositions, such as a container, divided bottle, or divided foil packet. In some embodiments, compositions comprising one or more conjugates as described herein, in containers having labels that provide instructions for use of the conjugates as described herein for patient selection and/or treatment are provided.

As used herein, the term "kit" refers to an assembly of materials that are used in performing a method in accordance with the present teachings. The components of the kit may be provided in packaged combination in the same or in separate containers, depending on their cross-reactivities and stabilities, and in liquid or in solid form. The amounts and proportions of components provided in the kit may be selected so as to provide optimum results for a particular application. While in some embodiments, the components to be administered (e.g., to a patient) may be provided in separate physical forms (e.g., a kit containing one or more compositions and one or more fluids), it is to be understood that in other embodiments, all of the components that are to be introduced to the patient may be provided together in one common physical form (e.g., one composition or one fluid).

The components included in kits in accordance with the present teachings may be supplied in all manner of containers such that the activities of the different components are substantially preserved, while the components themselves are not substantially adsorbed or altered by the materials of the container. Suitable containers include but are not limited to ampoules, bottles, test tubes, vials, flasks, syringes, bags and envelopes (e.g., foil-lined), and the like. The containers may be formed of any suitable material including but not limited to glass, organic polymers (e.g., polycarbonate, polystyrene, polyethylene, polypropylene, etc.), ceramic, metal (e.g., aluminum), metal alloys (e.g., steel), cork, and the like. In addition, the containers may contain one or more access ports (e.g., for access via a needle), such as may be provided by a septum. Preferred materials for septa include rubber and polymers including but not limited to, for example, polytetrafluoroethylene of the type sold under the trade name TEFLON by DuPont (Wilmington, Del.). In addition, the containers may contain two or more compartments separated by partitions or membranes that can be removed to allow mixing of the components.

Kits in accordance with the present teachings may also be supplied with other items known in the art and/or which may be desirable from a commercial and user standpoint, including but not limited to instructions for adding the components of the kit to a heat exchange system.

Instructional materials provided with kits in accordance with the present invention may be printed (e.g., on paper) and/or supplied in an electronic-readable medium (e.g., floppy disc, CD-ROM, DVD-ROM, zip disc, videotape, audio tape, etc.). Alternatively, instructions may be provided by directing a user to an Internet web site (e.g., specified by the manufacturer or distributor of the kit) and/or via electronic mail, text message, social media, and/or the like, and combinations thereof.

In some embodiments, sterile injectable solutions may be prepared by incorporating the active agent in the required amount in an appropriate solvent with one or a combination of ingredients described above, as required, followed by filtered sterilization. Typically, dispersions are prepared by incorporating the conjugate into a sterile vehicle which contains a dispersion medium and any additional ingredients of those described above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof, or the ingredients may be sterile-filtered together.

The composition may be formulated as a solution, microemulsion, liposome, or other ordered structure suitable to high drug concentration. The carrier may be a solvent or dispersion medium containing, for example, water, ethanol, polyol (e.g., glycerol, propylene glycol, and liquid polyethylene glycol, and the like), and suitable mixtures thereof. In some embodiments, the proper fluidity may be maintained, for example, by the use of a coating such as lecithin, by the maintenance of the required particle size in the case of dispersion and by the use of surfactants.

Any effective regimen for administering the conjugates described herein may be used. For example, conjugates described herein may be administered as single doses, or the doses may be divided and administered as a multiple-dose daily regimen. Further, a staggered regimen, for example, one to five days per week may be used as an alternative to daily treatment, and for the purpose of the methods described herein, such intermittent or staggered daily regimen is considered to be equivalent to every day treatment and is contemplated. In some embodiments, the patient is treated with multiple injections of a conjugate in accordance with the present teachings to treat the cancer. In some embodiments, the patient is injected multiple times (e.g., about 2 up to about 50 times) with a conjugate in accordance with the present teachings, for example, at 12-72 hour intervals or at 48-72 hour intervals. Additional injections of a conjugate in accordance with the present teachings may be administered to the patient at an interval of days or months after the initial injections(s) and the additional injections may prevent recurrence of the cancer.

Any suitable course of therapy with the conjugates in accordance with the present teachings may be used. In some embodiments, individual doses and dosage regimens are selected to provide a total dose administered during a month of about 15 mg. In some examples, a conjugate in accordance with the present teachings is administered in a single daily dose administered five days a week, in weeks 1, 2, and 3 of each 4 week cycle, with no dose administered in week 4. In an alternative example, a conjugate in accordance with the present teachings is administered in a single daily dose administered three days a week, of weeks 1, and 3 of each 4 week cycle, with no dose administered in weeks 2 and 4. In an alternative example, a conjugate in accordance with the present teachings is administered biweekly on weeks 1 and 2 (i.e., on days 1, 4, 8, 11, of a 3-week cycle). In an alternative example, a conjugate described herein is administered and once weekly on weeks 1 and 2 (i.e., days 1 and 8 of a 3-week cycle).

The unitary daily dosage of the conjugates in accordance with the present teachings may vary significantly depending on the patient condition, the cancer being treated, the route of administration of the conjugates described herein and tissue distribution, and the possibility of co-usage of other therapeutic treatments, such as radiation therapy or additional drugs in combination therapies. The effective amount to be administered to a patient is based on body surface area, mass, and physician assessment of patient condition. Therapeutically effective doses (also referred to herein as "therapeutically effective amounts") may range, for example, from about 0.5 mg/m$^2$ to about 20.0 mg/m$^2$.

The conjugates in accordance with the present teachings may contain one or more chiral centers, or may otherwise be capable of existing as multiple stereoisomers. Accordingly, it is to be understood that the present invention includes pure stereoisomers as well as mixtures of stereoisomers, such as enantiomers, diastereomers, and enantiomerically or diastereomerically enriched mixtures. The conjugates in accordance with the present teachings may be capable of existing as geometric isomers. Accordingly, it is to be understood that the present invention includes pure geometric isomers or mixtures of geometric isomers.

It is appreciated that the conjugates in accordance with the present teachings may exist in unsolvated forms as well as solvated forms, including hydrated forms. In general, the solvated forms are equivalent to unsolvated forms and are encompassed within the scope of the present invention. The conjugates described herein may exist in multiple crystalline or amorphous forms. In general, all physical forms are equivalent for the uses contemplated by the present invention and are intended to be within the scope of the present invention.

In some embodiments, compositions and/or dosage forms for administration of a conjugate in accordance with the present teachings are prepared from a conjugate with a purity of at least about 90%, or about 95%, or about 96%, or about 97%, or about 98%, or about 99%, or about 99.5%. In other embodiments, compositions and or dosage forms for administration of a conjugate in accordance with the present teachings are prepared from a conjugate with a purity of at least 90%, or at least 95%, or at least 96%, or at least 97%, or at least 98%, or at least 99%, or at least 99.5%.

The FAP-targeted imaging agents described herein allow the imaging of tumor microenvironment and can allow surgeons to dissect the CAFs cells through fluorescence-guided surgery. The imaging agents described herein in combination with other cancer cell targeted imaging agents can further enhance the outcome of the fluorescence-guided surgery by allowing surgeons to remove the CAFs cells of the tumor microenvironment which cannot be achieved by the cancer cell targeted imaging agents. This can also reduce the chances of tumor recurrence post-surgery due to leftover CAFs compared to imaging only with cancer cell targeted imaging agents.

In addition, the agents and methods described herein may open the door for the fluorescence guided surgery of cancers in which the cancer cells themselves do not express the cancer associated antigens such as LHRH-R, folate receptor, PSMA, etc. but the CAFs supporting those cancers express FAP. Dissection of the cells of tumor microenvironment will further contribute to decreasing the recurrence of the cancer post-surgery. In some embodiments, the FAP-targeted near-infrared dye conjugates may be combined with other cancer cell targeted imaging agents to allow imaging both cancer cells and tumor microenvironment.

The FAP-targeted near-infrared dye conjugates described herein may allow for high tumor penetration, low photo bleaching, and high signal to noise ratio in addition to the targeting specificity of FAP inhibitor. In addition, the dye conjugates may rapidly clear from the receptor negative tissues. Since FAP is expressed in CAFs of most solid tumors, FAP targeted NIR dyes may be used for imaging many types of cancers.

The following examples and representative procedures illustrate features in accordance with the present teachings, and are provided solely by way of illustration. They are not intended to limit the scope of the appended claims or their equivalents.

Materials. Benzotriazol-1-yl-oxytripyrrolidinophosphonium hexafluorophosphate (PyBop), N,N-Dimethylmethanamide (DMF), N-ethyl-N-isopropylpropan-2-amine (DIPEA), isopropyl alcohol (IPA,) dichloromethane (DCM) and trifluoroacetic acid (TFA), 1,2-ethanedithiol, triisopropylsilane (TIPS), and all other chemical reagents were purchased from Sigma-Aldrich. Cell culture reagents such as rosewell park memorial institute medium 1640 (RPMI 1640) was purchased from GIBCO whereas fetal bovine serum (FBS), 1% penicillin-streptomycin, 2 Mm glutamine were purchased from Life Technologies.

Compound Examples

Scheme 1. Synthesis of fibroblast activation protein a (FAP) ligand JFL

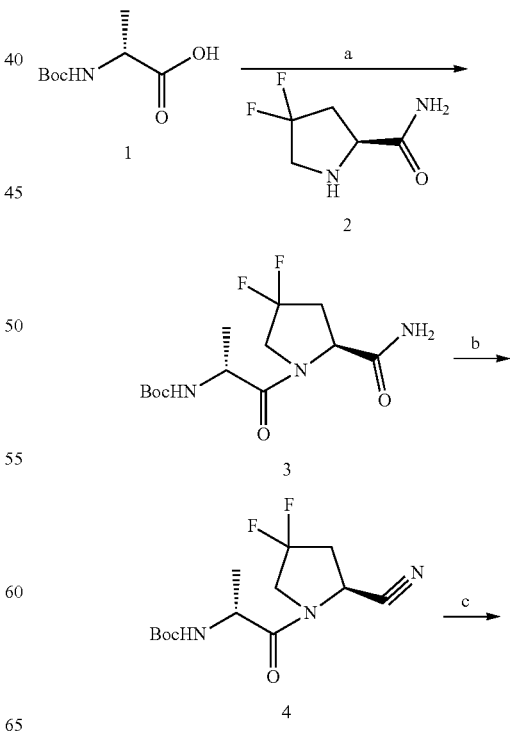

45

-continued

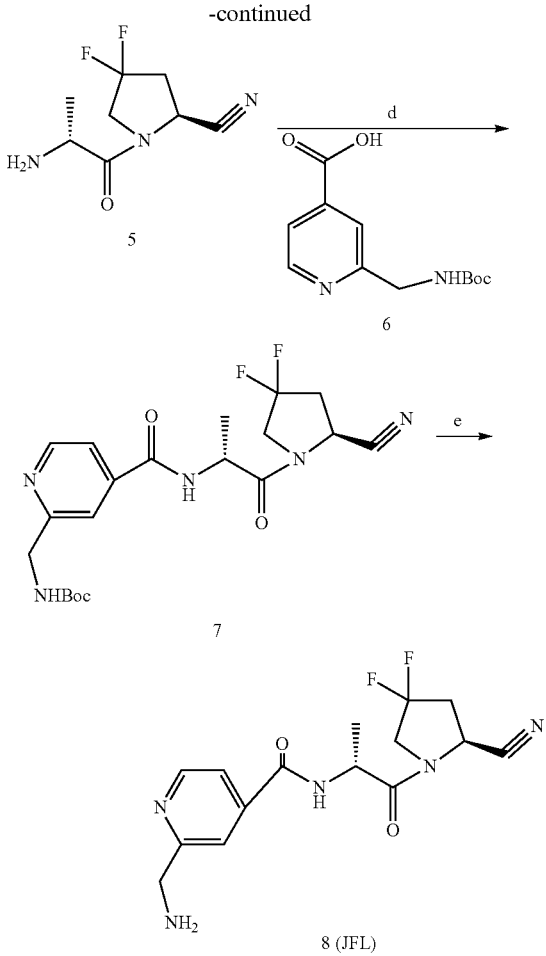

Reagents and conditions a) HATU, Anhy. DIPEA, Any. DMF, rt; b) TFAA, Anh. DCM, Anhy. Pyrine, rt; c) TFA, rt; d) HATU, Anhy. DIPEA, Anhy. DMF, rt; e) TFA, rt.

Synthesis of JFL was initiated by coupling compound 1 and 2 by using HATU as coupling agent to yield compound 3. The amide group on compound 3 was converted to nitrile (compound 4) by using TFAA. Compound 4 was then subjected to Boc deprotection followed by coupling with compound 6 to yield the yield compound 7. Compound 8 was obtained by deprotecting the Boc group on compound 7. Compound 8 is alternatively referred to herein as the FAP ligand JFL.

Compound 3. To a solution of 1 in anhydrous DMF 1 equivalnce of compound 2 and HATU was added. To the above solution anhydrous DIPEA (5 eq) was added and stirred under argon atmosphere for 6 h. The crude product was purified using RP-HPLC [A=2 Mm ammonium acetate buffer (pH 7.0), B=acetonitrile, solvent gradient 0% B to 80% B in 35 min] to yield the requisite product. LRMS-LC/MS (m/z): [M-FH]$^+$ calcd for $C_{13}H_{21}F_2N_3O_4$, 321.32; found 323. LC/MS trace of Compound 3 is shown in FIG. 1.

Figure 2:
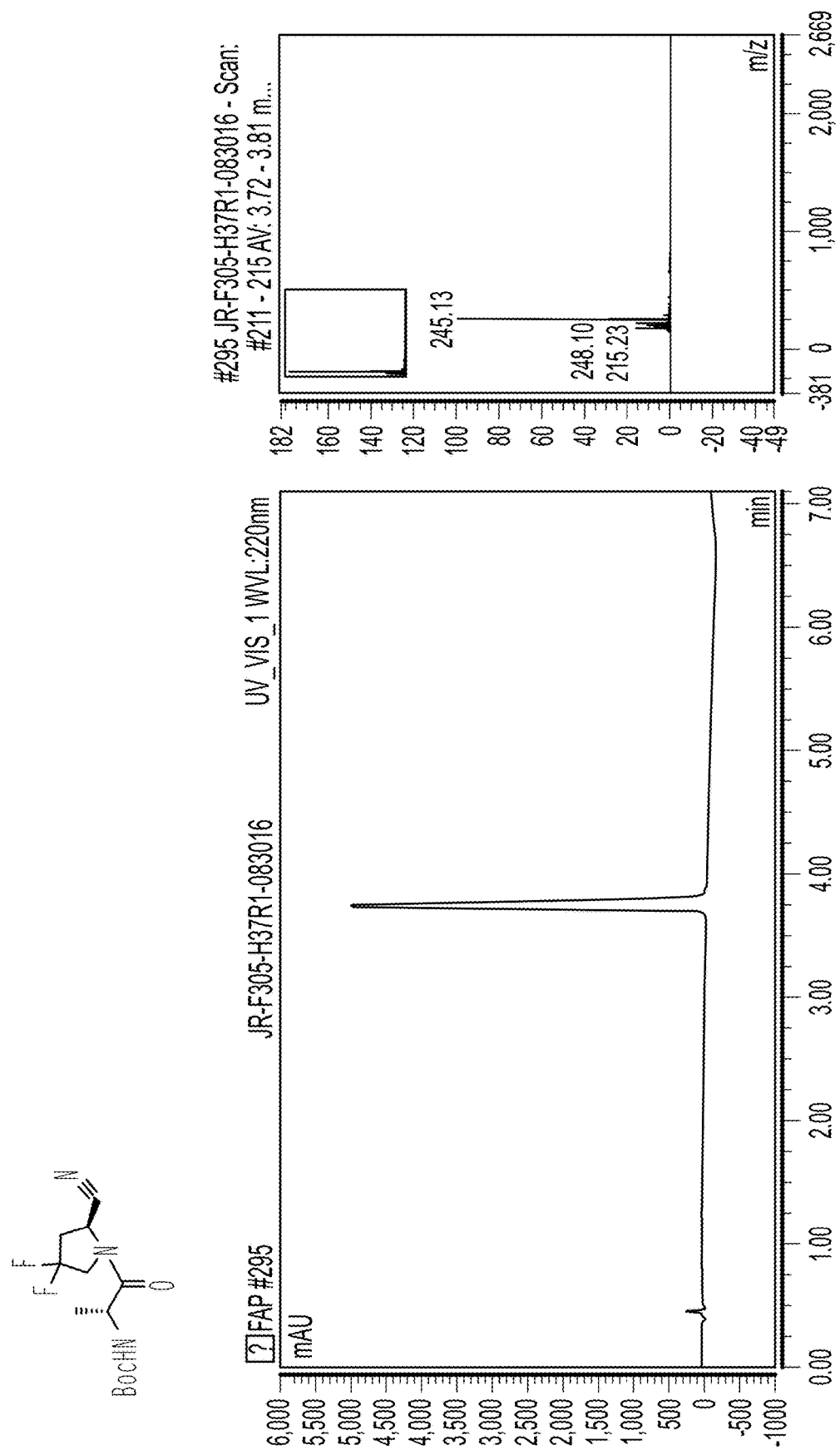
FIG. 2 shows the chemical structure and an LC/MS trace for Compound 4.

Compound 4. The HPLC purified compound 3 was dissolved in anhy. DCM. To this solution was added anhydrous pyridine (1 eq) followed by TFAA (1 eq). The reaction mixture was stirred at room temperature for 1 h. Completion of the reaction was monitored by LC/MS. The crude product was purified using RP-HPLC [A=2 Mm ammonium acetate buffer (pH 7.0), B=acetonitrile, solvent gradient 0% B to 80% B in 35 min] to yield the requisite product. LRMS-LC/MS (m/z): [M+H]$^+$ calcd for $C_{13}H_{19}F_2N_3O_3$. 303.31; found 305. LC/MS trace of Compound 4 is shown in FIG. 2.

Figure 3:
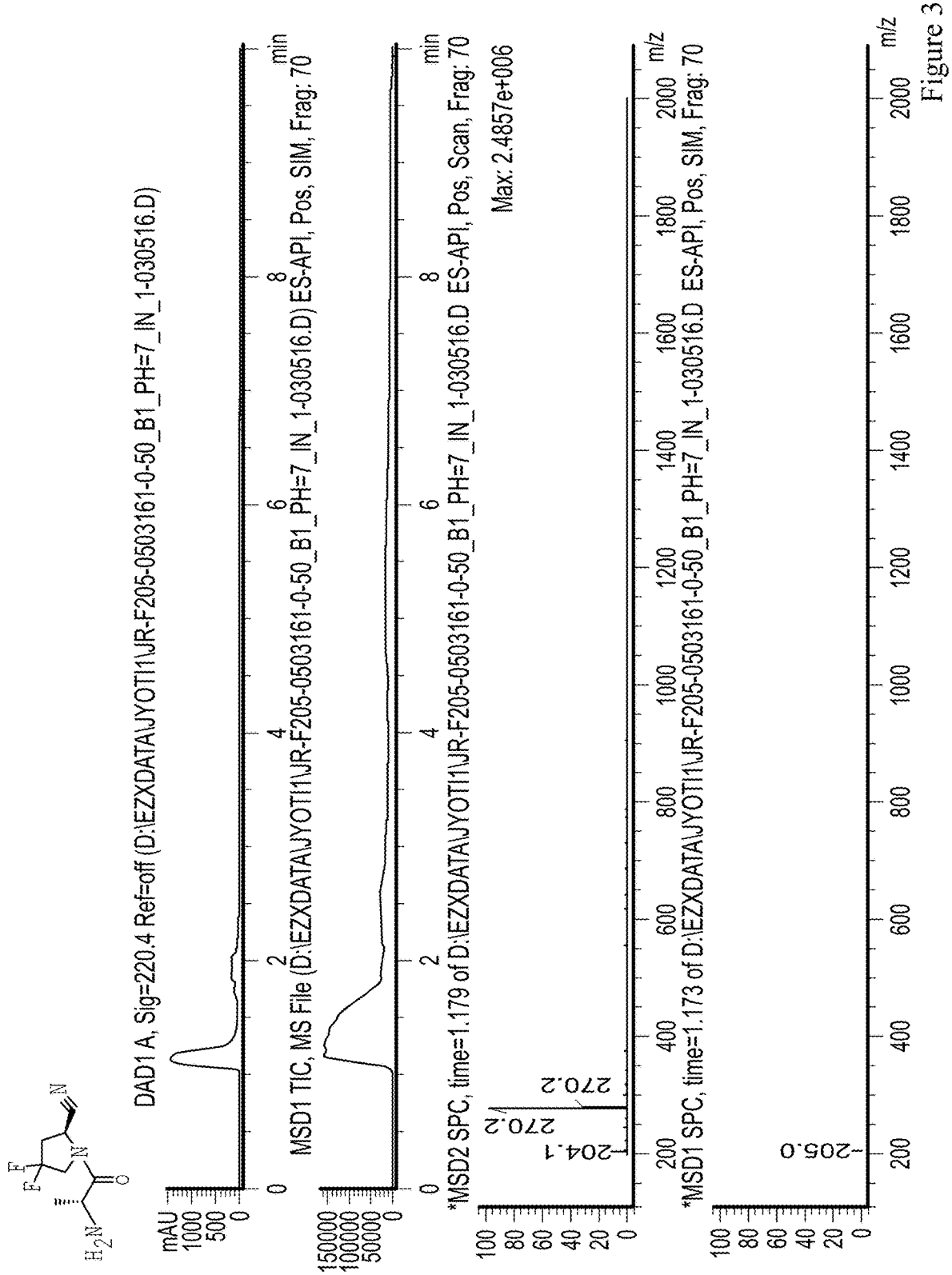
FIG. 3 shows the chemical structure and an LC/MS trace for Compound 5.
Figure 4:
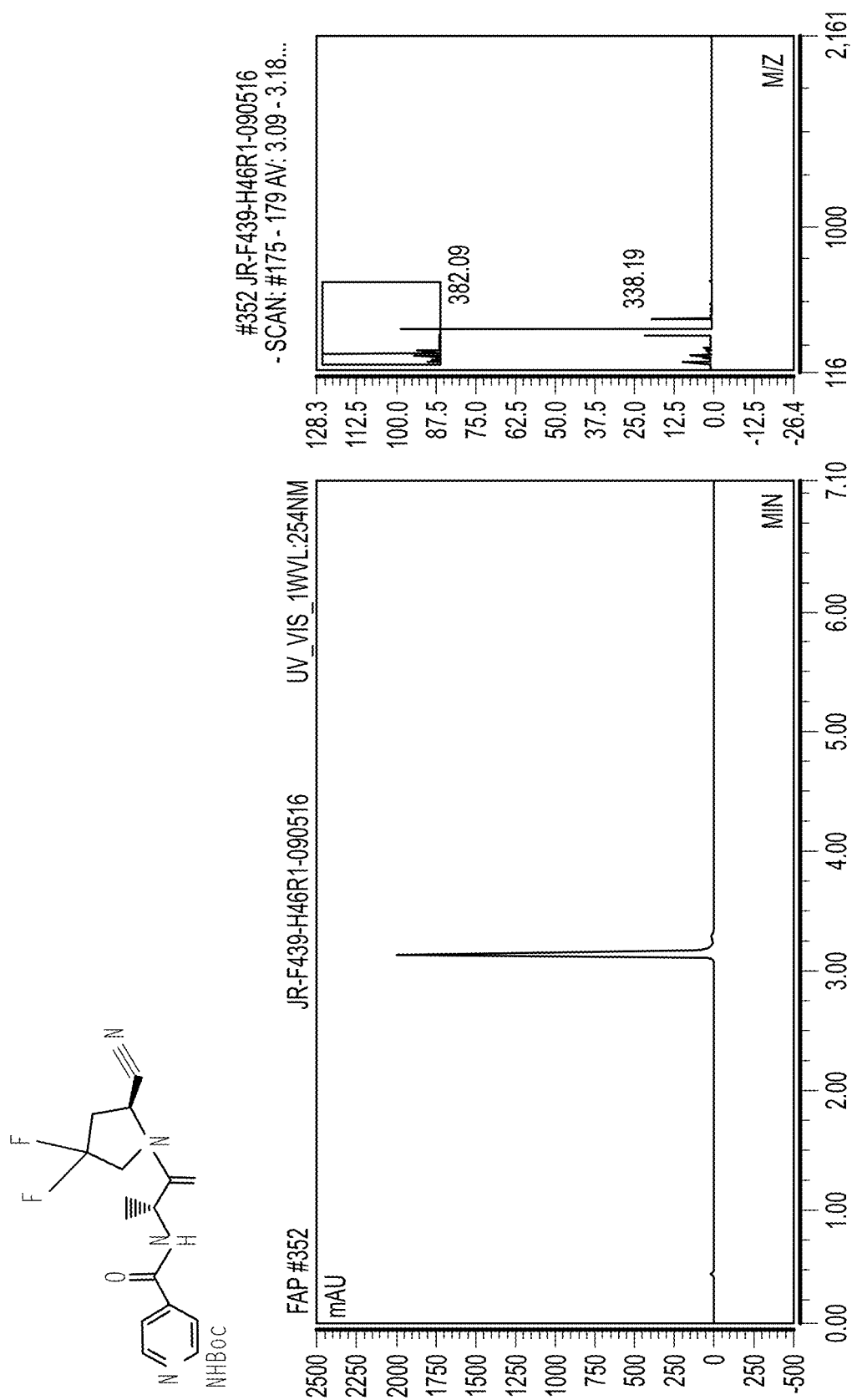
FIG. 4 shows the chemical structure and an LC/MS trace for Compound 7.

Compound 7. Compound 4 was dissolved in TFA and stirred at room temperature for 30 min. Completion of the reaction was monitored through LC/MS. TFA was evaporated by using rotary evaporator and the compound 5 was dried under high vacuum and used further without any purification. LC/MS trace of Compound 5 is shown in FIG. 3. To a solution of compound 5, compound 6 (1 eq) and HATU (1 eq) in DMF DIPEA (5 eq) was added and stirred under argon atmosphere for 6 h. The completion of the reaction was monitored by LC/MS. The crude compound 7 was purified using RP-HPLC [A=2 Mm ammonium acetate buffer (pH 7.0), B=acetonitrile, solvent gradient 0% B to 80% B in 35 min] to yield the requisite product. LRMS-LC/MS (m/z): [M+H]$^+$ calcd for $C_{20}H_{25}F_2N_5O_4$, 437.45; found 438. LC/MS trace of Compound 7 is shown in FIG. 4.

Figure 5:
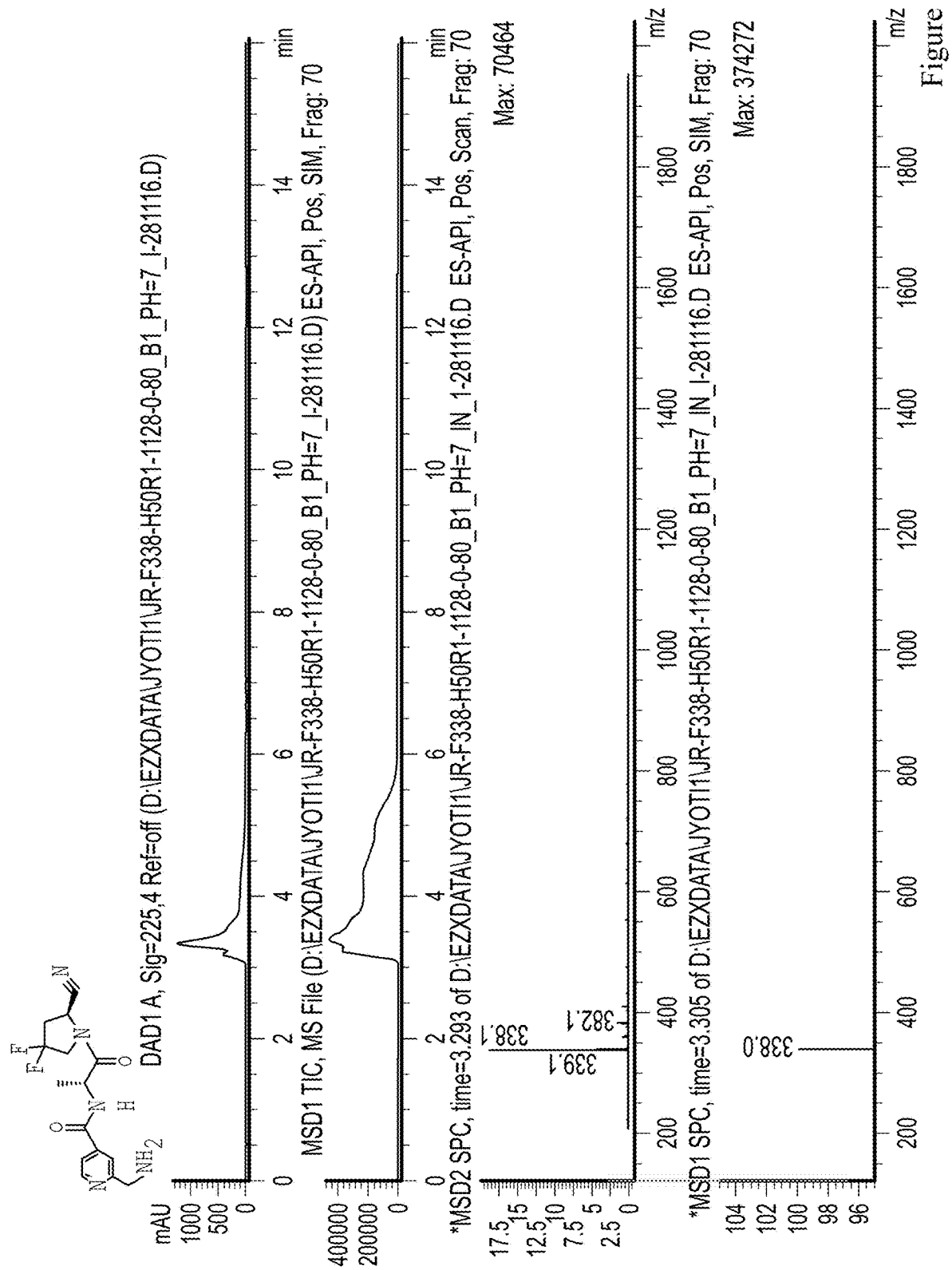
FIG. 5 shows the chemical structure and an LC/MS trace for Compound 8 (JFL).

Compound 8. Compound 7 was dissolved in TFA and stirred ad room temperature for 30 min. TFA was removed by using rotary evaporator and the crude compound 8 was used for the next reaction without any further purification. LRMS-LC/MS (m/z): [M+H]$^+$ calcd for $C_{15}H_{17}F_2N_5O_2$, 337.33; found 338. LC/MS trace of Compound 8 is shown in FIG. 5.

Scheme 2. Synthesis of JFL-L1-S0456 and JFL-L1-FM.

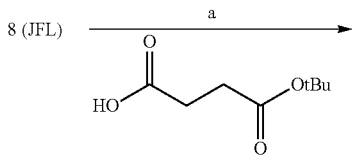

-continued
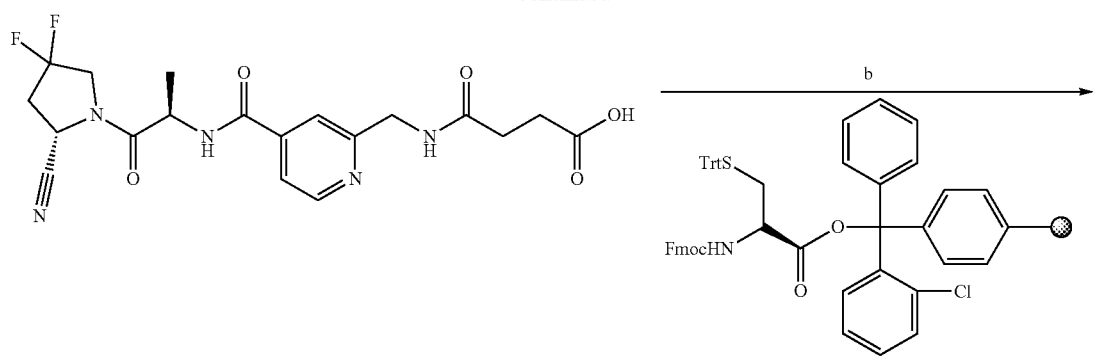
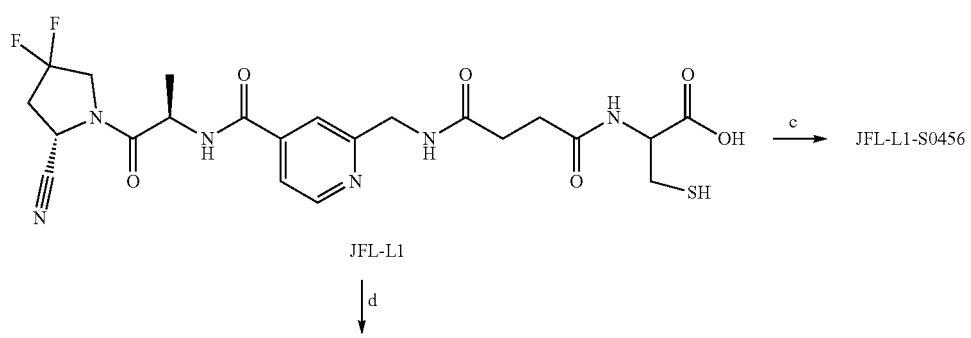
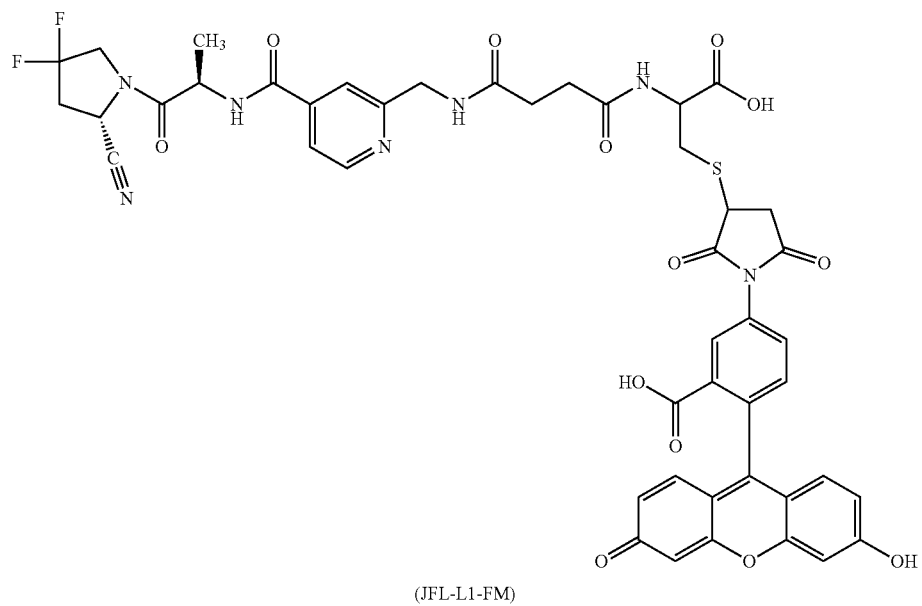
(JFL-L1-FM)

-continued

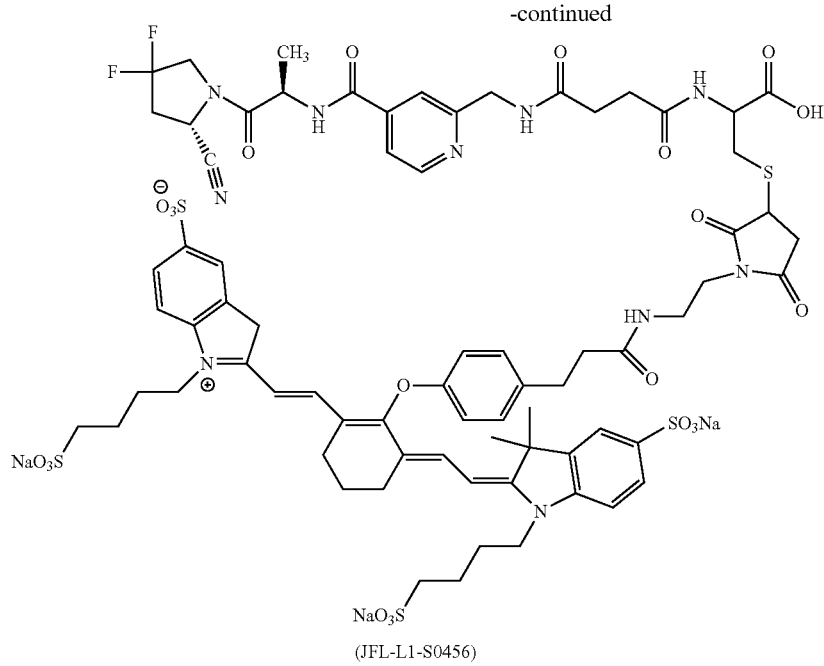

(JFL-L1-S0456)

Reagents and conditions: a) (i) HATU, Anhy. DIPEA, Anhy. DMF, rt. (ii) TFA, rt; b) (i) PyBop, Anhy. DMF, Any. DIPEA, rt. (iii) TFA/H₂O/TIPS/EDT (92.5:2.5:2.5:2.5), 1 h; c) DMSO, DIPEA, S0456 maleimide, rt; d) DMSO, DIPEA, fluorescein maleimide, rt.

Compound 8 was linked to a spacer and is designated herein as JFL-L1. The ligand was linked to the linker partially in solution phase and by standard solid phase peptide synthesis. This was then coupled with the maleimide derivatives of FM or S0456 to yield JFL-L1-FM or JFL-L1-S0456 respectively. Intermediates and final conjugates were purified by HPLC and characterized by using LC/MS and UPLC.

Figure 6:
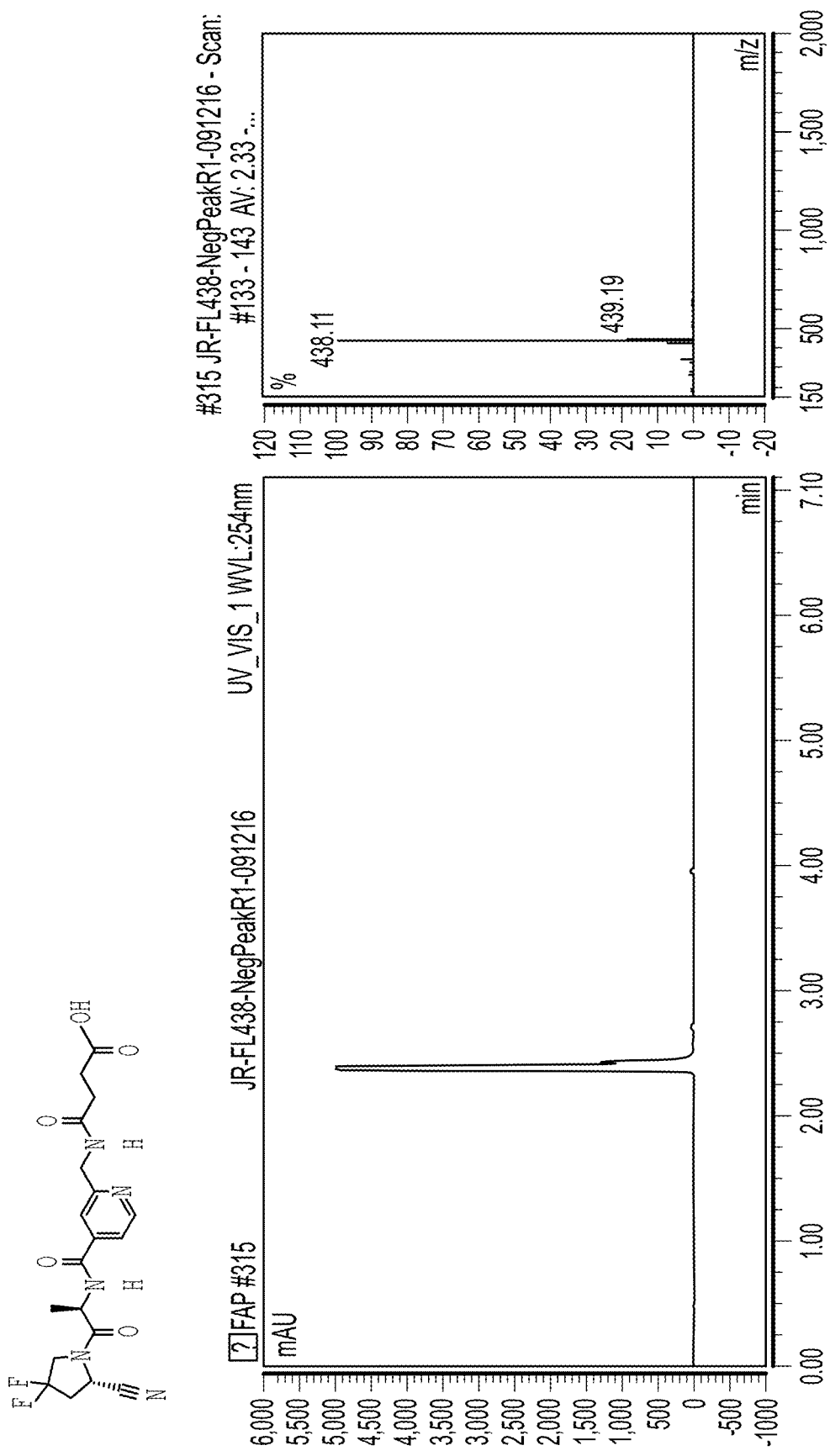
FIG. 6 shows the chemical structure and an LC/MS trace for Compound 10.

Compound 10. To the solution of compound 8 in anhy. DMF was added, compound 9 (1 eq), HATU (1 eq) and DIPEA (10 eq). The reaction mixture was stirred under argon atmosphere for 6 h. The completion of reaction was monitored by LC/MS. The crude compound 10 was purified by using RP-HPLC [A=2 Mm ammonium acetate buffer (pH 7.0), B=acetonitrile, solvent gradient 0% B to 80% B in 35 min] to yield the requisite product. LRMS-LC/MS (m/z): [M+H]⁺ calcd for $C_{19}H_{21}F_2N_5O_5$, 437.4; found 438. LC/MS trace of Compound 10 is shown in FIG. 6.

Figure 7:
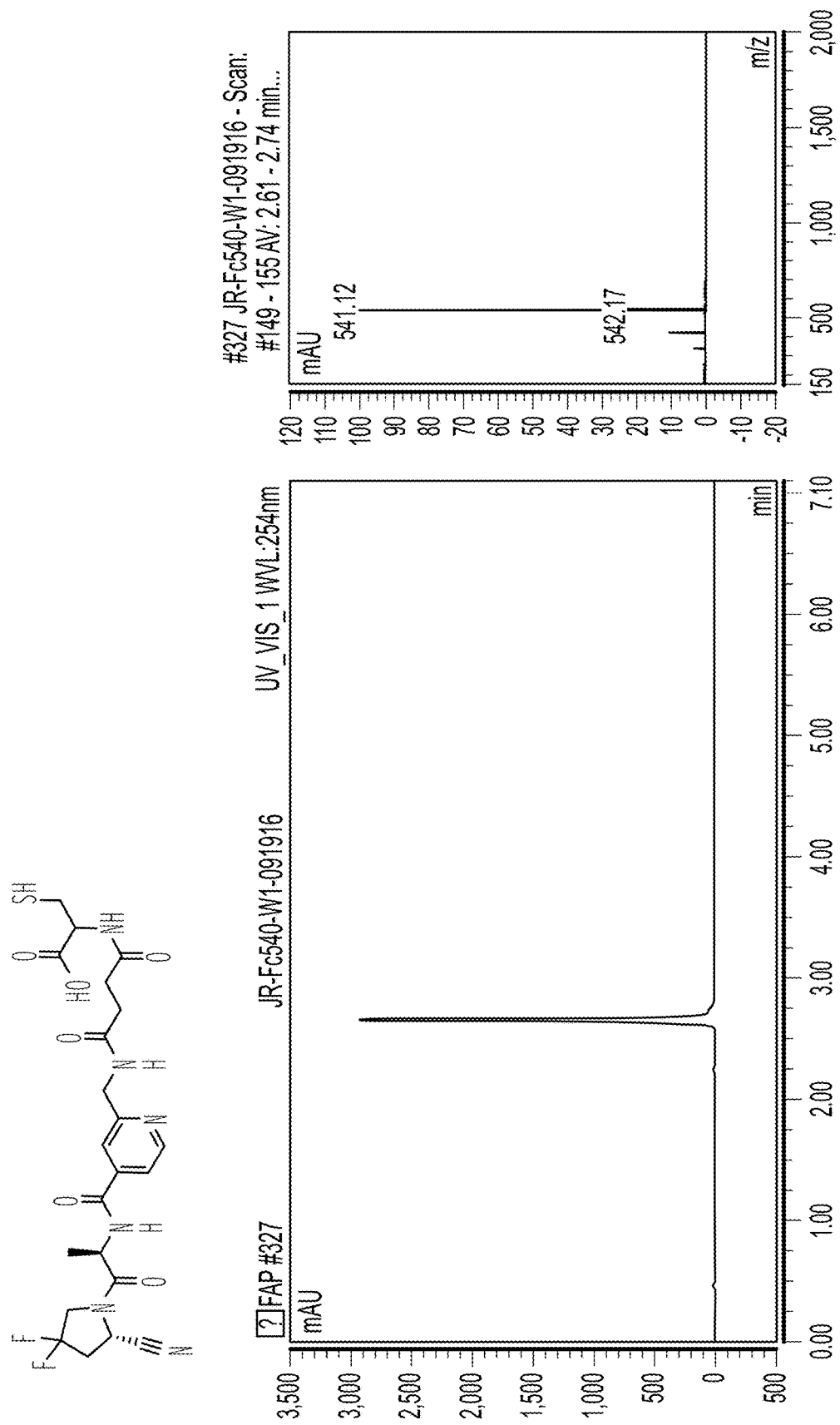
FIG. 7 shows the chemical structure and an LC/MS trace for JFL-L1.

Synthesis of JFL-L1 As described in scheme 2, the compound was prepared by solid phase peptide synthesis. PyBop, Anhy. DMF, Anhy. DIPEA, compound 10, and the H-Cys(Trt)2-chlorotrityl resin were combined at room temperature. The final product was cleaved from the resin using the standard cocktail solution of TFA:Water:TIPS: Ethanedithiol (95%: 2.5%: 2.5%: 2.5%). Crude JFL-L1 was purified by using RP-HPLC [A=2 Mm ammonium acetate buffer (pH 5.0), B=acetonitrile, solvent gradient 0% B to 80% B in 35 min] to yield the requisite product. LRMS-LC/MS (m/z): [M+H]⁺ calcd for $C_{22}H_{26}F_6N_6O_6S$, 540.54; found 541. LC/MS trace of JFL-L1 is shown in FIG. 7.

Figure 8:
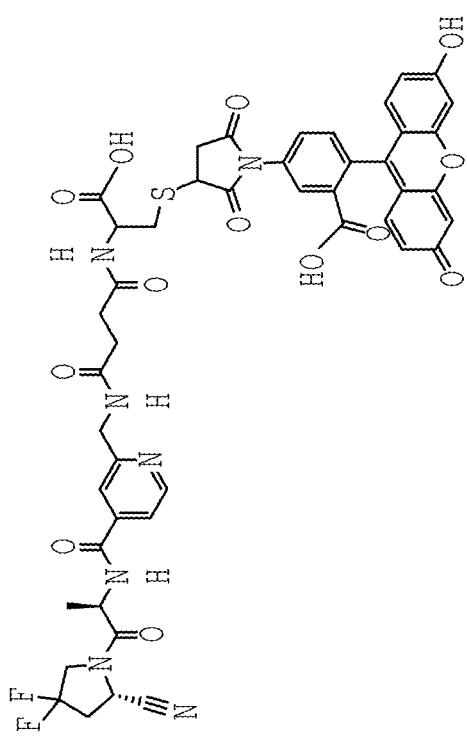
FIG. 8 shows the chemical structure and an LC/MS trace for JFL-L1-FM.
Figure 8:
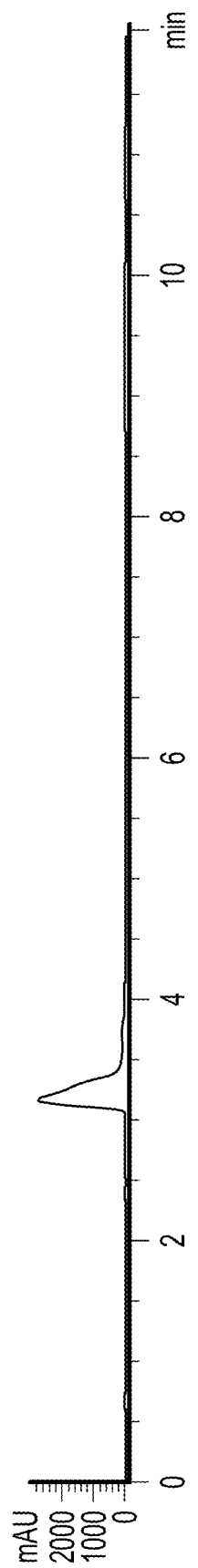
Figure 8:
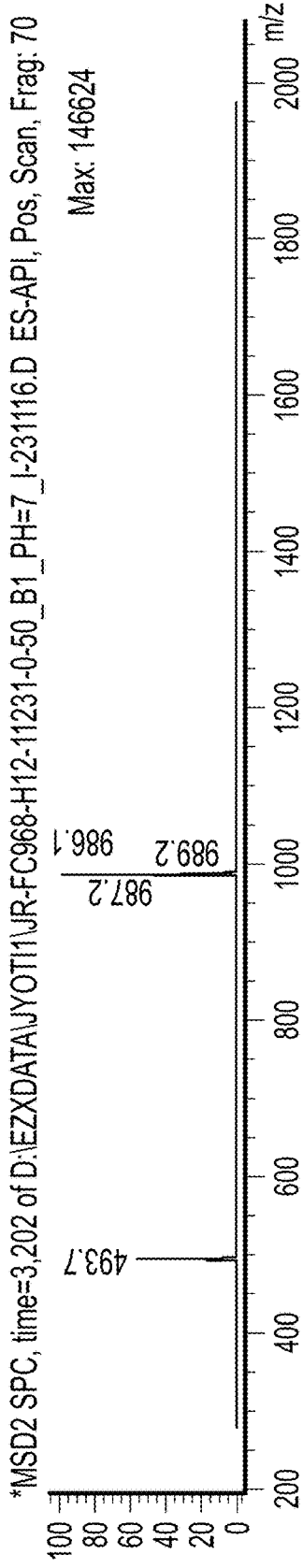
Figure 8:
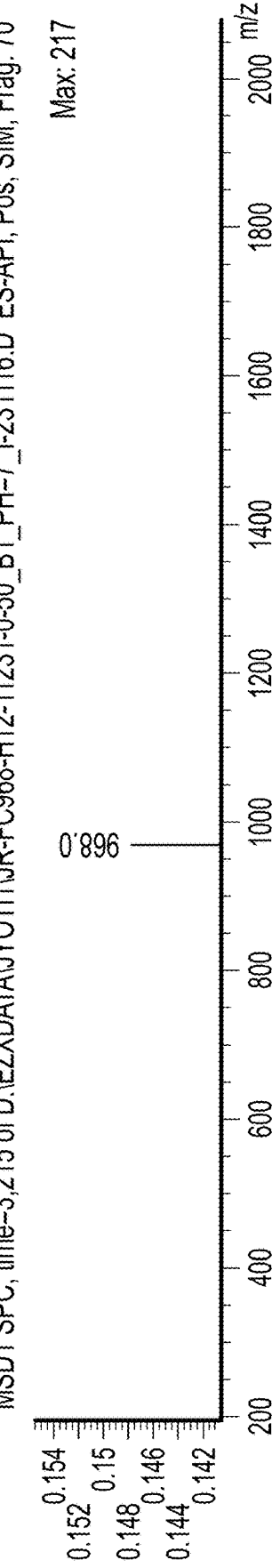
Figure 9:
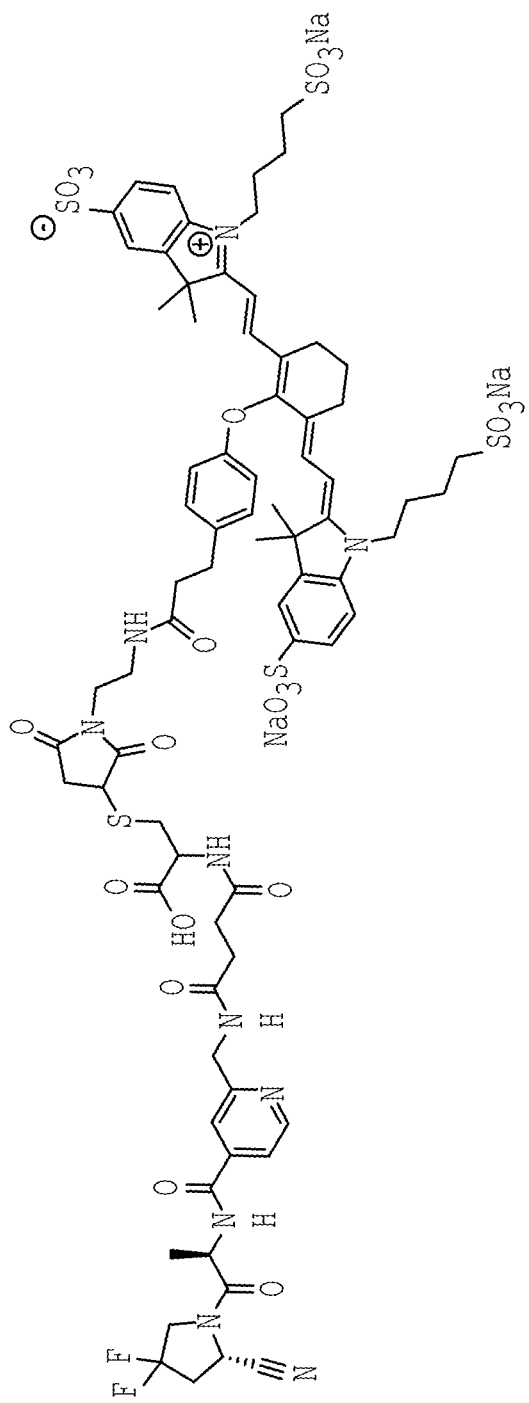
FIG. 9 shows the chemical structure and an LC/MS trace for S0456 maleimide.
Figure 9:
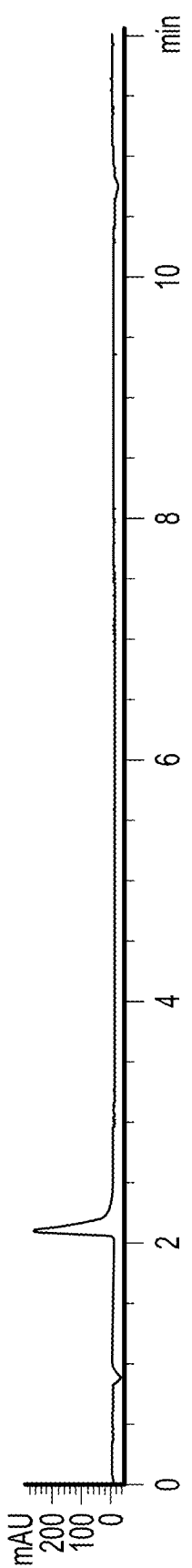
Figure 9:
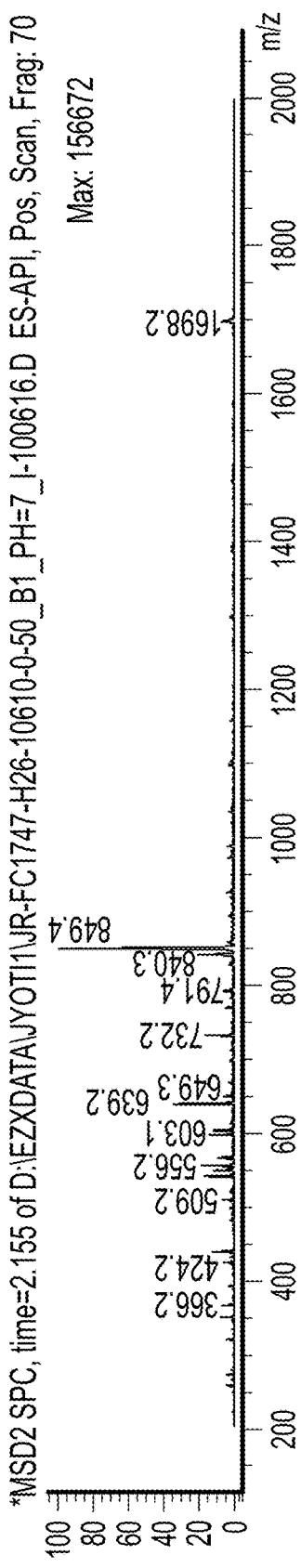
Figure 9:
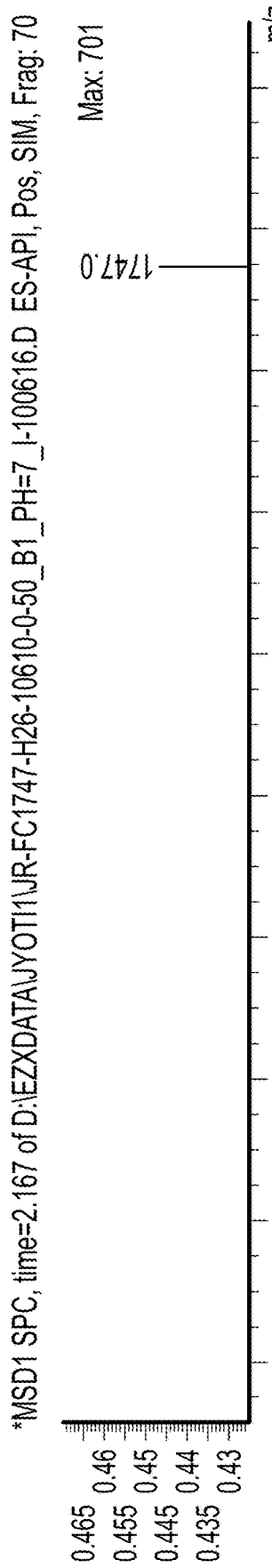

Synthesis of JFL-L1-FM and JFL-L1-S0456. JFL-L1 was dissolved in DMSO and 5 eq of DIPEA. To this reaction mixture was added either 1 eq of fluorescein maleimide or S0456 maleimide. The reaction mixture was stirred under argon atmosphere for 1 h and the completion of the reaction was monitored by LC/MS. The crude compounds JFL-L1-FM and JFL-L1-S0456 were purified by using RP-HPLC [A=2 Mm ammonium acetate buffer (pH 7.0), B=acetonitrile, solvent gradient 0% B to 80% B in 35 min] to yield the requisite product. The LCMS characterization of JFL-L1-FM and JFL-L1-S0456 are as follows. LRMS-LC/MS (m/z): [M+H]⁺ calcd for $C_{46}H_{39}F_2N_7O_{13}S$, 967.91; found 968. LRMS-LC/MS (m/z): [M+H]⁺ calcd for $C_{75}H_{85}F_2N_{10}Na_3O_{22}S_5$, 1745.82.35; found 1747. LC/MS trace of JFL-L1-FM is shown in FIG. 8. LC/MS trace of JFL-L1-S0456 is shown in FIG. 9.

Scheme 3. Synthesis of S0456 maleimide
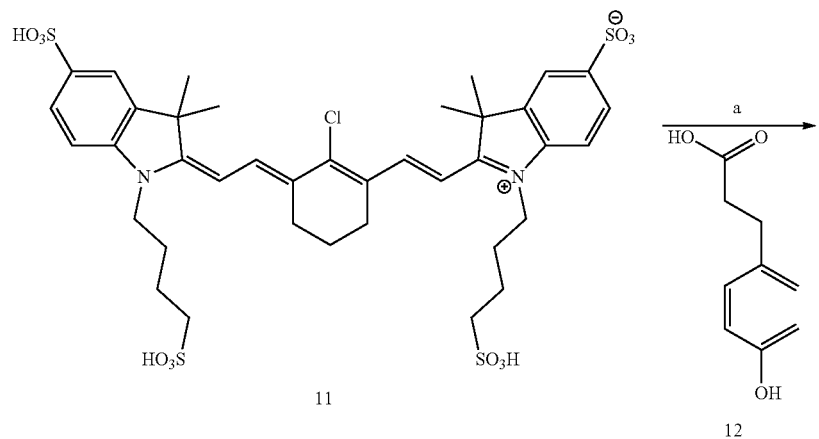
11
12
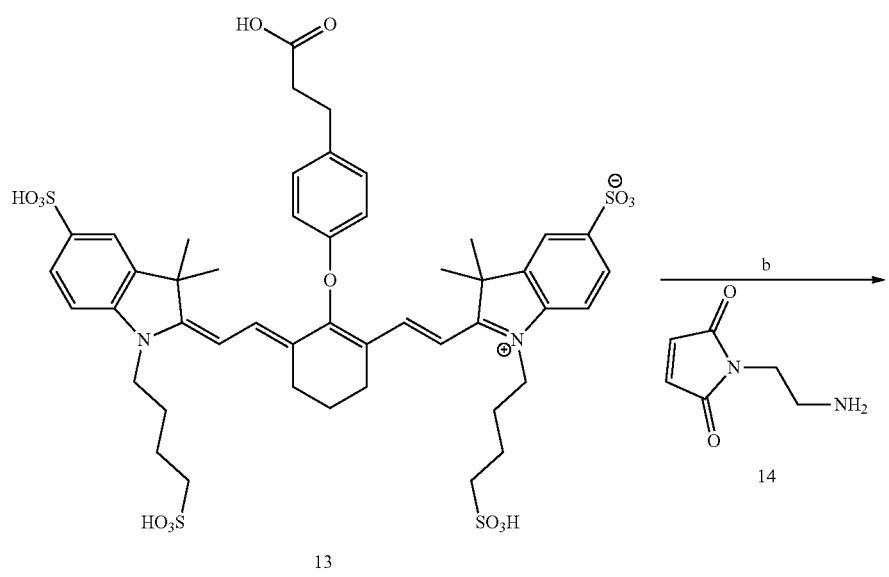
13
14
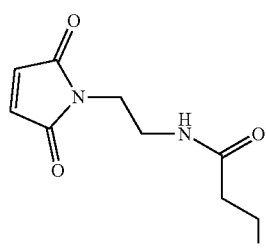

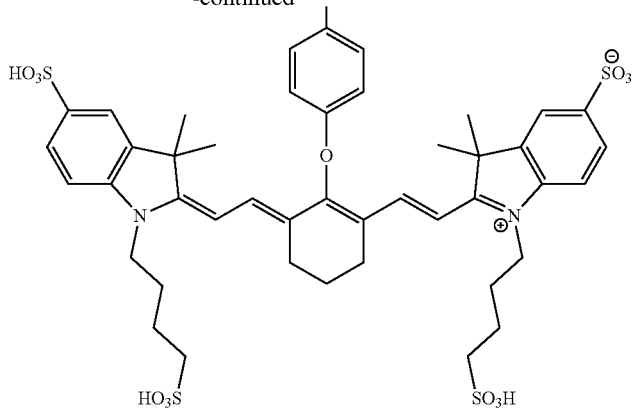

S0456 maleimide

Figure 10:
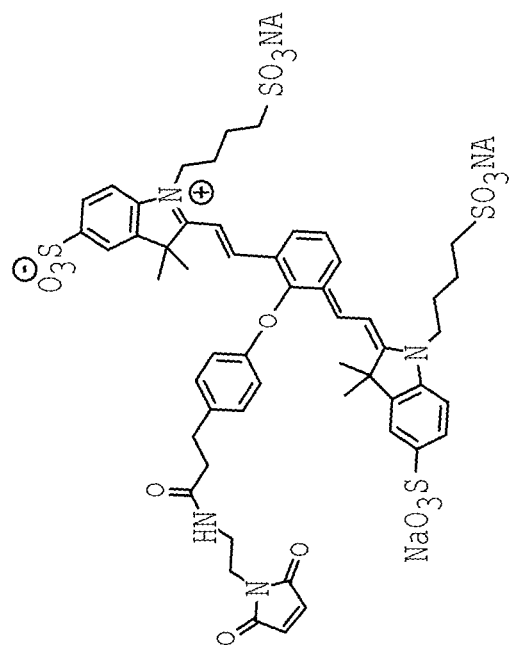
FIG. 10 shows the chemical structure and an LC/MS trace for JFL-L1-S0456.
Figure 10:
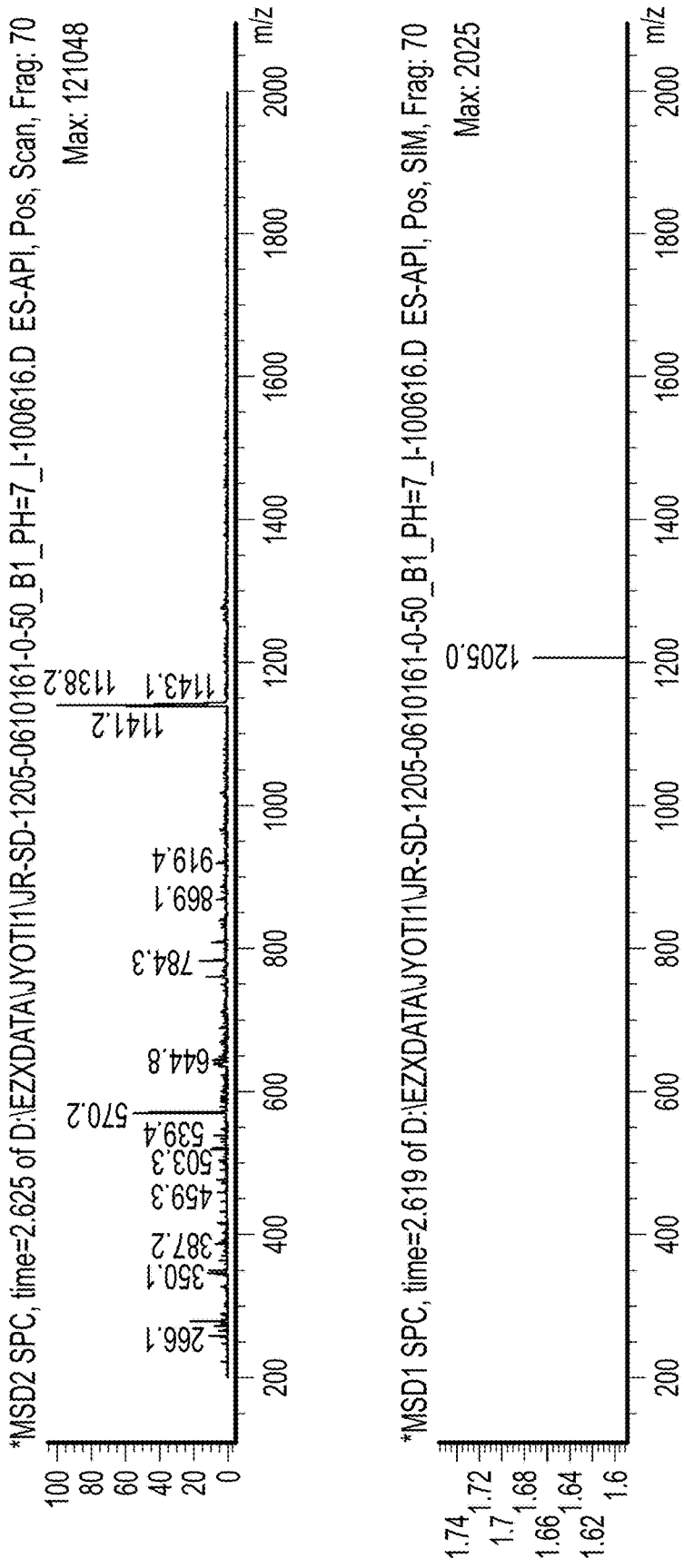

Reagents and conditions: a) KOH, H₂O, rt-100° C.; b) HATU, Anhy. DIPEA, Anhy. DMF, rt. LC/MS trace of S0456 maleimide is shown in FIG. 10, Synthesis of FAPα Targeted Tubulysin B Hydrazide Scheme 4. Synthesis of JFL-L1-TuBH

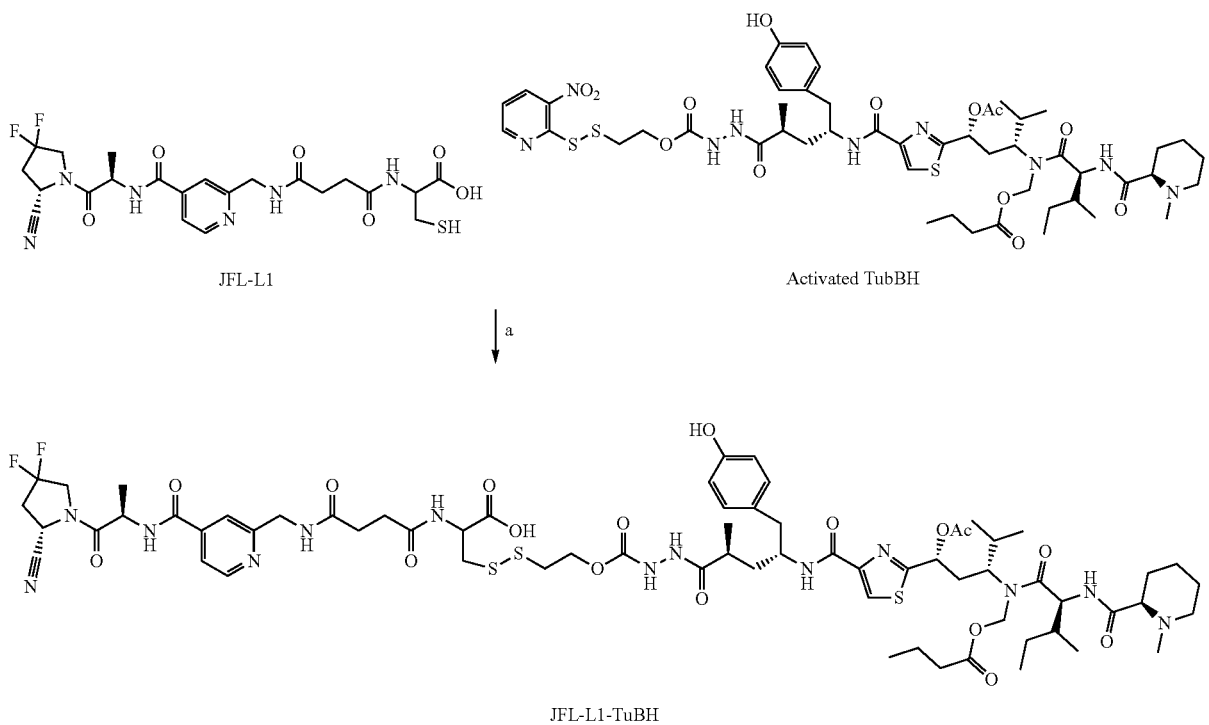

JFL-L1-TuBH

Reagents and conditions: a. (i) JFL-L1, H₂O/NaHCO₃ (pH = 7.0-7.2), Argon, r.t. (ii) activated TubBH, anhydrous THF, argon, r.t.

Figure 17:
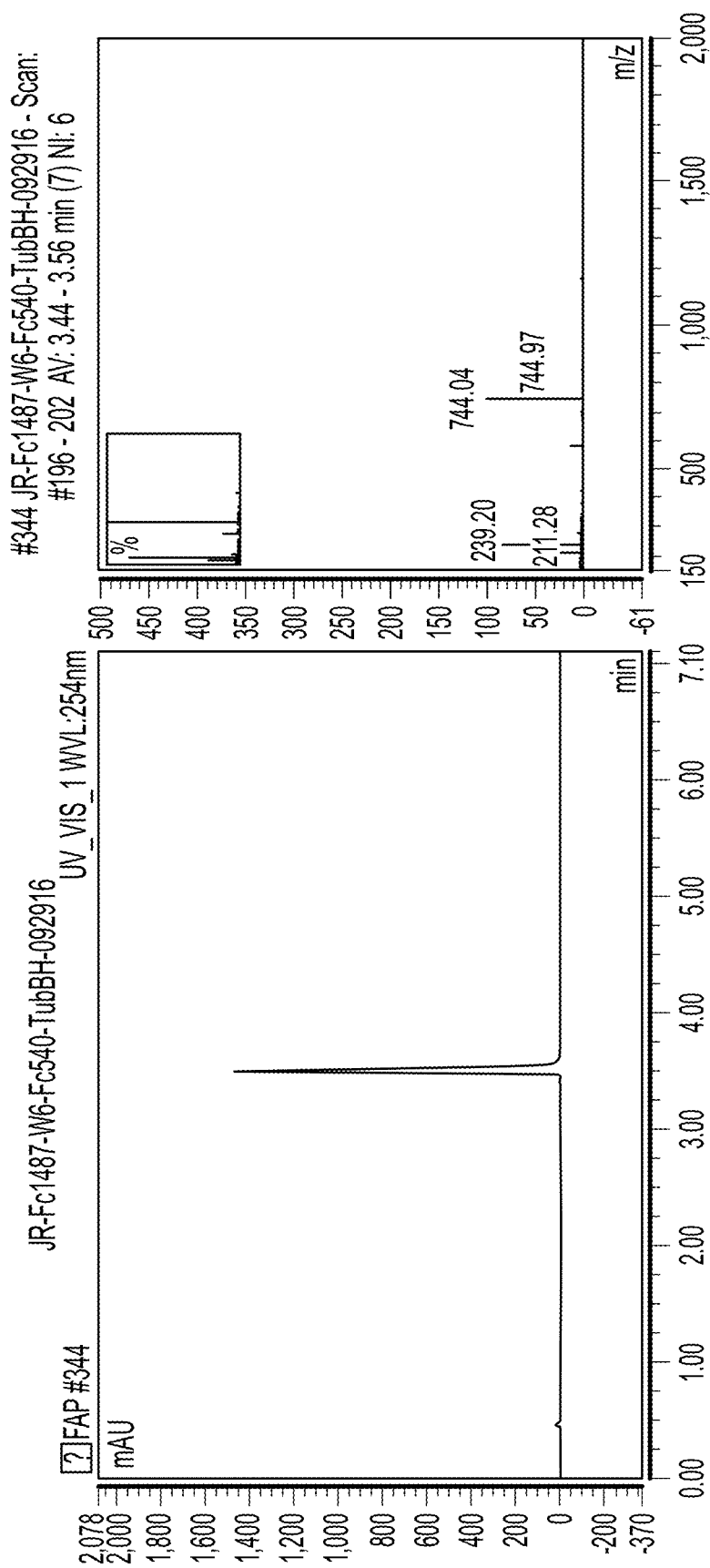
FIG. 17 shows the LC/MS trace for JFL-L1-TubBH.

FAP targeted tubulysin B hydrazide conjugate was synthesized as described below. Briefly, JFL-L1 was dissolved in argon purged HPLC grade water and adjusted to pH 7.0 using a NaHCO₃ saturated solution of the same water. Disulfide activated tubulysin B hydrazide (1 eq) in THF was added to the reaction mixture and stirred at room temperature under argon atmosphere. The progress of the reaction was monitored by analytical LRMS-LCMS. The crude product was purified by using preparative RP-HPLC [A=2 Mm ammonium acetate buffer (pH 7.0), B=acetonitrile, solvent gradient 0% B to 80% B in 35 min] to yield 95% of the desired product. LRMS-LC/MS (m/z): [M+H]⁺ calcd for $C_{67}H_{93}F_2N_{13}O_{17}S_3$, 1487; found [M/2+1] 744, as shown in FIG. 17.

Synthesis of FAP Targeted NIR Imaging: PEG and
Peptidoglycan Linker

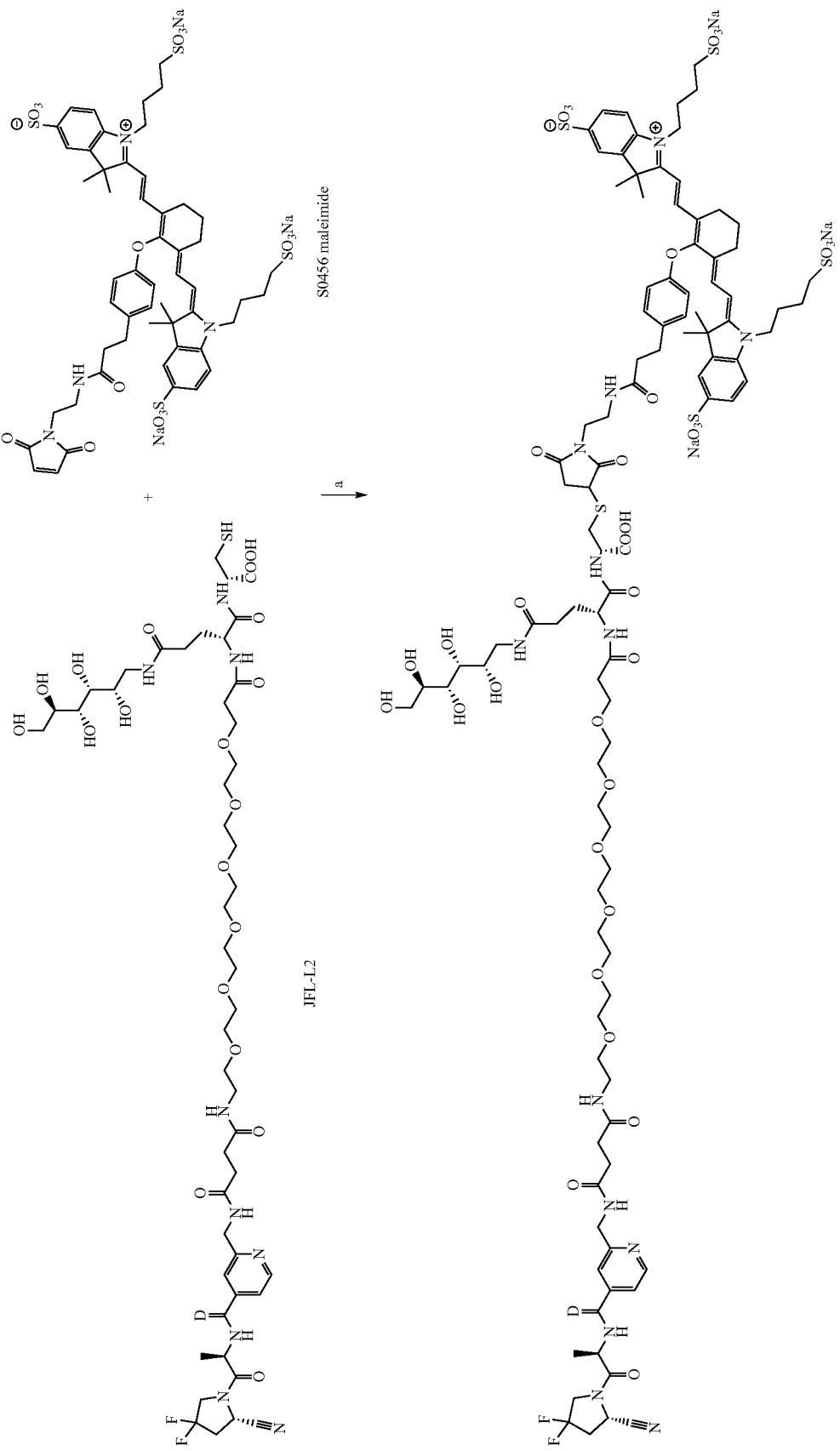

Figure 21A:
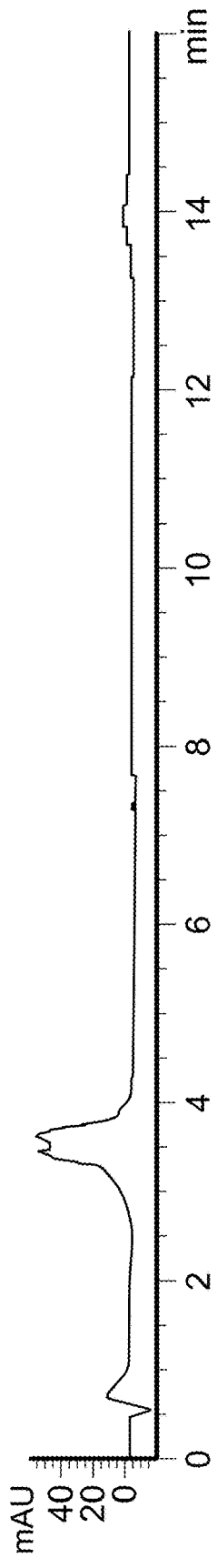
FIG. 21A-B shows the LC/MS trace for JFL-L2-S0456.

Synthesis of JFL-L2-S0456: FAP targeting ligand (JFL) was conjugated with a PEG and a peptidoglycan molecule to synthesize JFL-L2. Briefly, JFL-L2 was synthesized by standard solid phase peptides synthesis and purified by RP-HPLC as shown in FIG. 21A. LRMS-LC/MS (m/z): requisite product. LRMS-LC/MS (m/z): [M+H]+ calcd for $C_{101}H_{134}F_2N_{13}Na_3O_{36}S_5$, 2371.5; found 790.

Synthesis of JFL-L3

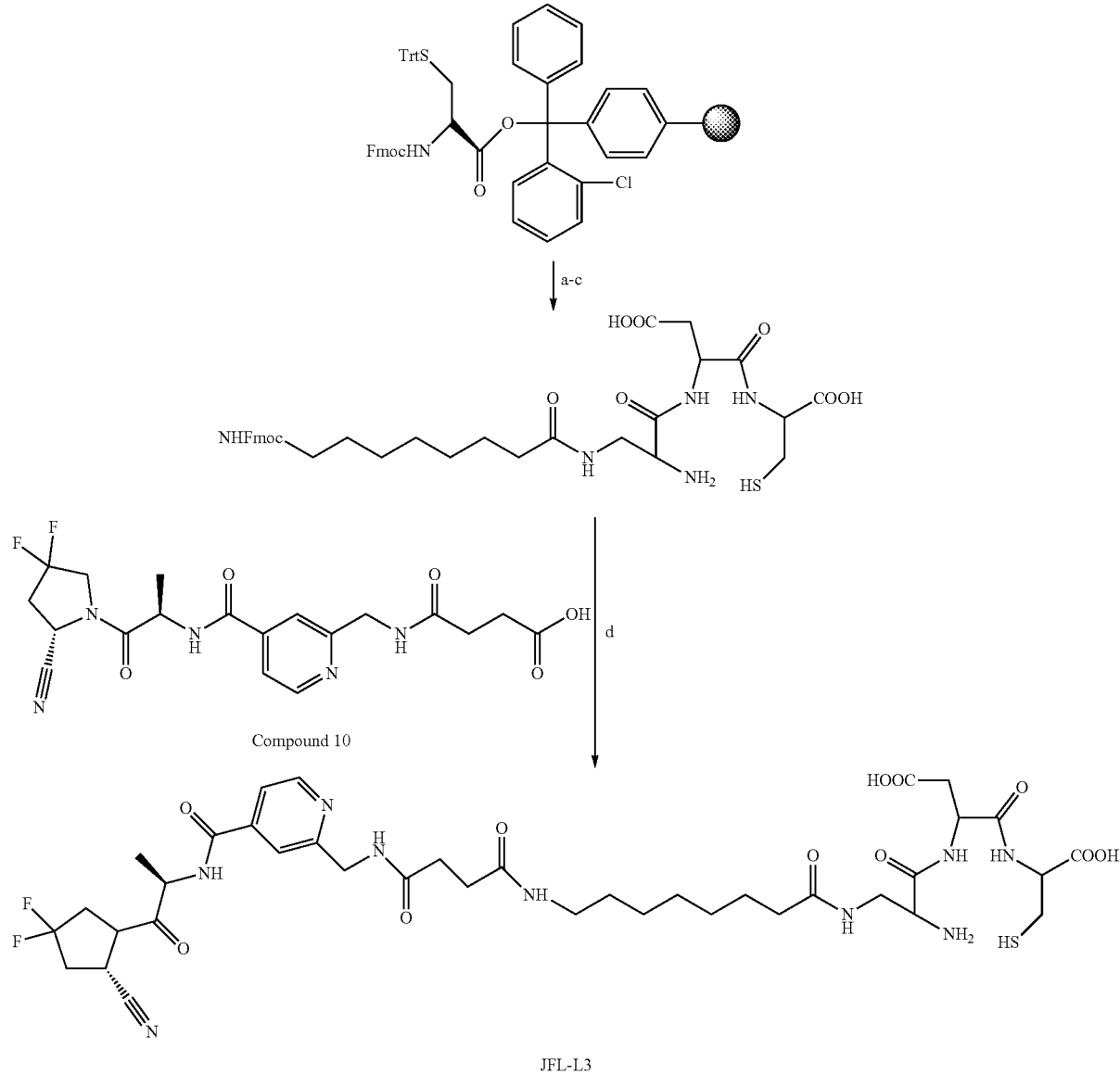

Scheme 6 Synthesis of JFL-L3,

Compound 10

JFL-L3

Reagents and conditions: (a) (i) 20% piperidine/DMF, rt, (ii) Fmoc-Asp(OtBu), PyBop, DMF, DIPEA, (b) (i) 20% piperidine/DMF, rt, 10 min (ii) Fmoc-diaminopropionic (DAP) acid, PyBop, DMF, DIPEA, (c) (i) 20% piperidine/DMF, rt, (ii) Fmoc-8-amino-octanoic acid, PyBop, DMF, DIPEA, (d) (i) 20% piperidine/DMF, rt, 10 min (ii) Compound 10, PyBop, DMF, DIPEA, (iii) TFA/H₂O/TIPS/EDT (92.5:2.5:2.5:2.5), 1 h. * The crude product was purified by using HPLC and characterized by using LC/MS.

Figure 21B:
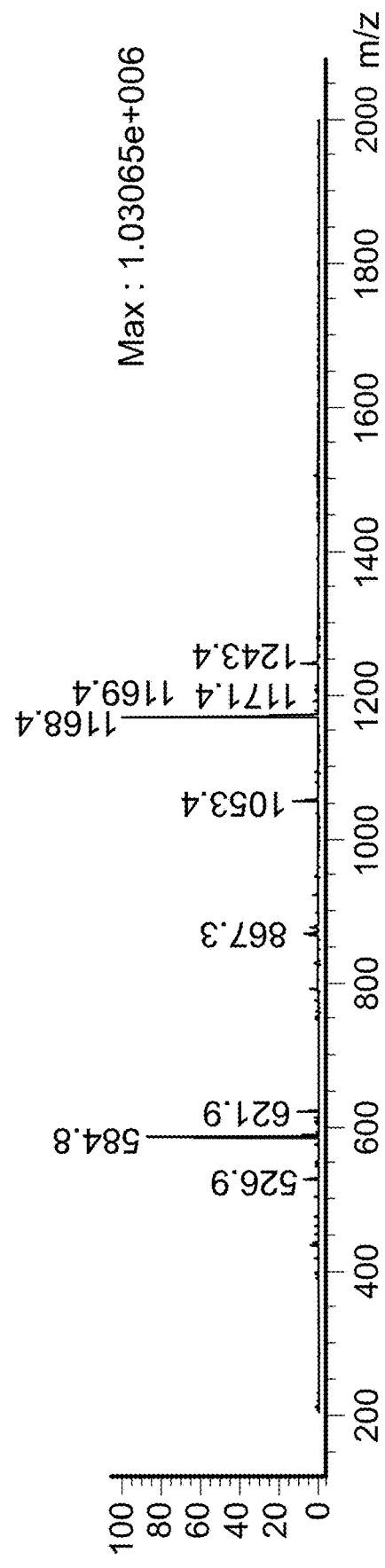
Figure 25A:
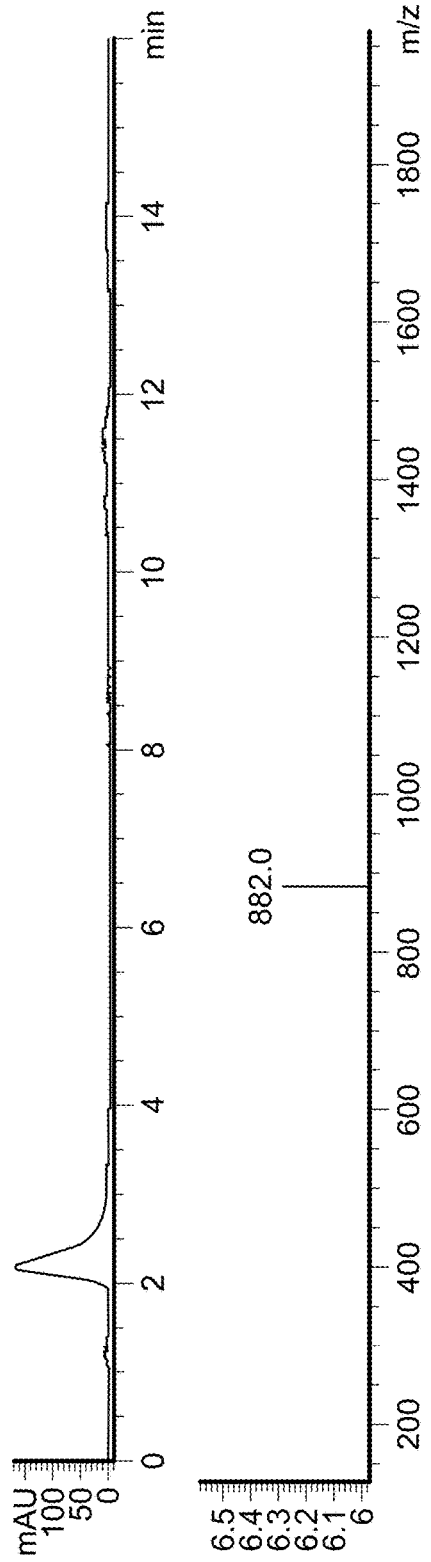
FIGS. 25A-B show the LC/MS traces for JFL-L3.

[M+H]+ calcd for $C_{48}H_{72}F_2N_9Na_3O_{20}S$, 1168; found 1169, as shown in FIG. 21B. To the reaction mixture of 1 equivalence of purified JFL-L2 and S0456-malemide in anhydrous DMSO, 5 equivalences of DIPEA was added. The reaction mixture was allowed to stir under argon atmosphere and the completion of the reaction was monitored by using LC-MS. Crude JFL-L2-S0456 was purified by using RP-HPLC [A=2 mM ammonium acetate buffer (pH 7.0), B=acetonitrile, solvent gradient 0% B to 50% B in 35 min] to yield the Synthesis of JFL-L3: As described in the scheme, the JFL-L3 was synthesized by standard solid phase peptide synthesis. All the components of the conjugate were built on the H-Cys(Trt)2-chlorotrityl resin. The standard cocktail solution of TFA:Water:TIPS:Ethanedithiol (95%: 2.5%: 2.5%: 2.5%) was used to cleave the final conjugate from the resin. Crude products were purified by using RP-HPLC [A=2 Mm ammonium acetate buffer (pH 5.0), B=acetonitrile, solvent gradient 0% B to 80% B in 35 min]

to yield the requisite product. For JFL-L3, LRMS-LC/MS (m/z): [M+H]$^+$ calcd for $C_{37}H_{52}F_2N_{10}O_{11}S$, 882.9; found 882, as shown in FIG. 25A.

Formulation of non-radioactive JFL-L3: Prior to radiolabeling with $^{99m}$Tc the JFL-L3 was formulated according to previously published procedure. Briefly, the 0.1 mg of. JFL-L3, 80 mg of sodium α-D-glucoheptonate, and 10 mg of tin (II) hydrochloride, were dissolved in argon purged water. The pH of the solution was adjusted to 6.8±0.2 with sodium hydroxide or hydrochloric acid. The final volume was adjusted to 10 ml and then transferred to 10 vials containing 1 ml each of the above solution and lyophilized. The lyophilized powder was sealed in the vials under argon and stored at −20° C.

Figure 25B:
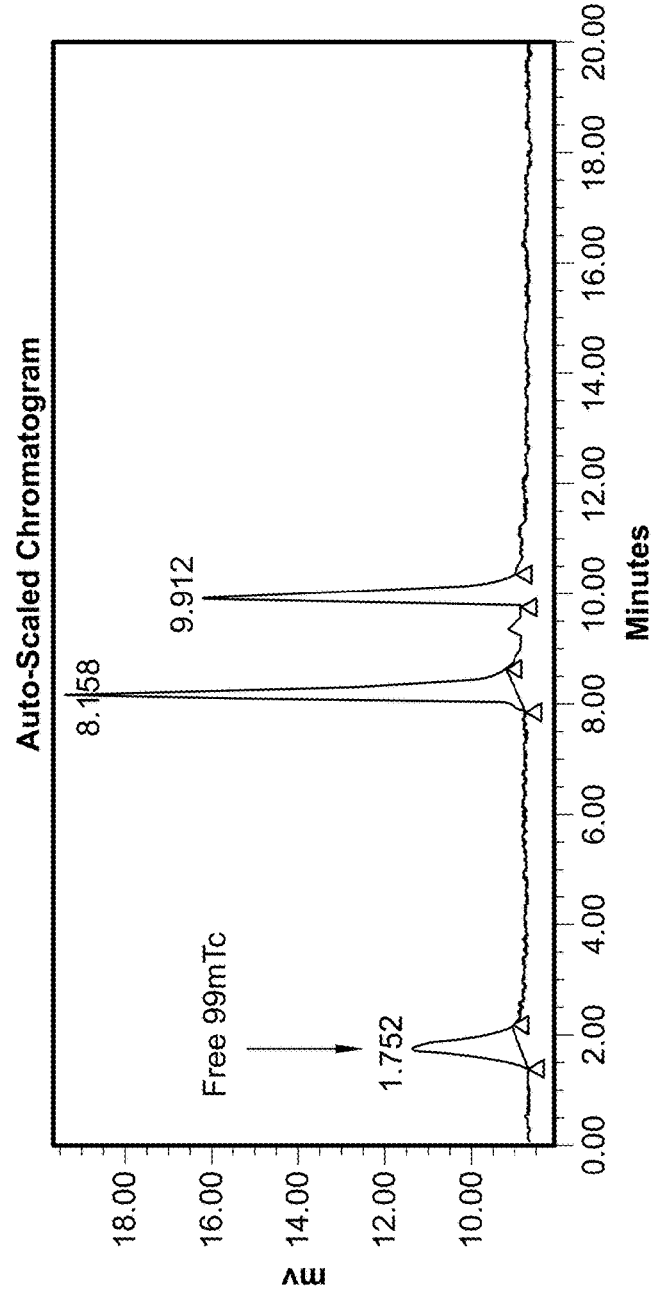

$^{99m}$Tc labelling of JFL-L3: Radiolabeling of the conjugate was performed according to the published procedure. Briefly, to a formulated vial of JFL-L3 1 ml of $^{99m}$Tc sodium pertechnetate was added and heated for ~18 min at 100° C. The chelated solution was cooled to room temperature prior to using it for in vitro and in vivo studies. The chelation efficiency of the conjugates was confirmed by radio HPLC, as shown in FIG. 25B.

Synthesis of JL-L3-S0456

Scheme 7. Synthesis of JL-L3-S0456,

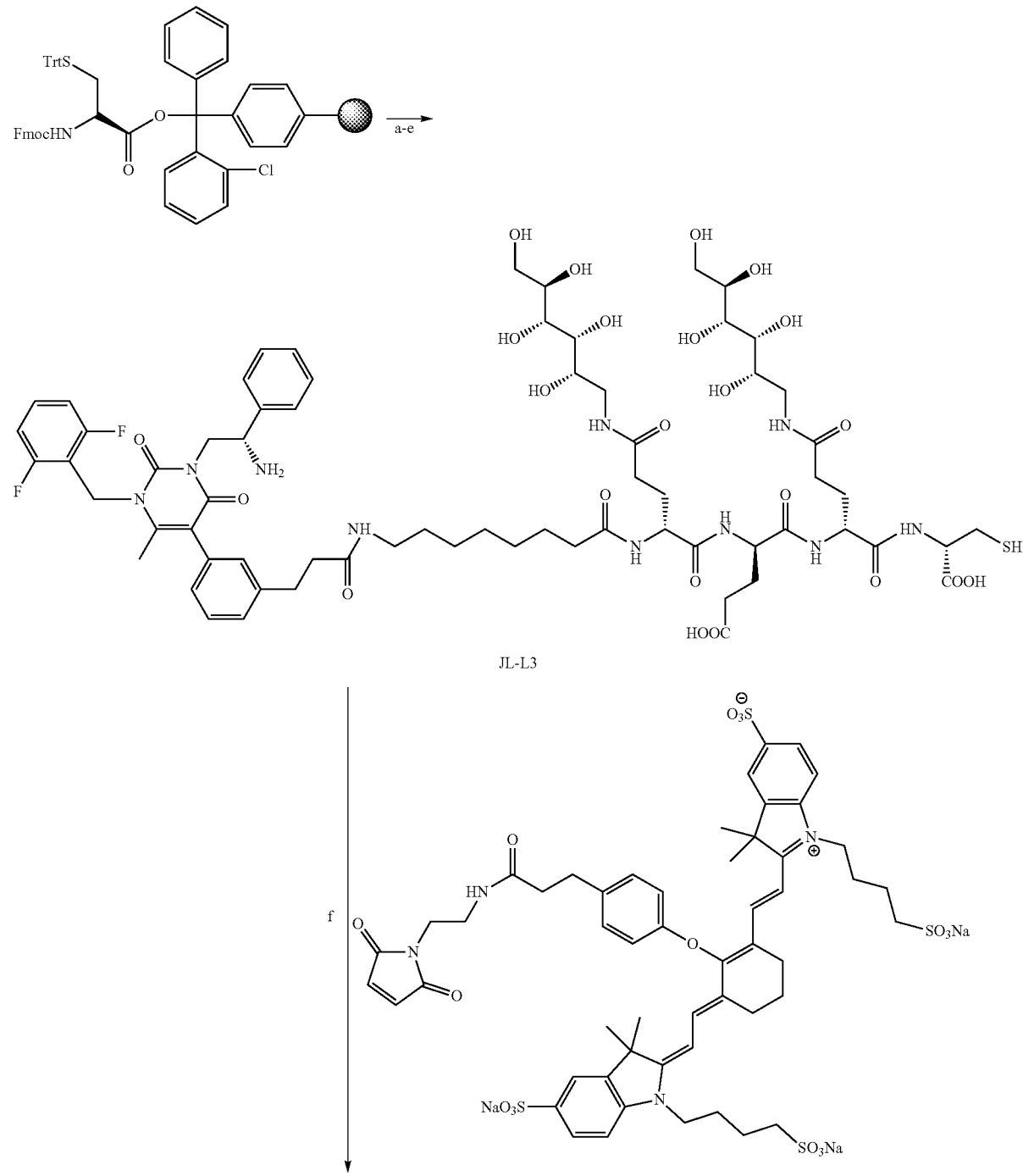

-continued

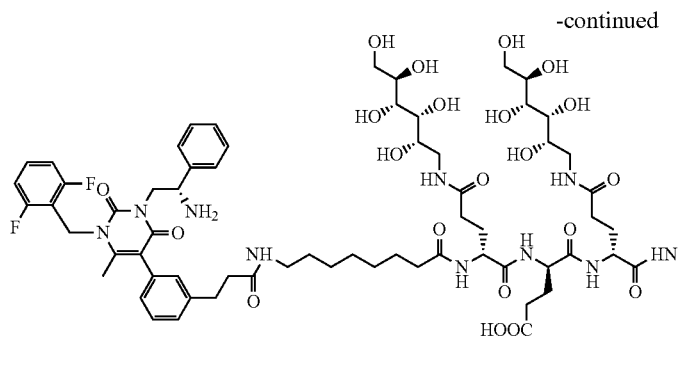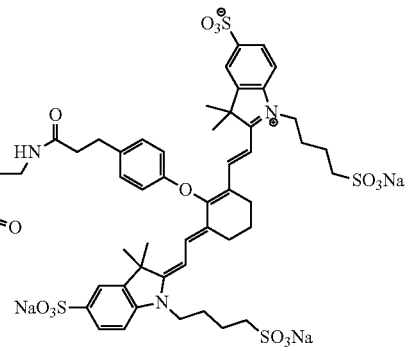

JL-L3-S0456

Reagents and conditions: (a) (i) 20% piperidine/DMF, rt, (ii) 3,4,5,6-di-isopropylidene-1-amino-deoxy(Fmoc-Glu-OH)-D-glucitol, PyBop, DMF, DIPEA, (b) (i) 20% piperidine/DMF, rt, 10 min (ii) Fmoc-Glu(OtBu)-OH, PyBop, DMF, DIPEA, (c) (i) 20% piperidine/DMF, rt, (ii) 3,4,5,6-di-isopropylidene-1-amino-deoxy(Fmoc-Glu-OH)-D-glucitol, PyBop, DMF, DIPEA, (d) (i) 20% piperidine/DMF, rt, 10 min (ii) Fmoc-8-amino-octanoic acid, PyBop, DMF, DIPEA, (e) (i) 20% piperidine/DMF, rt, 10 min (ii) JL, PyBop, DMF, DIPEA, (iii) TFA/H$_2$O/TIPS/EDT (92.5:2.5:2.5:2.5), 1 h, (f) JL-L3, S0456 maleimide, anhydrous DMSO, DIPEA, rt.

Synthesis of JL-L3: As described in Scheme 7, the linker was prepared by the standard solid phase peptide synthesis. The peptidoglycan subunit was synthesized as described elsewhere. JL was then coupled to the linker on the solid phase. The final product was cleaved from the H-Cys(Trt) 2-chlorotrityl resin using the standard cocktail solution of TFA:Water:TIPS: Ethanedithiol (95%: 2.5%: 2.5%: 2.5%). Crude JL-L3 was purified by using RP-HPLC [A=2 Mm ammonium acetate buffer (pH 5.0), B=acetonitrile, solvent gradient 0% B to 80% B in 35 min] to yield the requisite product. LRMS-LC/MS (m/z): [M+H]$^+$ calcd for $C_{67}H_{94}F_2N_{10}O_{23}S$, 1477; found 1478.

Synthesis of NIR conjugate JL-L3-S0456: S0456 dye containing the maleimide was synthesized as described in the Scheme 3. 1 equivalence of S0456-maleimide and JL-L3 were dissolved in anhydrous DMSO, followed by addition of 5 equivalences of DIPEA. The reaction mixture was stirred under argon atmosphere for 1 h. The completion of the reaction was monitored by using LC-MS. Crude JL-L3-S0456 was purified by using RP-HPLC [A=2 Mm ammonium acetate buffer (pH 7.0), B=acetonitrile, solvent gradient 0% B to 80% B in 35 min] to yield the requisite product. The LCMS characterization of JL-L3-S0456 was as follows. LRMS-LC/MS (m/z): [M+H]$^+$ calcd for $C_{120}H_{151}F_2N_{14}Na_3O_{39}S_5$, 2680.85; found 2682.

Method Examples

Cell Culture. The cancer cells FaDu, HT29, MDA-MB231, and KB cells were cultured in a medium consisting RPMI 1640, 10% FBS, 1% penicillin-streptomycin, 1% 2 mM glutamine at 37° C. in a 5% CO2 and 95% humidified atmosphere. HEK 293 cells were transfected to generate HEK293-FAP. The FAP positive cells were cultured in DMEM medium supplemented with 2 μl/ml of puromycin, 10% FBS, 1% penicillin-streptomycin. 1% 2 mM glutamine at 37° C. in a 5% CO2 and 95% humidified atmosphere.

Confocal Microscopy. FaDu, HT29, MDA-MB231 and KB cancer cells (30,000) were plated on 4 well confocal plate. The cells were incubated with 100 mM JFL-L1-FM and incubated for 1 h. The unbound fluorescence was removed by washing the cells three times with the medium. The cell bound fluorescence was observed by using Olympus confocal microscopy.

In Vitro Binding Assay. 100,000 HEK293-FAP cells were seeded in an amine coated 24 well plate. The cells were allowed to grown as a monolayer over 24 h and incubated with various concentrations of the JFL-L1-S0456 either in the presence or absence of excess of JFL-L1. After incubating for 1 h the cells were washed three times with medium to remove to unbound fluorescence. The cells were dissolved in 1% SDS and the cell bound fluorescence was measured by using a fluorimeter.

Animal Husbandry. 5-6 weeks old female athymic nu/nu mice were purchased from Harlan Laboratories. The animals had access to normal rodent chow and water ad libitum. The animals were housed in standard 12 h light-dark cycles. All animal procedures were approved by the Purdue Animal Care and Use Committee.

In Vivo Fluorescence Imaging and Biodistribution. For the development of subcutaneous tumor xenografts, MDA-MB231, OVCAR-3 and HEC-1B 5×10$^6$ cells in 0.2 ml sterile PBS were injected subcutaneously in the right hind flank of the female nu/nu mice. Tumor imaging was initiated once the tumor volume reached between 200 mm$^3$ and 300 mm$^3$. Each tumor-bearing mouse was intravenously injected (via tail vein) with 10 nanomoles of fluorescence dye conjugate either in the presence or absence of a 100-fold excess of the unlabeled conjugate. Animals were euthanized two hours post injection using CO$_2$ and the images were acquired using Caliper IVIS Luminal II. After performing the whole body image, the organs of interest were harvested and imaged to inspect the accumulation of the fluorescence in these organs. The image acquisition parameters were as follows: i) lamp level-high, ii) excitation-745 nm, iii) emission-ICG, iv) binning (M) 4M, (v) f-stop-4, (vi) FOV-12.5, (vii) acquisition time, 5 s.

Figure 11:
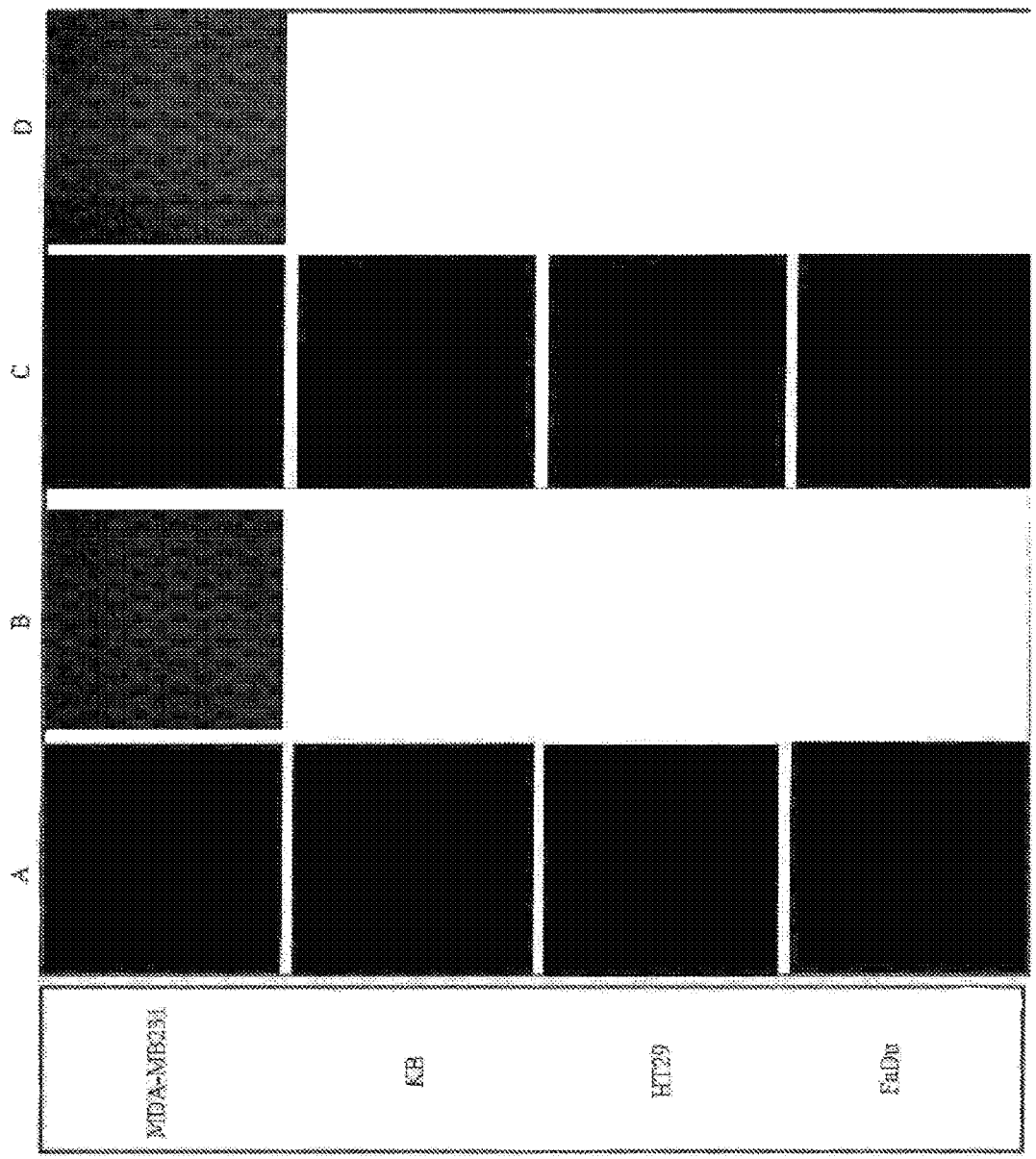
FIG. 11 shows in vitro confocal imaging results with JFL-L1-FM.

In Vitro Binding Affinity and Confocal Imaging. The cancer cells FaDU, HT29, MDA-MB231 and KB were investigated for the expression of FAP. For this purpose, the cancer cells were seeded on a confocal well plate and incubated with 100 nM of the FAP targeted FM conjugate (JFL-L1-FM) After 1 h incubation at 37° C. the cells were washed to remove any excess of the un were observed under confocal microscopy to investigate any uptake of the dye, as shown in FIG. 11. In all the four cell types no uptake of dye conjugate was observed. This implied absence of FAP on these cancer cells.

Figure 12:
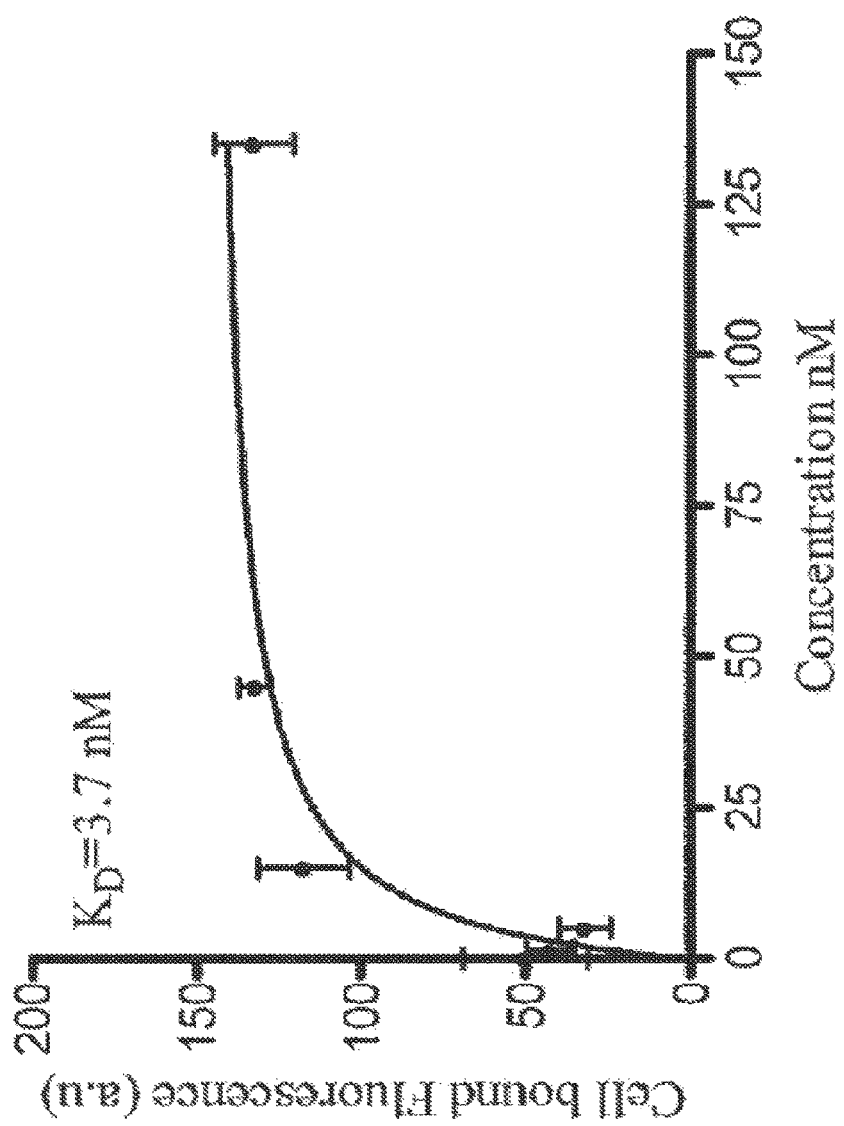
FIG. 12 shows in vitro binding affinity of JFL-L1-S0456FAP transfected HEK293 cells as determined by fluorescence vs. concentration.

To find the binding affinity of the FAP targeted NIR dye conjugate (JFL-L1-S0456), the FAP transfected HEK293 cells were plated on amine coated 24 well plate and incubated with various concentrations of the dye conjugate either in the presence or absence of excess of the FAP ligand JFL. After 1 h of incubation cells were washed to remove any excess of the unbound dye. The cells were dissolved in 1% SDS followed by quantification of cell bound fluorescence using a fluorimeter. To quantify the fluorescence, the samples were excited at 745 nm and measuring the emission of 790 nm. Cell bound fluorescence was plotted against various concentrations by using the Graph pad prism to find the apparent $K_D$ value, as shown in FIG. 12. The apparent dissociation constant of JFL-L1-S0456 was about 3.5 nM. When incubated with NIR dye conjugate in the presence of excess of JFL the cell bound fluorescence was competed indicating the uptake of JFL-L1-S0456 was FAP mediated.

Figure 13:
FIG. 13 shows in vivo imaging of JFL-L1-S0456 in FaDu mouse xenografts.
Figure 13:
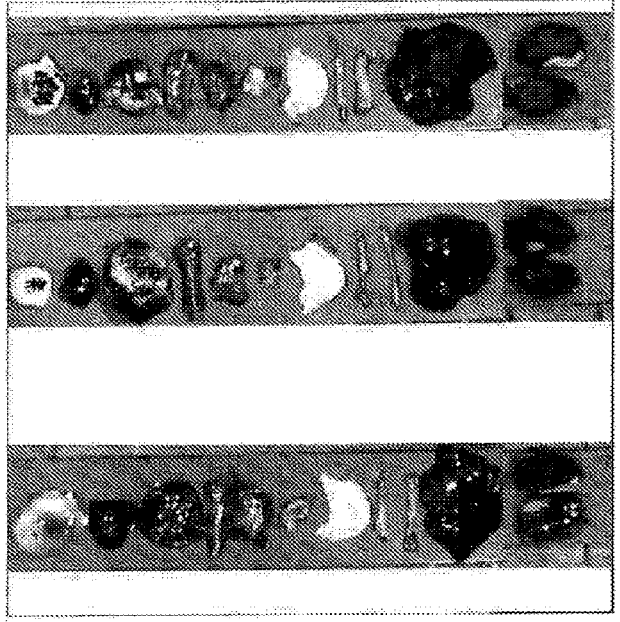
Figure 13:
Figure 13:
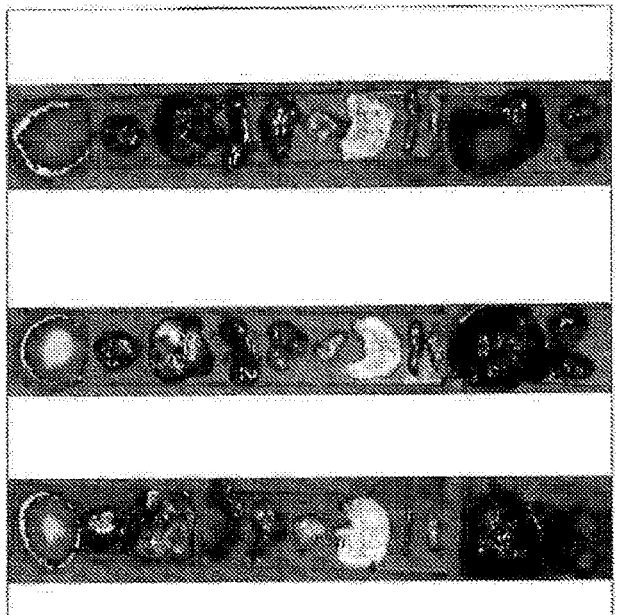
Figure 14:
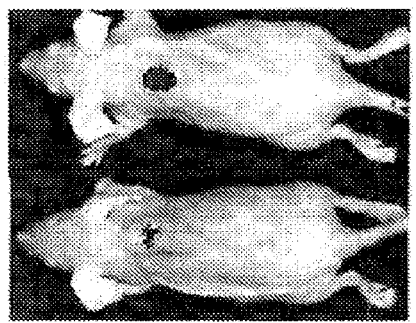
FIG. 14 shows in vivo imaging of JFL-L1-S0456 in KB mouse xenografts.
Figure 14:
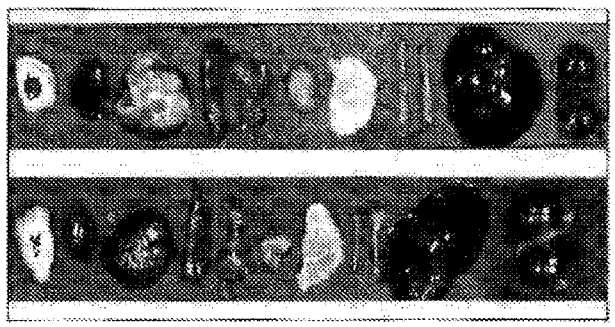
Figure 14:
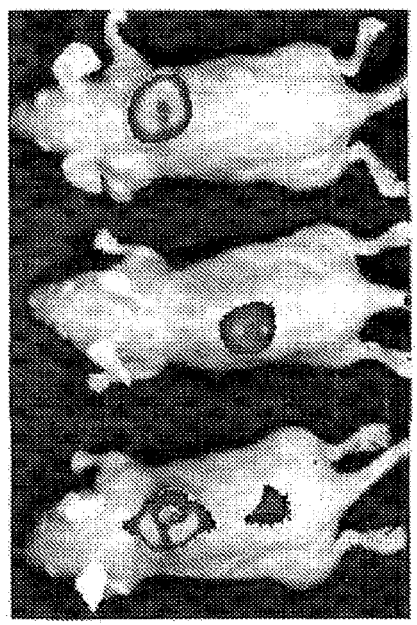
Figure 14:
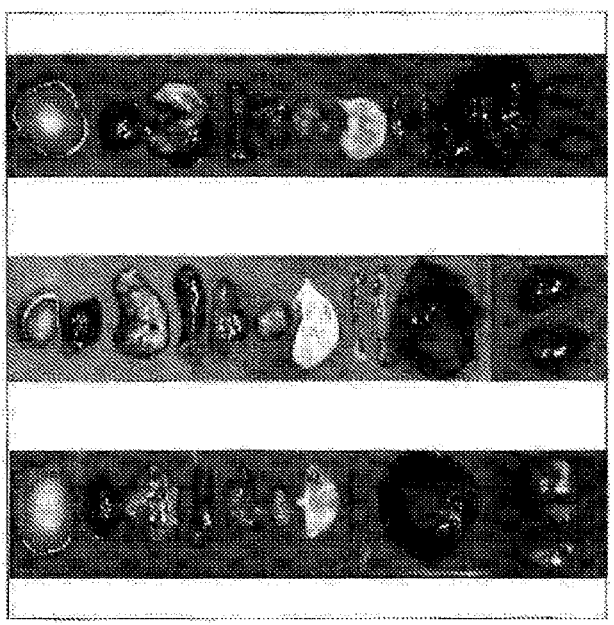
Figure 15:
FIG. 15 shows in vivo imaging of JFL-L1-S0456 in HT29 mouse xenografts.
Figure 15:
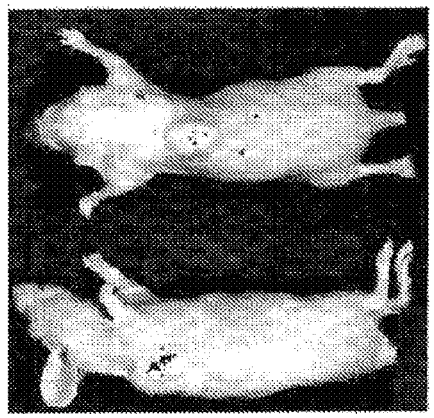
Figure 15:
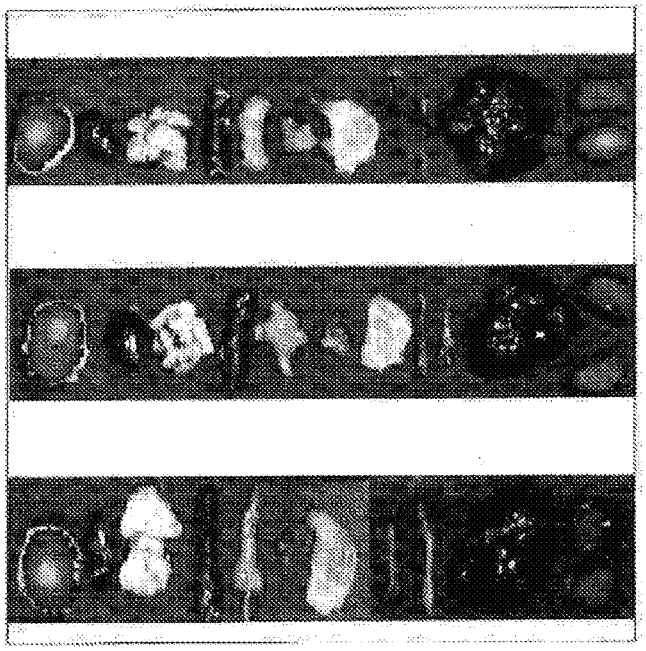
Figure 15:
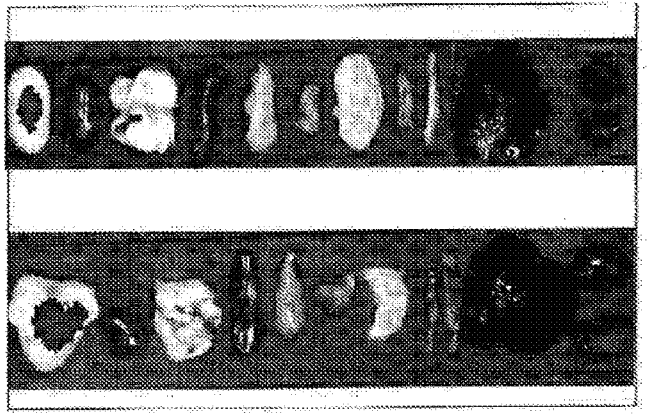
Figure 16:
FIG. 16 shows in vivo imaging of JFL-L1-S0456 in MDA-MB231 mouse xenografts.
Figure 16:
Figure 16:
Figure 16:
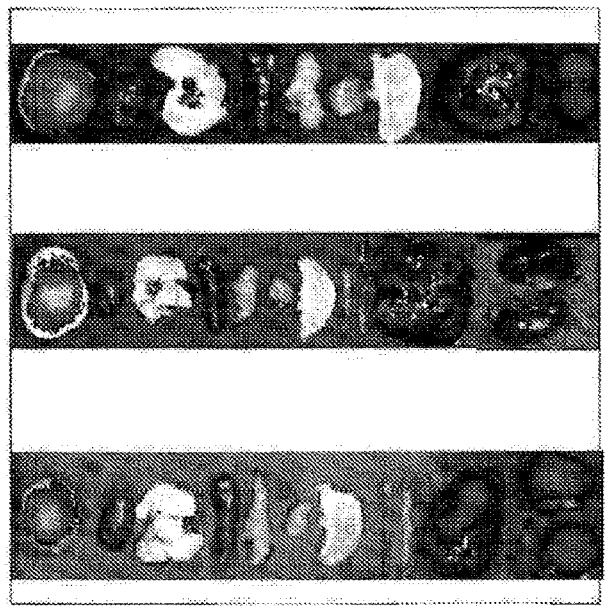

In Vivo Fluorescence Imaging. To investigate the ability of JFL-L1-S0456 to accumulate in vivo mice were implanted with FaDu (n=5), HT29 (n=5), MDA-MB231 (n=5) or KB (n=5) cells. These tumor bearing mice were intravenously injected with the NIR dye conjugate alone or co-injected with excess of the FAP targeting ligand JFL. After 2 h post injection the mice were euthanized and imaged, as shown in FIGS. 13A and 13B (FaDu), FIGS. 14A and 14B (KB), FIGS. 15A and 15B (HT29), and FIGS. 16A and 16B (MDA-MB231). FAP mediated uptake of the dye conjugate was observed in all the tumor types and excess of JFL was able to compete the fluorescence in the tumor. To inspect the uptake of the dye conjugate in other organs necropsy was performed to harvest the organs and imaged, as shown in FIGS. 13C and 13D (FaDu), FIGS. 14C and 14D (KB), FIGS. 15C and 15D (HT29), and FIGS. 16C and 16D (MDA-MB231) (organs from top to bottom: tumor, heart, lungs, spleen, pancreas, muscle, stomach, small intestine, large intestine, liver, and kidney). In addition to tumor a minimal or no uptake of the dye conjugate was observed in the liver and kidney. The uptake in these organs was not receptor mediated and was largely due to excretion of the conjugate via renal or hepatic route. Without intending to be bound by theory, since the cancer cells are FAP negative the in vivo uptake of the NIR dye conjugate is expected to be as a consequence of accumulation in the cancer-associated fibroblast which are known to express FAP. When tested in vivo, the FAP-targeted dye conjugate showed FAP mediated uptake in the tumor. Other organs (kidney and liver) showed either minimal or no uptake of the near-infrared dye conjugate.

Figure 18A:
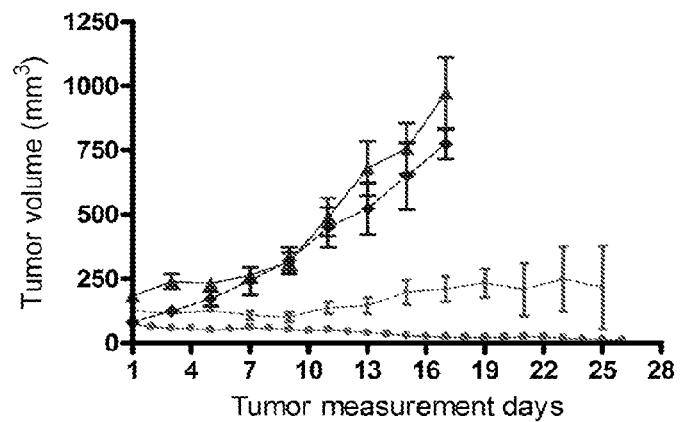
FIG. 18A shows tumor volume over time in response to treatment with JFL-L1-TubBH and FIG. 18B shows body weight of the mice used in the experiment. (▲) Control; (♦) FAP-competition; (-) Consecutive days—FAP-TubBH (40 nmoles); (●) daily FAP-TubBH (40 nmoles).
Figure 18B:
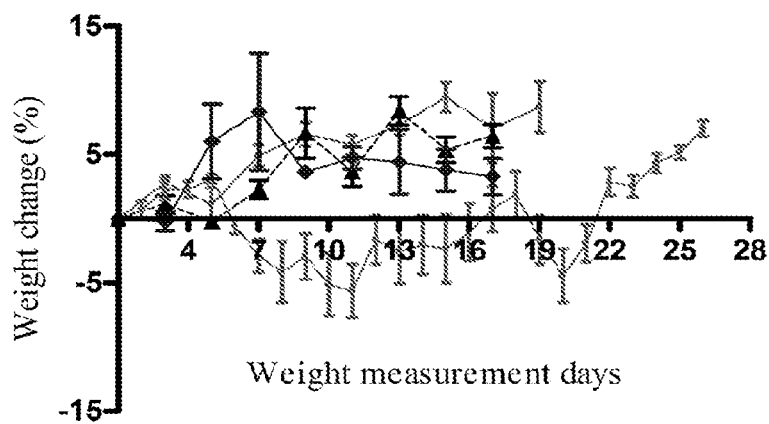

In vivo therapy study MDA-MB231: 5-6 weeks old female nu/nu athymic nude mice were subcutaneously injected with 5 million breast cancer cells (MDA-MB-231) into their shoulders. Tumors were measured in two perpendicular directions either daily or every other day during the treatment with Vernier calipers, and their volumes were calculated as $0.5 \times L \times W^2$, where L is the longest axis (in millimeters), and W is the axis perpendicular to L (in millimeters). Once the tumor volume reached ~100 mm³ the mice were randomly divided into various groups and the treatment was initiated. Dosing solutions were prepared in sterile saline and injected intravenously via tail vein. Mice in control group were injected with sterile saline whereas mice in treatment arms were injected with 40 nmoles of JFL-L1-TubBH either daily or every other day. In addition to receiving 40 nmoles of JFL-L1-TubBH the mice in competition group were also administered with 100-fold excess of the FAP-targeted ligand conjugated to the linker (JFL-L1), as shown in FIG. 18A. Mice were weighed as a measure of gross toxicity at each dosing, as shown in FIG. 18B.

To investigate the in vivo efficacy of FAP targeted Tubulysin conjugate MDA-MB-231 tumor xenografts were treated with JFL-L1-S0456. During the therapy period the mice in control and competition arm did not show any reduction in tumor volume. In the treatment arm mice were dosed with 40 nmoles of JFL-L1-TubBH and divided into two separate groups depending on the frequency of the administration of the therapeutic agents. When compared to control and competition group mice in both the therapy groups showed significant decrease in tumor volume. Mice which were treated with JFL-L1-TubBH every other day did not show complete response rather a delayed tumor growth was observed. On the other hand when the mice were treated with same dose of JFL-L1-TubBH daily, a complete response was observed. Throughout the study weight of the mice were monitored as a measure of gross toxicity. Mice in saline, completion and treatment group that received JFL-L1-TubBH every other day did not show any decrease in weight. The mice which were treated with the FAP targeted tubulysin displayed an approximately 5% reduction in weight but the same mice gained the weight towards the end of the treatment.

In Vivo Combination Therapy with FAP Targeted TubBH and Folate Targeted PI3Kinase Inhibitor or TLR7 Agonist 4-5-week-old Female BALB/c mice were injected with 100,000 4T1 cells close to the mammary fat pad. Once the tumor volume reached ~100 mm³ the mice were randomly divided into various groups and treatment was initiated. Dosing solutions of FAP targeted tubulysin B hydrazide conjugate (JFL-L1-TubBH), folate targeted PI3Kinase inhibitor (FA-PI3K), and folate targeted TLR7 antagonist (FA-TLR7) were prepared in sterile saline and injected intravenously via tail vein. The mice in control group were administered with sterile saline whereas mice in treatment group either received the JFL-L1-TubBH or FA-PI3K or FA-TLR7 alone or in combination with one of the other agents (JFL-L1-TubBH, FA-PI3K, or FA-TLR7). The concentration of single dose used for the treatment were 20 nmoles of JFL-L1-TubBH. 10 nmoles of FA-PI3K and 10 nmoles of FA-TLR7. Mice were injected with the test agents daily followed by tumor volume measurement (caliper). As a measure of gross toxicity, body weight of the mice was also monitored at each dosing. Mice in FAP competition group received FAP targeted tubulysin B hydrazide in the presence of excess of the FAP ligand, JFL.

Figure 19A:
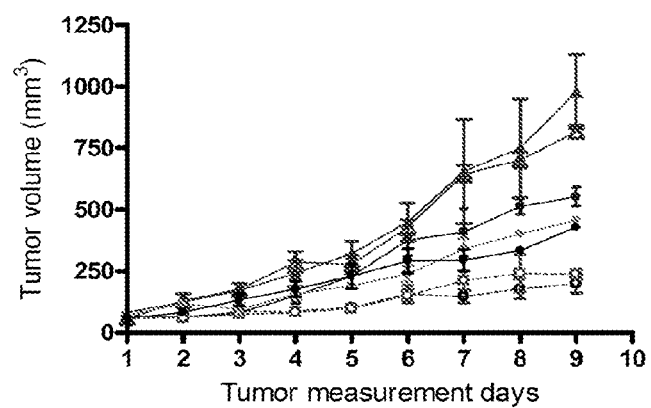
FIG. 19A shows tumor volume over time in response to JFL-L1-TubBH and JFL-L1-TubBH in combination with other treatments.
Figure 19B:
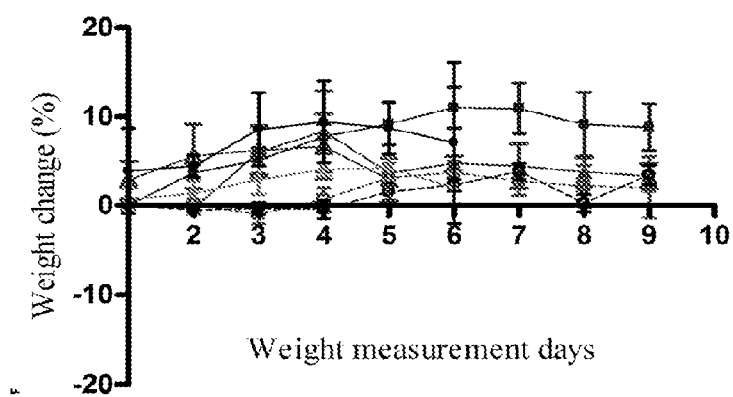
FIG. 19B shows the body weight of the mice used in the experiment. (Δ) Control; (▲) FAP-competition; (■) FAP-TubBH; (▼) Folate-TLR7; (●) Folate-PI3K; (□) FAP-TubBH & Folate-TLR7; (○) FAP-TubBH & Folate-PI3K.

4T1 tumor bearing mice in control and competition (FAP-competition) group did not show any reduction in tumor volume, as shown in FIG. 19A. Compared to these two group mice treated with single agent either FAP targeted tubulysin B hydrazide (JFL-L1-TubBH) or folate targeted PI3Kinase inhibitor (FA-PI3K) or TLR7 antagonist (FA-TLR7) delayed the tumor growth. To investigate the effect of combination therapy of FAP and folate targeted chemotherapeutic agents mice in combination therapy arm were divided into two different groups. One of the group received JFL-L1-TubBH in combination with FA-TLR whereas mice in the other group received FA-PI3K along with JFL-L1-TubBH. When compared to the single agent treatment both the combination therapy showed a decrease in tumor volume that was additive. Throughout the therapy weight of the mice were monitored as a measure of gross toxicity. None of the group exhibited any weight loss, as shown in FIG. 19B.

In vivo FAP targeted CAR T-cell therapy: MDA-MB-231 subcutaneous tumor was developed in female NSG mice by injecting 5 million cancer cells. Once the tumor volume reached ~100 mm$^3$ the mice were randomized into three different groups and treatment was initiated. Mice in all the groups were administered with 15 million CAR T-cells which has an scFv domain that binds specifically and tightly with fluorescein. 2 h after administration of the CAR T-cells mice in all the groups were given the first dose of the respective test agents. Mice in the control group were injected with sterile saline whereas mice in treatment arm were either injected with JFL-L1-FM (10 nmoles) alone or in combination with 100-fold excess of FAP ligand, JFL. During therapy, mice in different groups were administered with the respective test agents intravenously on every other day. As a measure of gross toxicity mice were also weighed at every dosing.

Figure 20A:
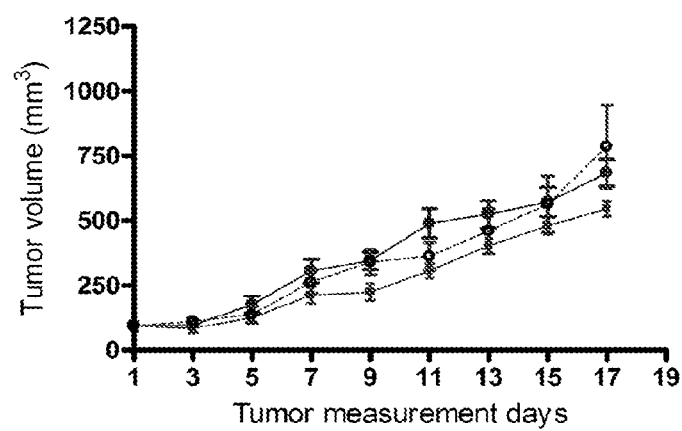
FIG. 20A shows tumor volume over tie in response to JFL-L1-FM and FIG. 20B shows the body weight of the mice used in the experiment. (○) Control; (■) FAP-FM; (●) FAP-competition.
Figure 20B:
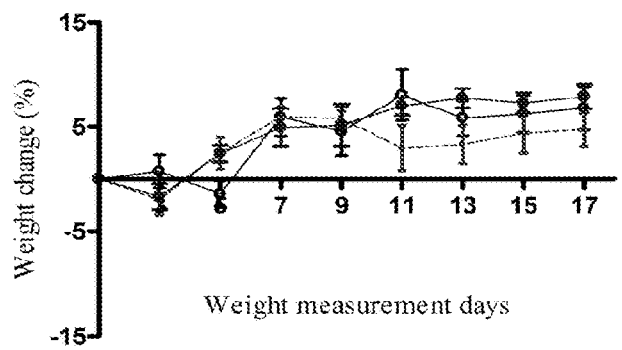

MDA-MB-231 mice xenograft models were utilized to investigate the effect of CAR T-cell with an scFV domain that recognizes the fluorescein fragment of the FAP targeted FM conjugate (JFL-L1-FM). The mice in control and competition group did not show any difference in the tumor growth rate, as shown in FIG. 20A. At the beginning of the study mice treated with CAR T-cell and FAP targeted FM (JFL-L1-FM) did not display any reduction in tumor volume. But after 1 week of treatment slight separation in the tumor growth rate was observed. No weight loss was observed in any of the arms of the study, as shown in FIG. 20B. The results suggests that FAP targeted CAR T-cell therapy has the potential to kill the tumor but the dose of CAR T-cell and JFL-L1-FM needs to be optimized to induce tumor suppression earlier in the treatment.

In vivo Imaging with JFL-L2-S0456: MDA-MB-231 tumor bearing athymic female mice were injected with 5 nmoles of JFL-L2-S0456 intravenously. Mice were euthanized 2 h post-injections using $CO_2$ and the images were acquired using IVIS Lumina II. After completion of whole body imaging the organs were harvested and further imaged to examine the accumulation of the JFL-L2-S0456 in these organs.

Figure 22A:
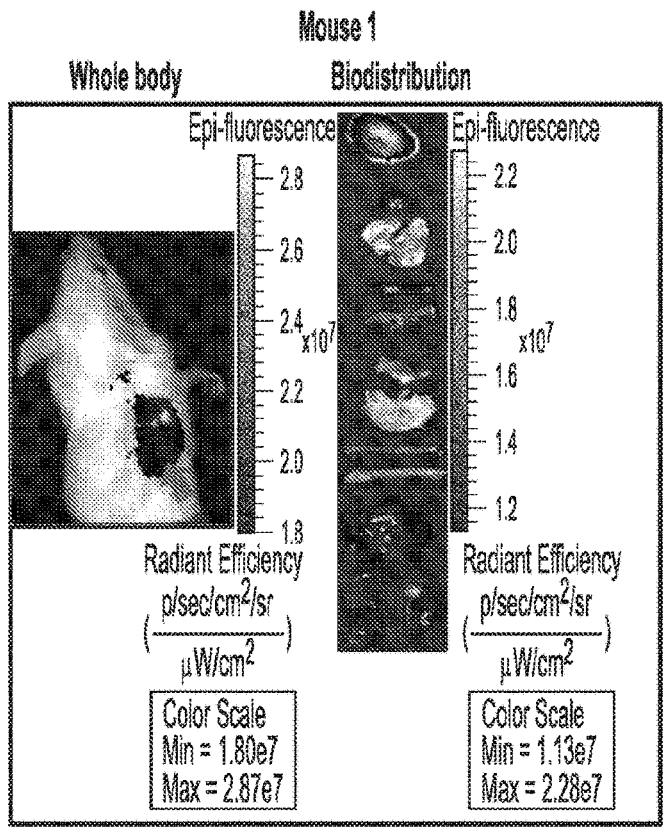
FIGS. 22A-C show in vivo imaging with JFL-L2-S0456.
Figure 22B:
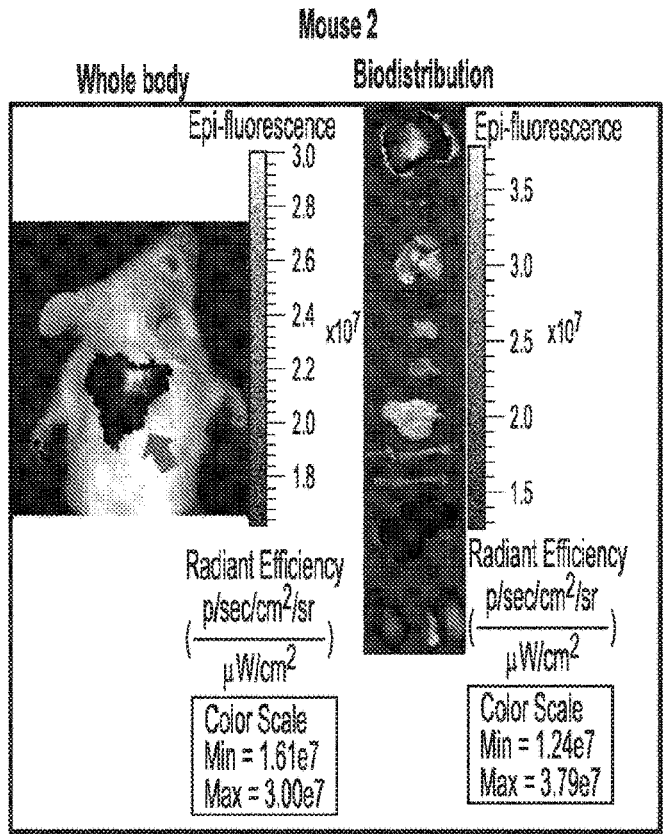
Figure 22C:
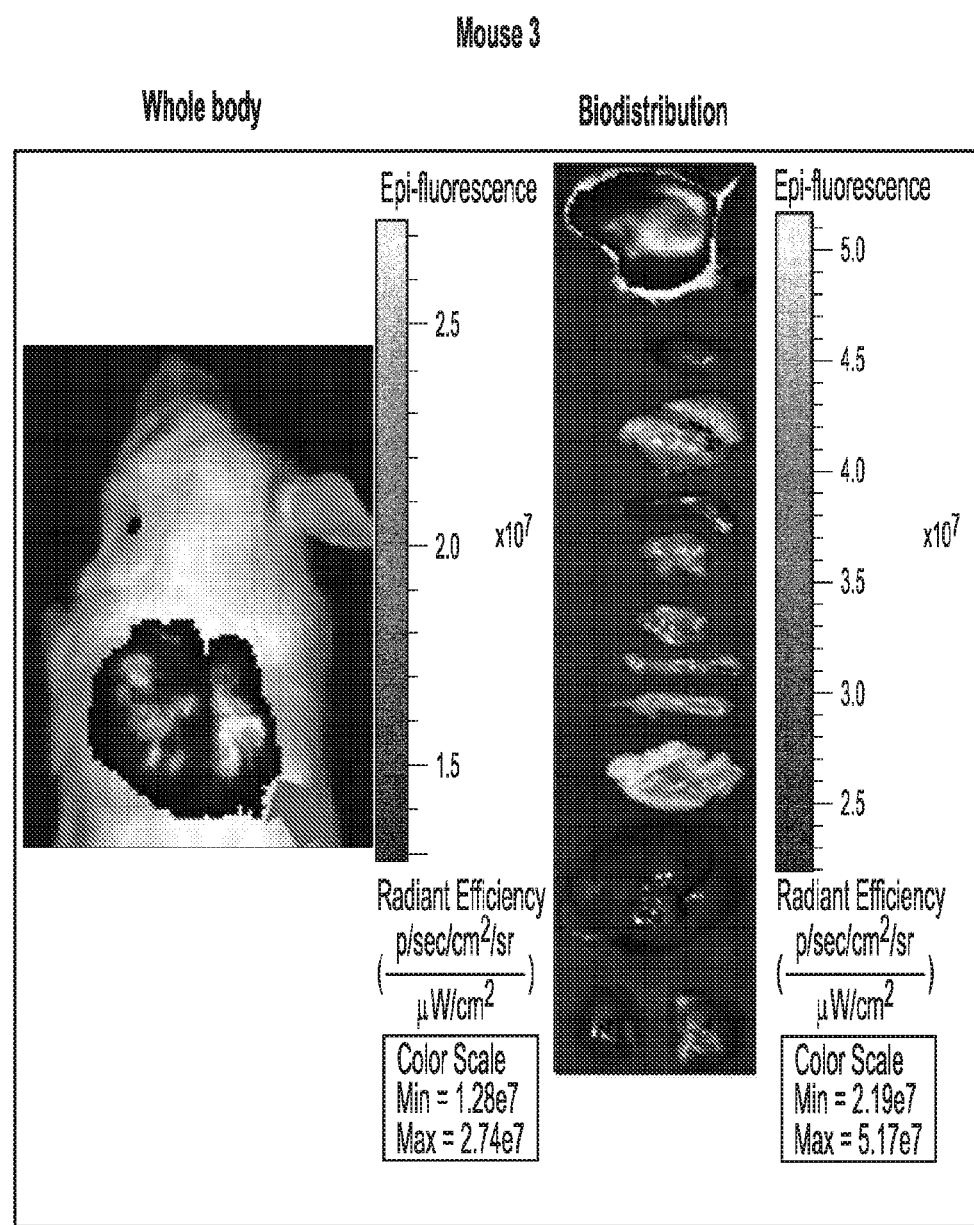

MDA-MB-231 xenograft was exploited to investigate the in vivo imaging ability of FAP targeted NIR conjugate consisting of PEG and peptidoglycan linker, JFL-L2-S0456, as shown in FIGS. 22A-C. Whole body imaging revealed that after 2 h post-injection the conjugate was found to be accumulated in the tumor. Biodistribution of vital organs/tissue further confirmed that tumor had the highest uptake of the dye conjugate. Followed by tumor the other two organs that displayed the uptake of JFL-L2-S0456 were liver and kidneys. The uptake in kidney was higher when compared to the liver. Kidney and liver plays a vital role in excretion of small molecules. The data suggests that the uptake of the FAP targeted dye conjugate in these organs was due to excretion of the fluorescent conjugate via renal and hepatic routes. No uptake was observed in any other organs.

Figure 23:
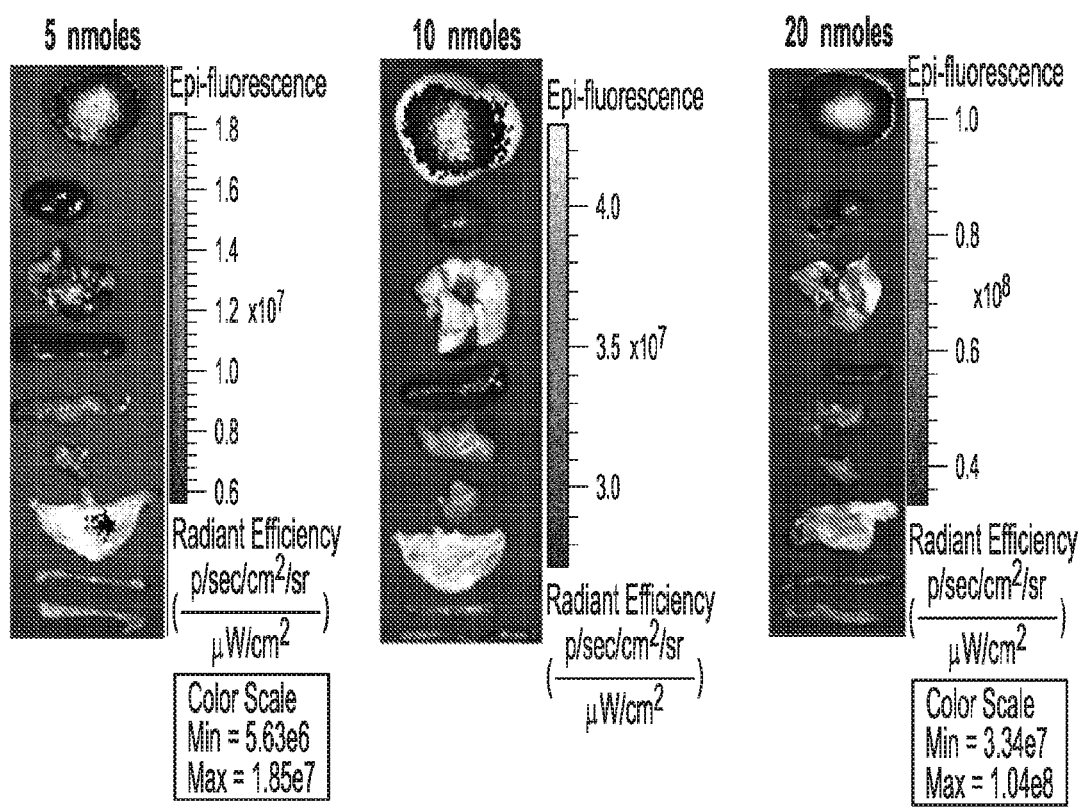
FIG. 23 shows in vivo imaging using different concentrations of JFL-L1-S0456.

In vivo imaging using different concentrations of JFL-L1-S0456: MDA-MB-231 tumor bearing female athymic nude mice were intravenously injected with 5, 10 or 20 nmoles of JFL-L1-S0456. After 2 h the mice were euthanized using $CO_2$ and imaged with IVIS Lumina II. After completing the whole-body imaging biodistribution was performed and the organs were imaged to examine the accumulation of JFL-L1-S0456, as shown in FIG. 23.

To investigate the uptake of JFL-L1-S0456 in a dose dependent manner MDA-MB-231 tumor xenografts were administered with the 5, 10 and 20 nmoles of the dye conjugate. A direct correlation between increasing dose and increase in fluorescence intensity of the tumor was observed. When compared to the mice in 5 nmole group a two-fold increase in the fluorescence intensity of tumor was observed in 10 nmole group. The fluorescence intensity of the tumor in 5 and 10 nmole group were found to be in $10^7$ range whereas the uptake in 20 nmole group was in $10^8$. Thus, the fluorescence intensity of the tumor was found to be increased with administration of higher dose of JFL-L1-S0456 and did not show any signs of saturation up to 20 nmoles.

Cocktail Imaging: FAPα and LHRH-R Targeted NIR Conjugates

Figure 24A:
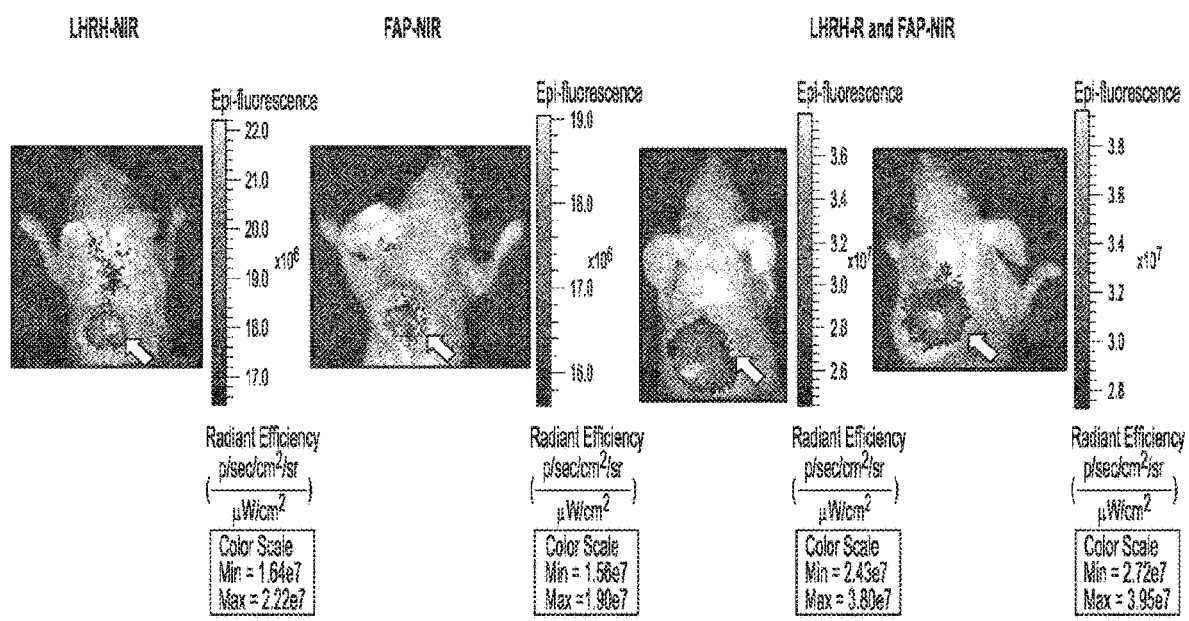
FIGS. 24A-B show Cocktail Imaging: FAPα and LHRH-R targeted NIR conjugates.
Figure 24B:
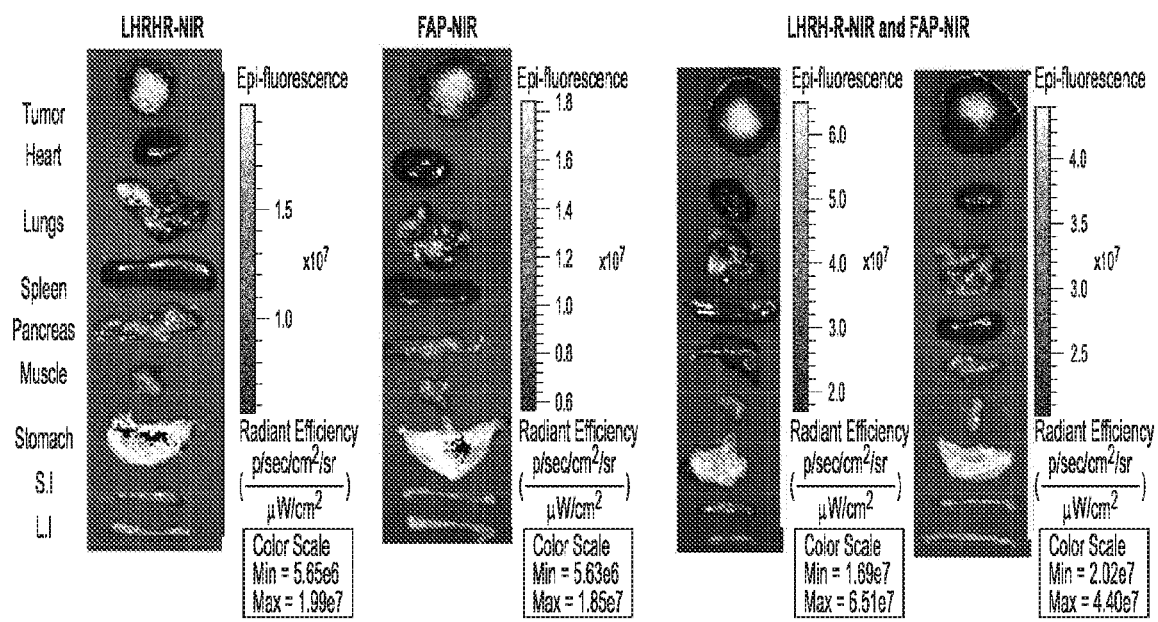

Female athymic mice were implanted with MDA-MB-231 cancer cells to develop subcutaneous tumors. Tumor bearing mice were intravenously injected either with FAP targeted NIR conjugate, JFL-L1-S0456 alone (5 nmoles) or Luteinizing hormone-releasing hormone receptor targeted NIR conjugate, JL-L3-S0456 (5 nmoles) alone or with both the conjugates. 2 h post-injection the mice were euthanized using $CO_2$ and imaged with Caliper IVIS Lumina II, as shown in FIG. 24A. Followed by completion of whole body imaging biodistribution was performed and all the organs were imaged to examine the uptake of the dye conjugates, as shown in FIG. 24B.

The feasibility of using FAP-targeted NIR dye (JFL-L1-S0456) and Luteinizing hormone-releasing receptor (LHRH-R) targeted NIR dye (JL-L3-S0456) to image cancers expressing both FAP and LHRH-R was evaluated. When injected with JFL-L1-S0456 or JL-L3-S0456 alone the uptake of the dye conjugates in MDA-MB-231 tumor was found to be in the similar intensity range. When the same tumor type was co-administered with the identical dose of JFL-L1-S0456 and JL-L3-S0456 an increase in the fluorescence intensity of the tumor was observed. When compared to the single agent group (JFL-L1-S0456 or JL-L3-S0456 alone) the increase of the intensity in the combination group was more than double. The results suggests that cocktail imaging by combining FAP and LHRH-R targeted imaging agents can be efficiently used to provide better image of the tumors that are positive for both the targets.

Figure 26:
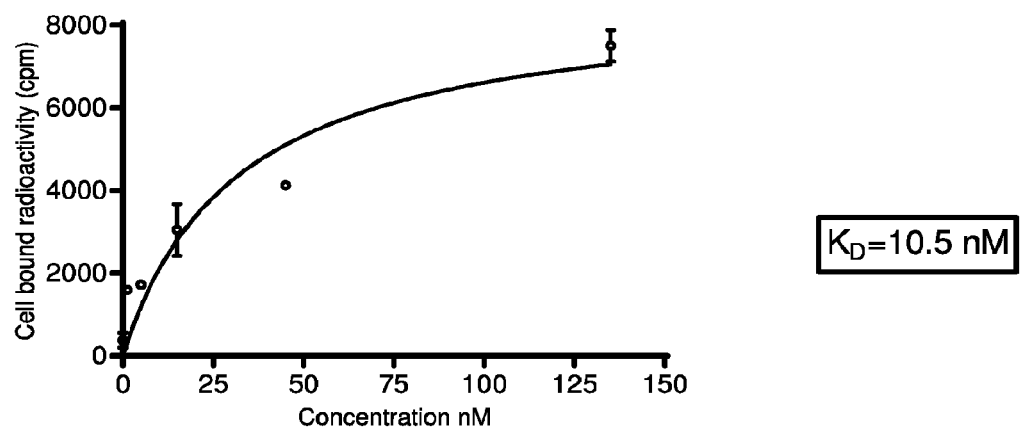
FIG. 26 shows in vitro binding affinity of JFL-L3.

In vitro binding study using $^{99m}$Tc labeled JFL-L3: Human FAPα transfected HEK-293 cells were seeded in amine coated 24 well plated and allowed to grow as monolayer. The spent medium was replaced with medium containing various concentrations of the $^{99m}$Tc labeled FAP conjugate (JFL-L3). For the blocking study, the cells were treated with $^{99m}$Tc labeled JFL-L3 in the presence of excess of JFL. After incubating for 2 h the cells were washed three times with culture medium to remove the unbound radioactive conjugate and dissolved in 0.5 ml of 0.25 N NaOH. Cell bound radioactivity was counted using gamma scintillation counter. The apparent $K_D$ was determined by analyzing the data using Graph Pad Prism and is shown in FIG. 26.

Figure 27A:
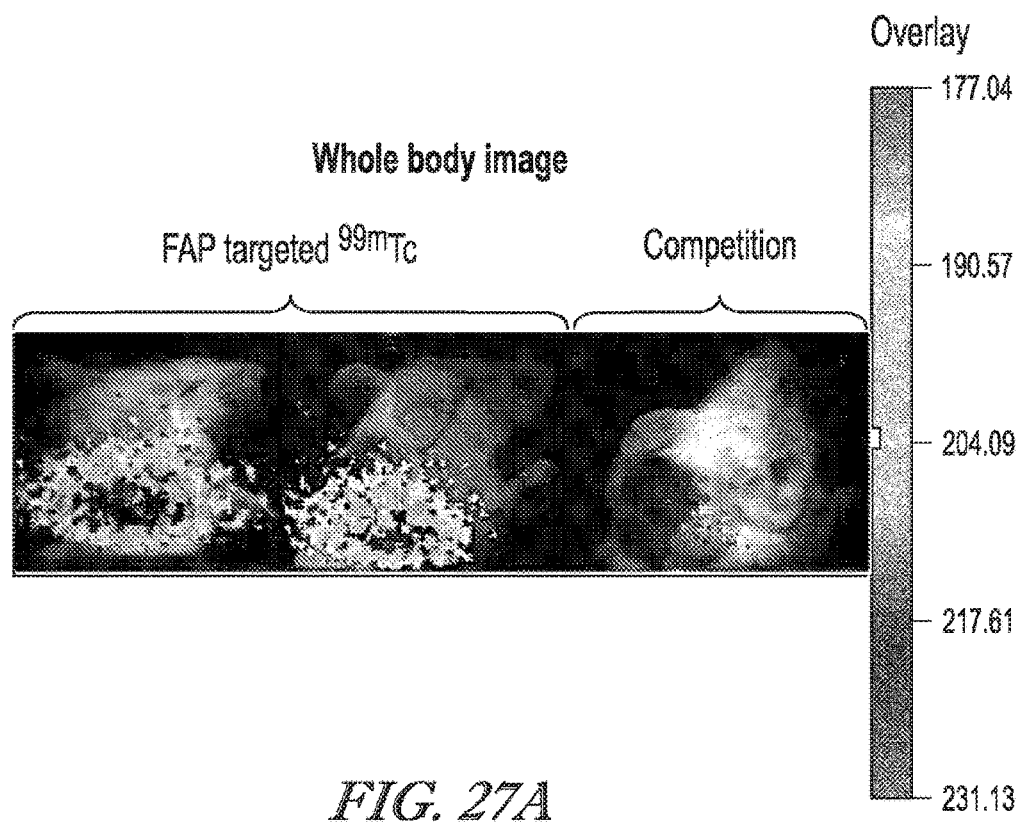
FIGS. 27A-C show in vivo imaging of JFL-L3

In vivo radioactive imaging: MDA-MB-231 tumor bearing athymic nude mice (female) were intravenously injected with 150 μCi of $^{99m}$Tc labeled JFL-L3 alone or in the presence of 100-fold excess of JFL. After 2 h mice were sacrificed by $CO_2$ asphyxiation, and imaged with KODAK Image Station, as shown in FIG. 27A. The parameters used for radioimaging were: acquisition time=2 min, f-stop=4, focal plane=7, FOV=200, binning=4. For white light imaging, the parameters were: acquisition time=0.05 s, f-stop=11, focal plane=7, FOV=200, with no binning. For the biodistribution study necropsy was performed to collect the organs/blood/tissues. Radioactivity associated with all the organs/blood/tissues was counted by using gamma counter.

Figure 27B:
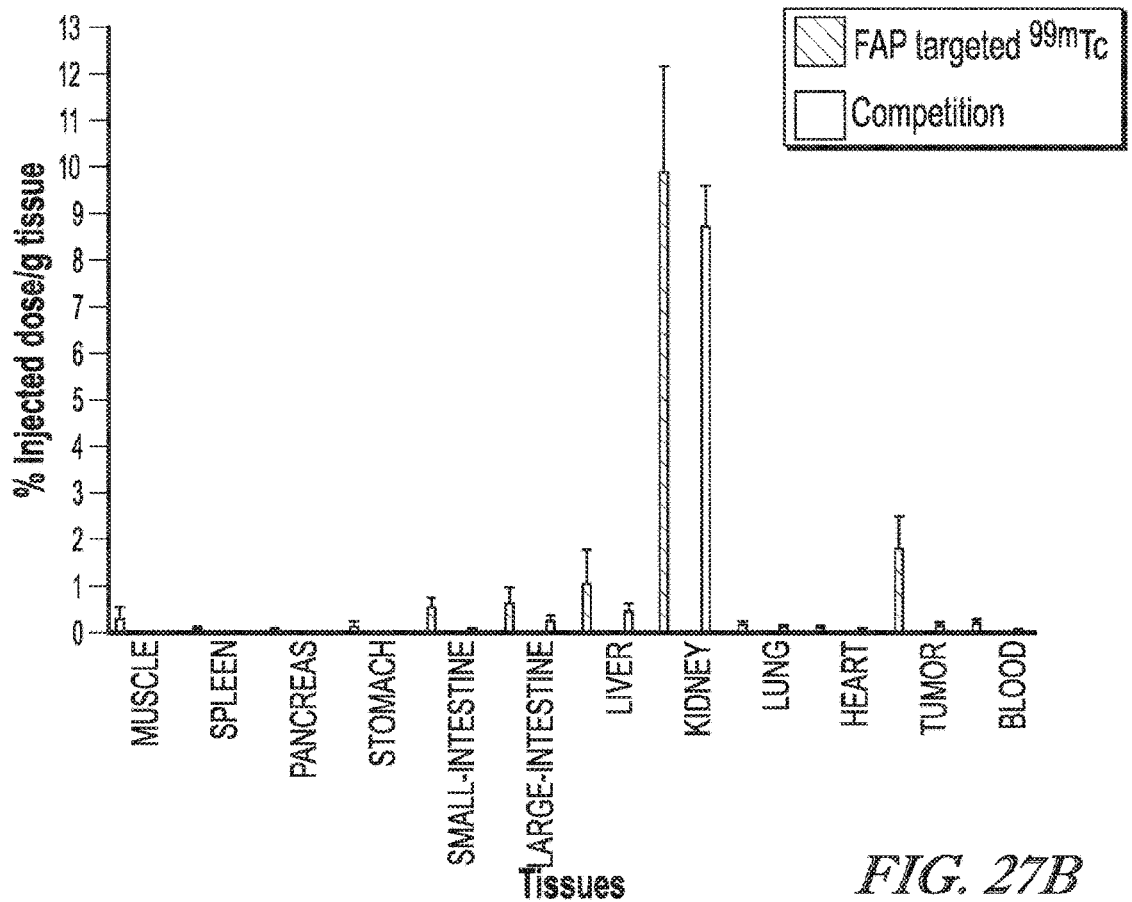
Figure 27C:
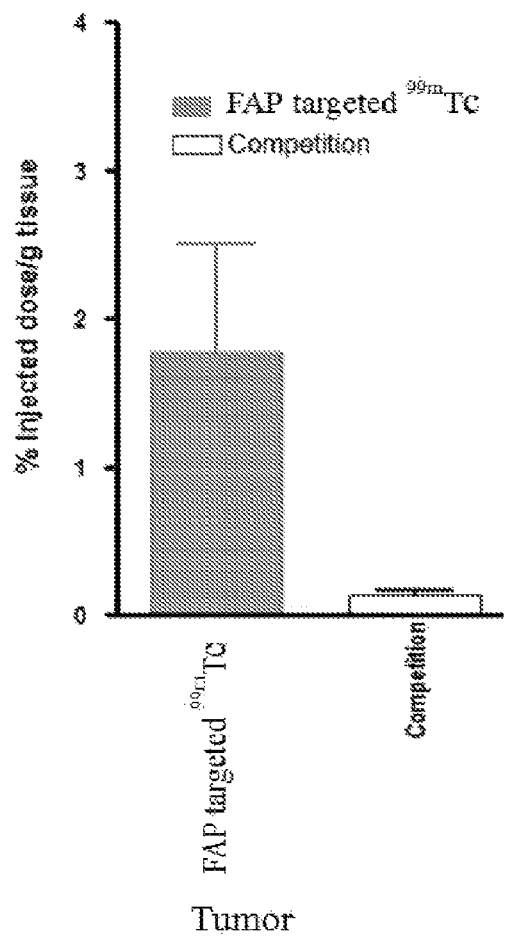

FAP targeted conjugate (JFL-L3) for $^{99m}$Tc radioactive imaging was synthesized by standard solid phase peptide synthesis. When tested in vitro in HEK cells-transfected with human FAP the $^{99m}$Tc labeled JFL-L3 displayed low nanomolar binding ($K_D$) of 10.5 nM. Following the in vitro study in vivo targeting of the $^{99m}$Tc labeled JFL-L3 was investigated in MDA-MB-231 tumor xenografts by administering the radiolabeled compound intravenously, as shown in FIG. 27B. FAP targeted radioactive conjugate was observed to accumulate in the tumor and kidney. Other than the tumor and kidney other organs displayed very low to no uptake of the radiolabeled compound. In the completion study excess of the JFL was found to block the tumor uptake of $^{99m}$Tc labeled JFL-L3 in the tumor indicating that the accumulation of the radiotracer in the tumor was FAP mediated. On the contrary the uptake in the kidney was not blocked by administration of excess of JFL, as shown in FIG. 27C. This suggested that the uptake of the radiotracer in the kidney is rather non-specific. Since small hydrophilic molecules are often excreted by renal route the uptake in the kidney might be transient. This data suggests that $^{99m}$Tc labeled JFL-L3 can accumulate in the tumor expressing FAP while causing minimal damage to the organs lacking the target antigen.

The entire contents of each and every patent publication, non-patent publication, and reference text cited herein are hereby incorporated by reference, except that in the event of any inconsistent disclosure or definition from the present specification, the disclosure or definition herein shall be deemed to prevail.

It is to be understood that use of the indefinite articles "a" and "an" in reference to an element does not exclude the presence, in some embodiments, of a plurality of such elements.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

What is claimed is:

1. A conjugate, or a pharmaceutically acceptable salt thereof, having a structure

B-L-X, wherein B is a fibroblast activation protein (FAP) inhibitor; is of the formula:

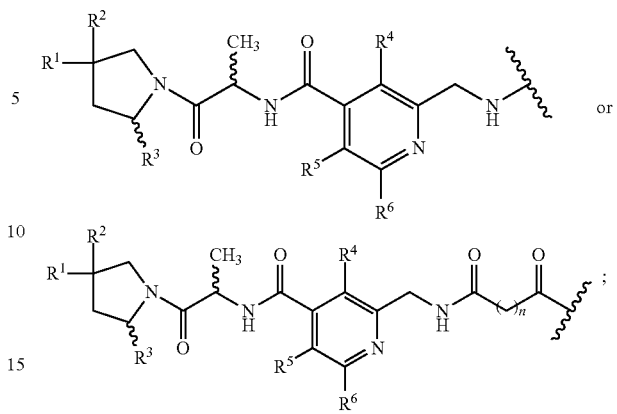

wherein each of $R^1$ and $R^2$ is independently selected from the group consisting of hydrogen, halogen, and $C_1$-$C_4$ alkyl; $R^3$ is a $C_1$-$C_4$ alkyl, nitrile, or isonitrile;

and each of $R^4$, $R^5$, and $R^6$ is independently selected from the group consisting of hydrogen, halogen, and $C_1$-$C_4$ alkyl; and n is an integer from 1 to 8

L is a bivalent linker comprising at least one amino acid selected from the group consisting of Glu and Cys, or a derivative thereof; and X comprises a near infrared (NIR) dye, a radioactive imaging agent, or a therapeutic agent effective against cancer cells and/or cancer-associated fibroblasts (CAF), wherein the linker further comprises a fragment of the formula

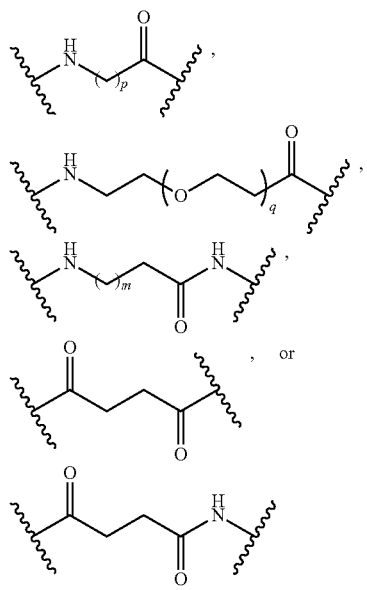

wherein m is an integer from 0 to 9;

p is an integer from 3 to 10; and q is an integer from 3 to 100.

2. The conjugate of claim 1, or a pharmaceutically acceptable salt thereof, wherein B is of the formula

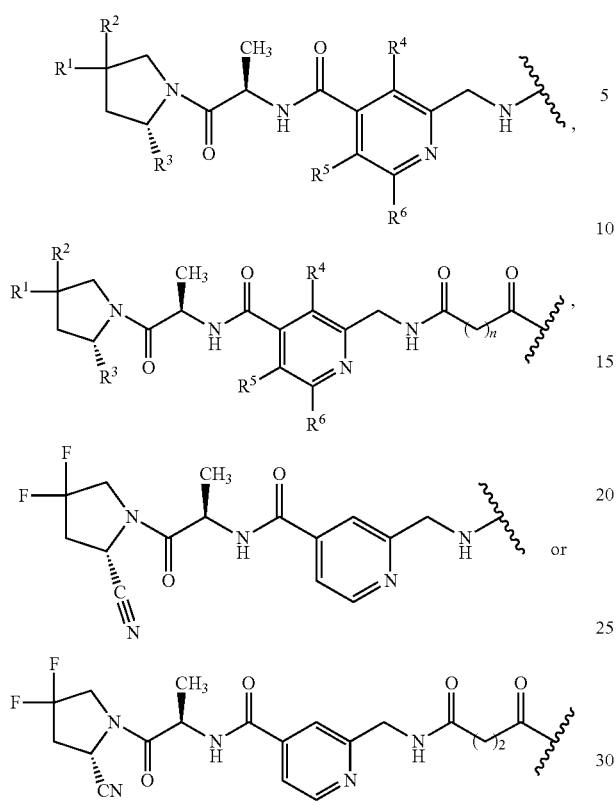

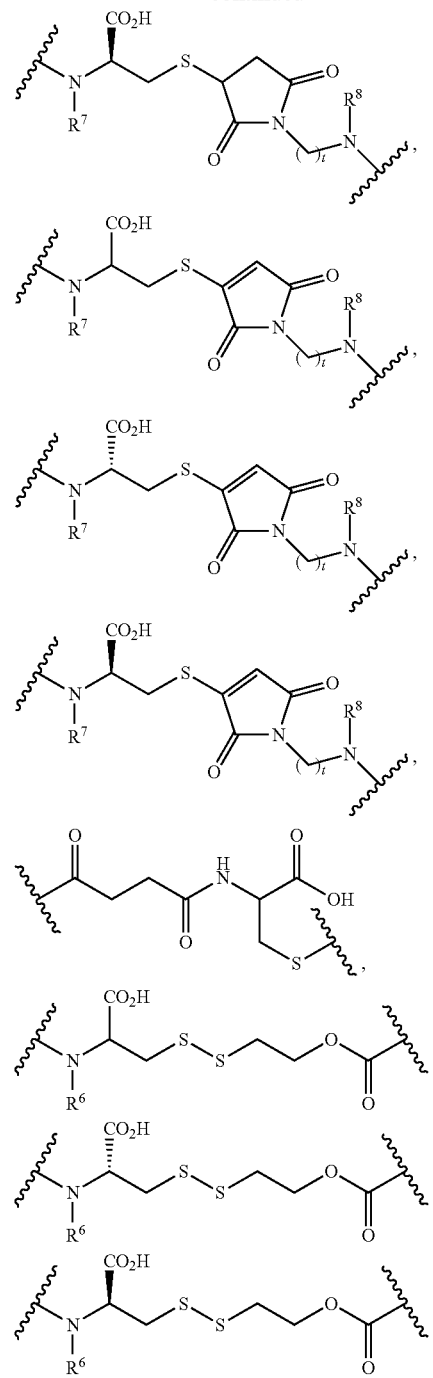

wherein
- each of $R^1$ and $R^2$ is independently selected from the group consisting of hydrogen, halogen, and $C_1$-$C_4$ alkyl;
- $R^3$ is a $C_1$-$C_4$ alkyl, nitrile, or isonitrile; and
- each of $R^4$, $R^5$, and $R^6$ is independently selected from the group consisting of hydrogen, halogen, and $C_1$-$C_4$ alkyl; and
- n is an integer from 1 to 8.

3. The conjugate of claim 1, or a pharmaceutically acceptable salt thereof, wherein the linker comprises a fragment of the formula

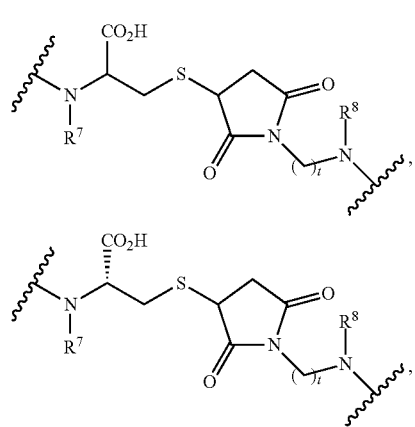

wherein
- $R^6$ is H or $C_1$-$C_6$ alkyl;
- each of $R^7$ and $R^8$ is independently H or $C_1$-$C_6$ alkyl; and
- t is an integer from 1 to 8.

4. A conjugate, or a pharmaceutically acceptable salt thereof, having a structure

B-L-X, wherein B is a fibroblast activation protein (FAP) inhibitor; is of the formula:

73

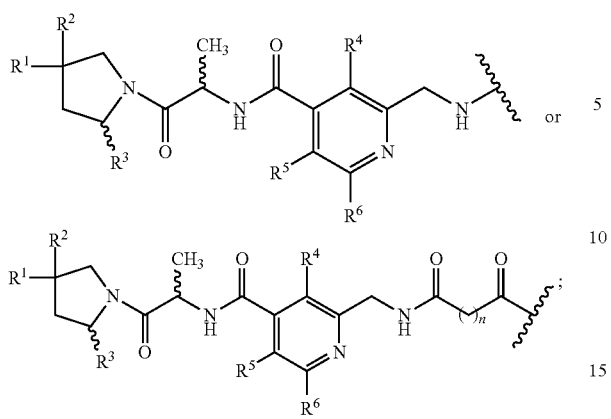

74 wherein each of $R^1$ and $R^2$ is independently selected from the group consisting of hydrogen, halogen, and $C_1$-$C_4$ alkyl; $R^3$ is a $C_1$-$C_4$ alkyl, nitrile, or isonitrile;

and each of $R^4$, $R^5$, and $R^6$ is independently selected from the group consisting of hydrogen, halogen, and $C_1$-$C_4$ alkyl; and n is an integer from 1 to 8

L is a bivalent linker comprising at least one amino acid selected from the group consisting of Glu and Cys, or a derivative thereof; and wherein X comprises fluorescein maleimide, fluorescein isothiocyanate (FITC), NIR dye S0456, or has a structure selected from the group consisting of

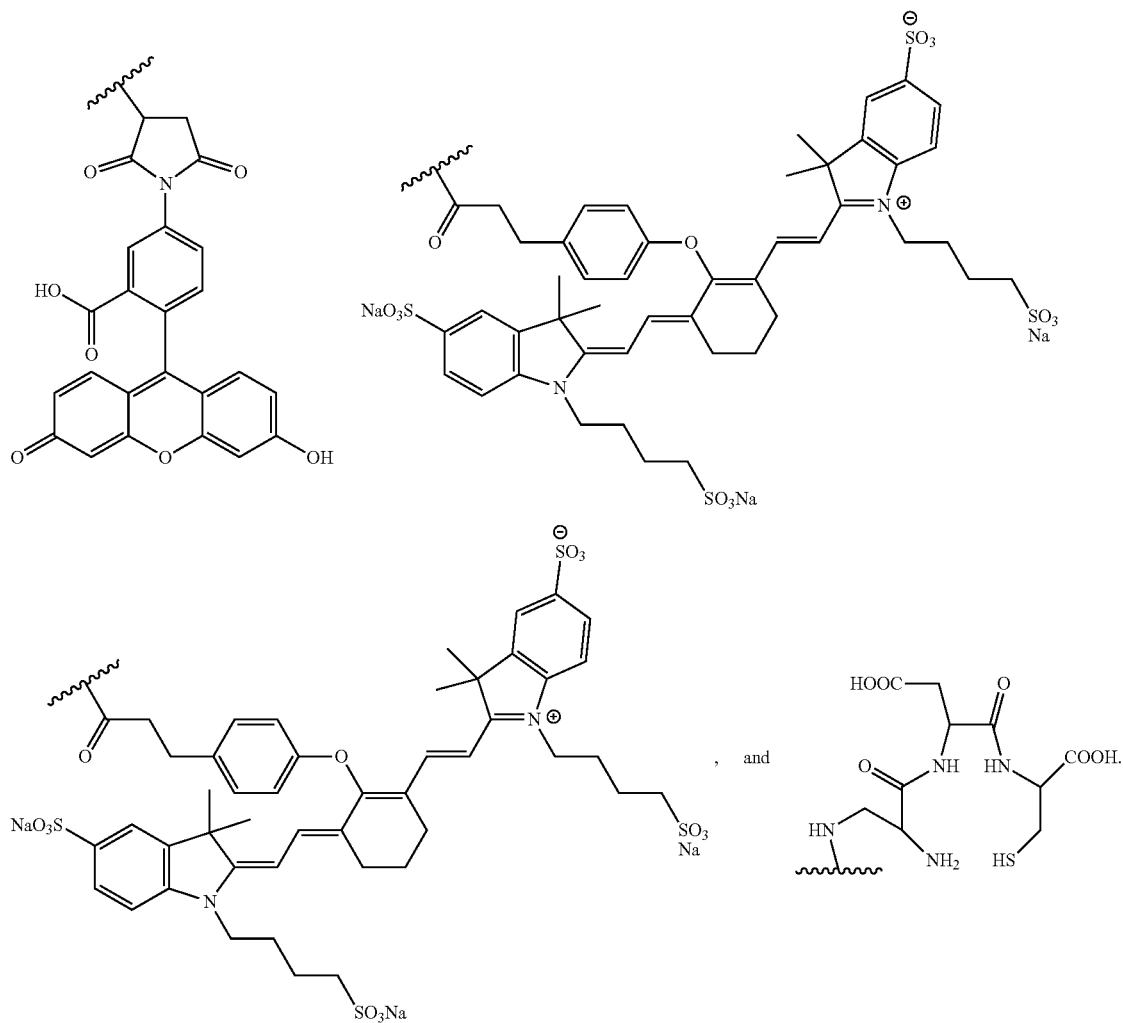

5. The conjugate of claim 1, or a pharmaceutically acceptable salt thereof, wherein X is a tetrapeptide of the formula

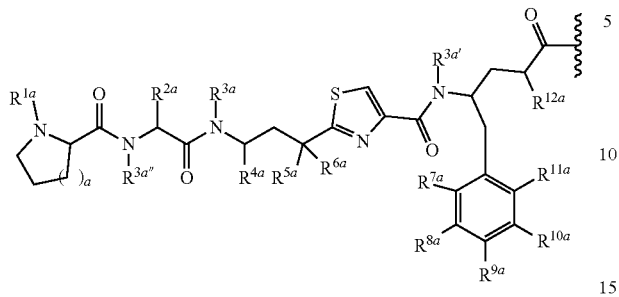

wherein
$R^{1a}$, $R^{3a}$, $R^{3a'}$ and $R^{3a''}$ are each independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{13a}$, —$OC(O)R^{13a}$, —$OC(O)NR^{13a}R^{13a'}$, —$OS(O)R^{13a}$, —$OS(O)_2R^{13a}$, —$SR^{13a}$, —$SC(O)R^{13a}$, —$S(O)R^{13a}$, —$S(O)_2R^{13a}$, —$S(O)_2OR^{13a}$, —$S(O)NR^{13a}R^{13a'}$, —$S(O)_2NR^{13a}R^{13a'}$, —$OS(O)NR^{13a}R^{13a'}$, —$OS(O)_2NR^{13a}R^{13a'}$, —$NR^{13a}R^{13a'}$, —$NR^{13a}C(O)R^{14a}$, —$NR^{13a}C(O)OR^{14a}$, —$NR^{13a}C(O)NR^{14a}R^{14a'}$, —$NR^{13a}S(O)R^{14a}$, —$NR^{13a}S(O)_2R^{14a}$, —$NR^{13a}S(O)NR^{14a}R^{14a'}$, —$NR^{13a}S(O)_2NR^{14a}R^{14a'}$, —$P(O)(OR^{13a})_2$, —$C(O)R^{13a}$, —$C(O)OR^{13a}$ or —$C(O)NR^{13a}R^{13a'}$;

$R^{2a}$, $R^{4a}$ and $R^{12a}$ are each independently selected from the group consisting of H, $C_1$-$C_6$ alkyl, $C_2$-$C_6$ alkenyl, $C_2$-$C_6$ alkynyl;

$R^{5a}$ and $R^{6a}$ are each independently selected from the group consisting of H, halogen, $C_1$-$C_6$ alkyl, $C_2$-$C_6$ alkenyl, $C_2$-$C_6$ alkynyl, —$OR^{15a}$, —$SR^{15a}$ and —$NR^{15a}R^{15a'}$, wherein each hydrogen atom in $C_1$-$C_6$ alkyl, $C_2$-$C_6$ alkenyl and $C_2$-$C_6$ alkynyl is independently optionally substituted by halogen, —$OR^{16a}$, —$SR^{16a}$, —$NR^{16a}R^{16a'}$, —$C(O)R^{16a}$, —$C(O)OR^{16a}$ or —$C(O)NR^{16a}R^{16a'}$; or $R^{5a}$ and $R^{6a}$ taken together with the carbon atom to which they are attached form a —$C(O)$—;

each $R^{7a}$, $R^{8a}$, $R^{9a}$, $R^{10a}$ and $R^{11a}$ is independently selected from the group consisting of H, halogen, $C_1$-$C_6$ alkyl, $C_2$-$C_6$ alkenyl, $C_2$-$C_6$ alkynyl, —CN, —$NO_2$, —NCO, —$OR^{17a}$, —$SR^{17a}$, —$S(O)_2OR^{17a}$, —$NR^{17a}R^{17a'}$, —$P(O)(OR^{17a})_2$, —$C(O)R^{17a}$, —$C(O)OR^{17a}$ and —$C(O)NR^{17a}R^{17a'}$, wherein each hydrogen atom in $C_1$-$C_6$ alkyl, $C_2$-$C_6$ alkenyl and $C_2$-$C_6$ alkynyl is independently optionally substituted by halogen, —$OR^{18a}$, —$SR^{18a}$, —$NR^{18a}R^{18a'}$, —$C(O)R^{18a}$, —$C(O)OR^{18a}$ or —$C(O)NR^{18a}R^{18a'}$;

each $R^{13a}$, $R^{13a'}$, $R^{14a}$, $R^{14a'}$, $R^{15a}$, $R^{15a'}$, $R^{16a}$, $R^{16a'}$, $R^{17a}$ and $R^{17a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, —OH, —SH, —$NH_2$ or —$CO_2H$;

each $R^{18a}$ and $R^{18a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl —$C(O)R^{19a}$, —$P(O)(OR^{19a})_2$, and —$S(O)_2OR^{19a}$;

each $R^{19a}$ is independently selected from H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl; and a is 1, 2 or 3.

6. The conjugate of claim 1, or a pharmaceutically acceptable salt thereof, wherein B-L comprises a fragment of the formula

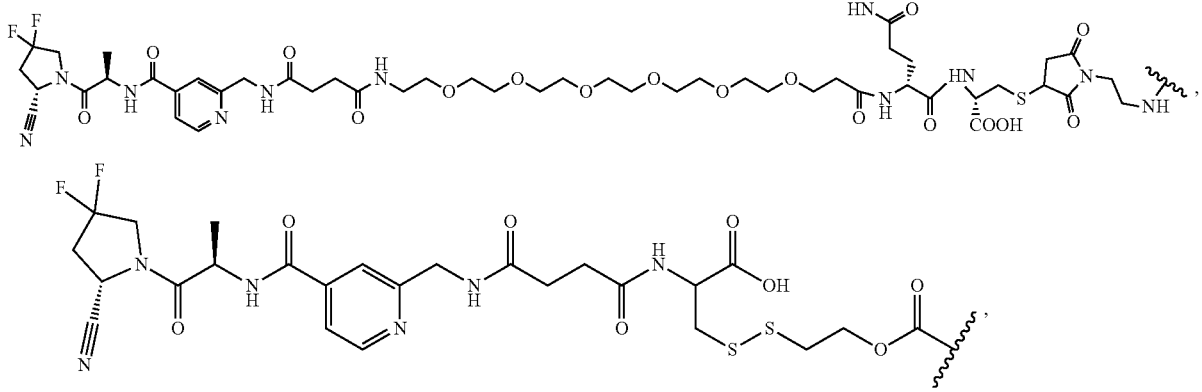

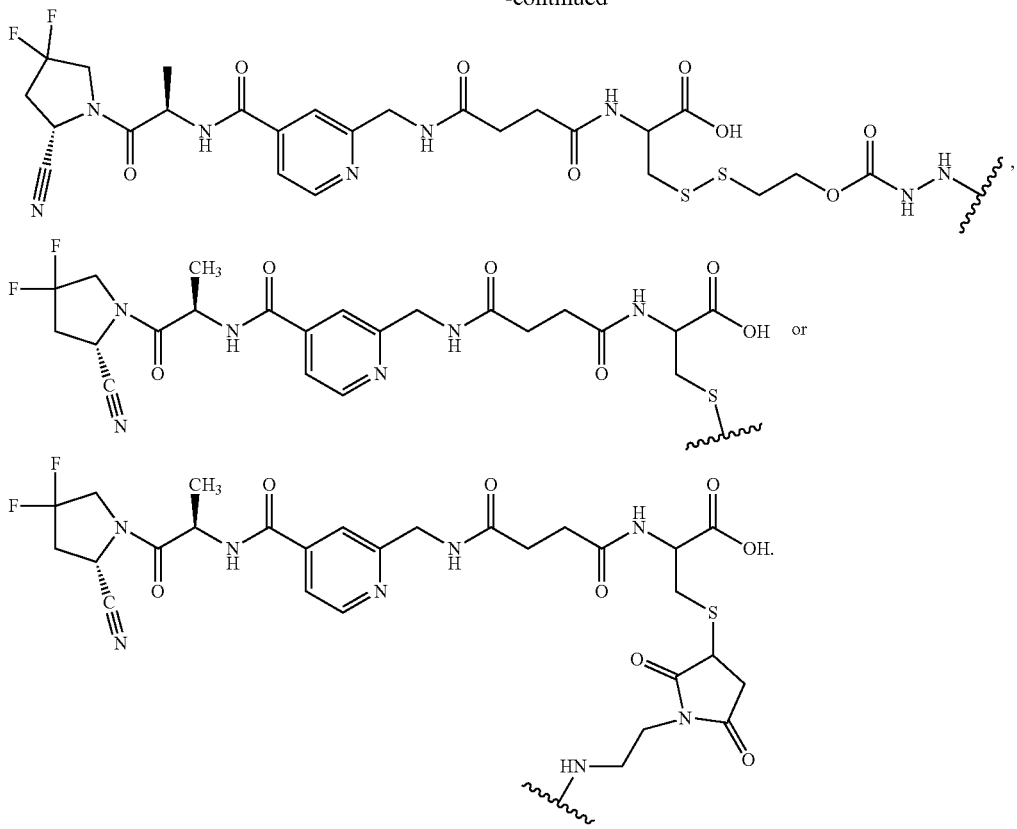

7. A conjugate, or a pharmaceutically acceptable salt thereof, having a structure:

B-L-X, wherein B is of the formula

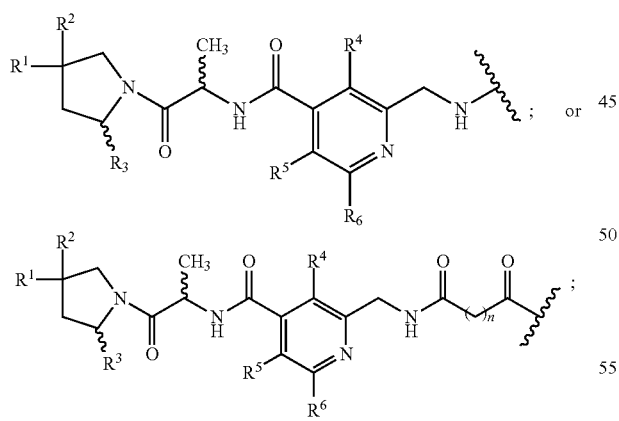

wherein
each of $R^1$ and $R^2$ in independently selected from the group consisting of hydrogen, halogen, and $C_1$-$C_4$ alkyl;
$R^3$ is a $C_1$-$C_4$ alkyl, nitrile, or isonitrile;
each of $R^4$, $R^5$, and $R^6$ is independently selected from the group consisting of hydrogen, halogen, and $C_1$-$C_4$ alkyl;
n is an integer from 1 to 8;
L is a bivalent linker; and
X comprises a near infrared (NIR) dye, a radioactive imaging agent, or a therapeutic agent effective against cancer cells and/or cancer-associated fibroblasts (CAF).

8. The conjugate of claim 7, or a pharmaceutically acceptable salt thereof, wherein B is of the formula

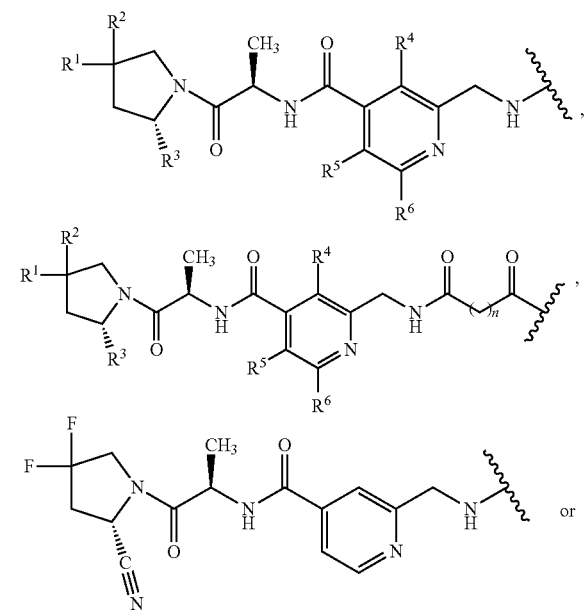

-continued

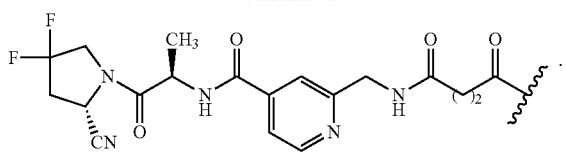

9. The conjugate of claim 7, or a pharmaceutically acceptable salt thereof, wherein the linker further comprises a fragment of the formula

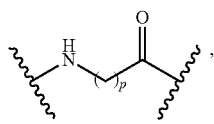

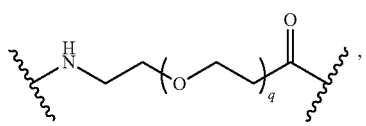

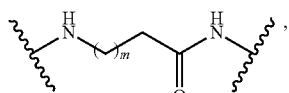

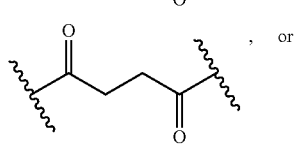

, or

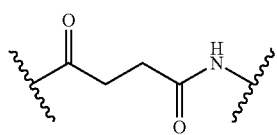

wherein
m is an integer from 0 to 9;
p is an integer from 3 to 10; and
q is an integer from 3 to 100.

10. The conjugate of claim 7, or a pharmaceutically acceptable salt thereof, wherein the linker comprises a fragment of the formula

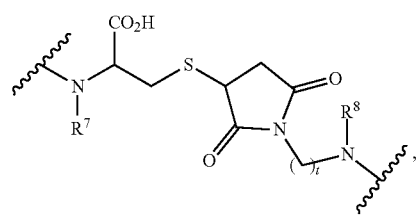

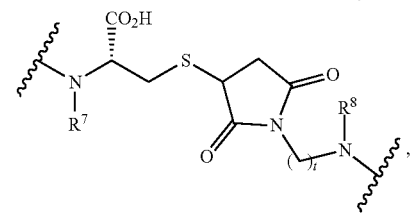

-continued

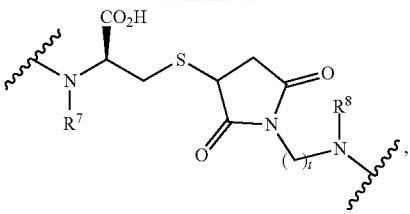

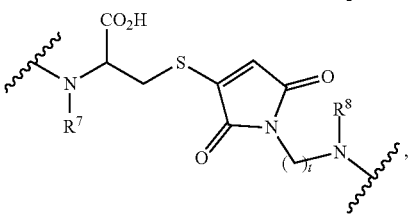

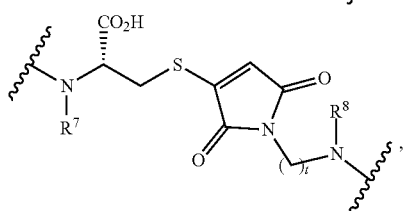

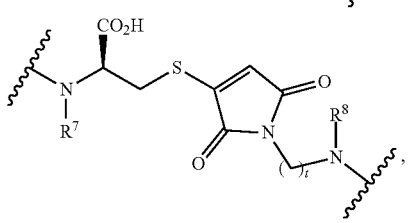

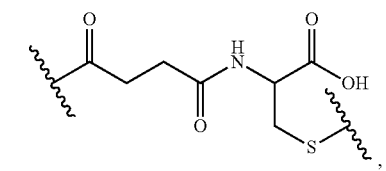

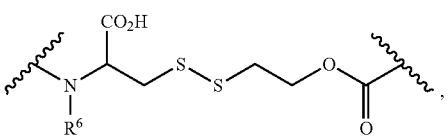

or

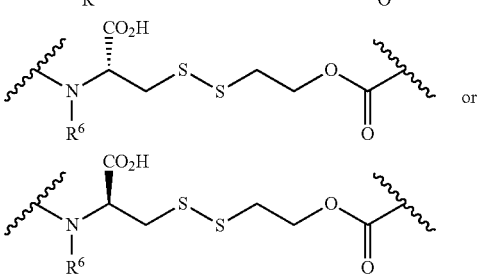

wherein
$R^6$ is H or $C_1$-$C_6$ alkyl;
each of $R^7$ and $R^8$ is independently H or $C_1$-$C_6$ alkyl; and
t is an integer from 1 to 8.

11. The conjugate of claim 7, or a pharmaceutically acceptable salt thereof, wherein X comprises fluorescein maleimide, fluorescein isothiocyanate (FITC), NIR dye S0456, or has a structure selected from the group consisting of

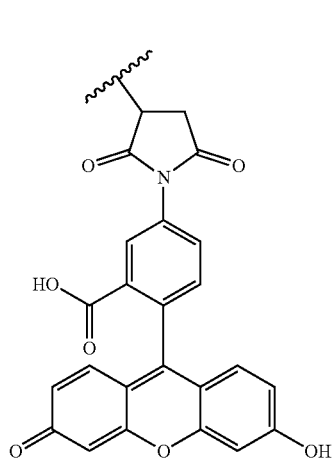
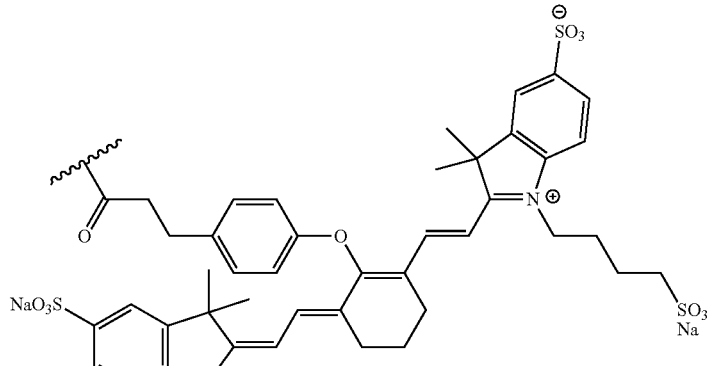
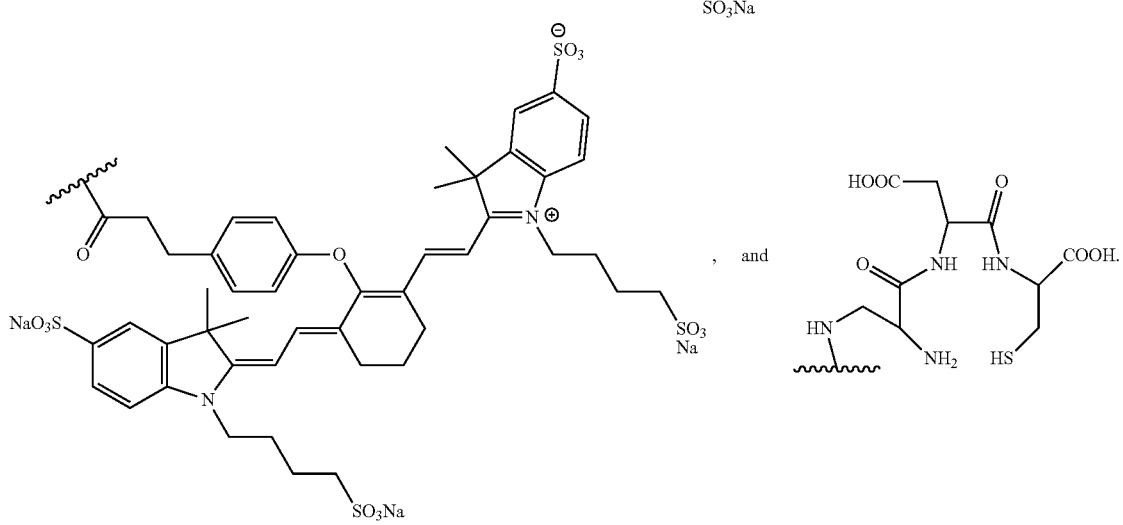
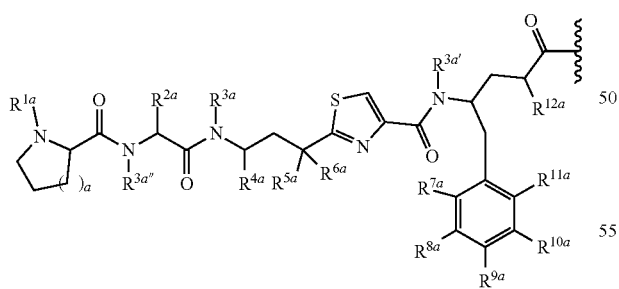

12. The conjugate of claim 7, or a pharmaceutically acceptable salt thereof, wherein X is a tetrapeptide of the formula wherein $R^{1a}$, $R^{3a}$, $R^{3a'}$ and $R^{3a''}$ are each independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{13a}$, —$OC(O)R^{13a}$, —$OC(O)NR^{13a}R^{13a'}$, —$OS(O)R^{13a}$, —$OS(O)_2R^{13a}$, —$SR^{13a}$, —$SC(O)R^{13a}$, —$S(O)R^{13a}$, —$S(O)_2R^{13a}$, —$S(O)_2OR^{13a}$, —$S(O)NR^{13a}R^{13a'}$, —$S(O)_2NR^{13a}R^{13a'}$, —$OS(O)NR^{13a}R^{13a'}$, —$OS(O)_2NR^{13a}R^{13a'}$, —$NR^{13a}R^{13a'}$, —$NR^{13a}C(O)R^{14a}$, —$NR^{13a}C(O)OR^{14a}$, —$NR^{13a}C(O)NR^{14a}R^{14a'}$, —$NR^{13a}S(O)R^{14a}$, —$NR^{13a}S(O)_2R^{14a}$, —$NR^{13a}S(O)NR^{13a}R^{14a'}$, —$NR^{13a}S(O)_2NR^{14a}R^{14a'}$, —$P(O)(OR^{13a})_2$, —$C(O)R^{13a}$, —$C(O)OR^{13a}$ or —$C(O)NR^{13a}R^{13a'}$;

$R^{2a}$, $R^{4a}$ and $R^{12a}$ are each independently selected from the group consisting of H, $C_1$-$C_6$ alkyl, $C_2$-$C_6$ alkenyl, $C_2$-$C_6$ alkynyl;

$R^{5a}$ and $R^{6a}$ are each independently selected from the group consisting of H, halogen, $C_1$-$C_6$ alkyl, $C_2$-$C_6$ alkenyl, $C_2$-$C_6$ alkynyl, —$OR^{15a}$, —$SR^{15a}$ and —$NR^{15a}R^{15a'}$, wherein each hydrogen atom in $C_1$-$C_6$ alkyl, $C_2$-$C_6$ alkenyl and $C_2$-$C_6$ alkynyl is independently optionally substituted by halogen, —$OR^{16a}$, —$SR^{16a}$, —$NR^{16a}R^{16a'}$, —$C(O)R^{16a}$, —$C(O)OR^{16a}$ or —$C(O)NR^{16a}R^{16a'}$; or $R^{5a}$ and $R^{6a}$ taken together with the carbon atom to which they are attached form a —$C(O)$—;

each $R^{7a}$, $R^{8a}$, $R^{9a}$, $R^{10a}$ and $R^{11a}$ is independently selected from the group consisting of H, halogen, $C_1$-$C_6$ alkyl, $C_2$-$C_6$ alkenyl, $C_2$-$C_6$ alkynyl, —CN, —NO$_2$, —NCO, —OR$^{17a}$, —SR$^{17a}$, —S(O)$_2$OR$^{17a}$, —NR$^{17a}$R$^{17a'}$, —P(O)(OR$^{17a}$)$_2$, —C(O)R$^{17a}$, —C(O)OR$^{17a}$ and —C(O)NR$^{17a}$R$^{17a'}$, wherein each hydrogen atom in $C_1$-$C_6$ alkyl, $C_2$-$C_6$ alkenyl and $C_2$-$C_6$ alkynyl is independently optionally substituted by halogen, —OR$^{18a}$, —SR$^{18a}$, —NR$^{18a}$R$^{18a'}$, —C(O)R$^{18a}$, —C(O)OR$^{18a}$ or —C(O)NR$^{18a}$R$^{18a'}$;

each R$^{13a}$, R$^{13a'}$, R$^{14a}$, R$^{14a'}$, R$^{15a}$, R$^{15a'}$, R$^{16a}$, R$^{16a'}$, R$^{17a}$ and R$^{17a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, —OH, —SH, —NH$_2$ or —CO$_2$H;

each R$^{18a}$ and R$^{18a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl —C(O)R$^{19a}$, —P(O)(OR$^{19a}$)$_2$, and —S(O)$_2$OR$^{19a}$, each R$^{19a}$ is independently selected from H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl; and a is 1, 2 or 3.

13. The conjugate of claim 7, or a pharmaceutically acceptable salt thereof, wherein B-L comprises a fragment of the formula

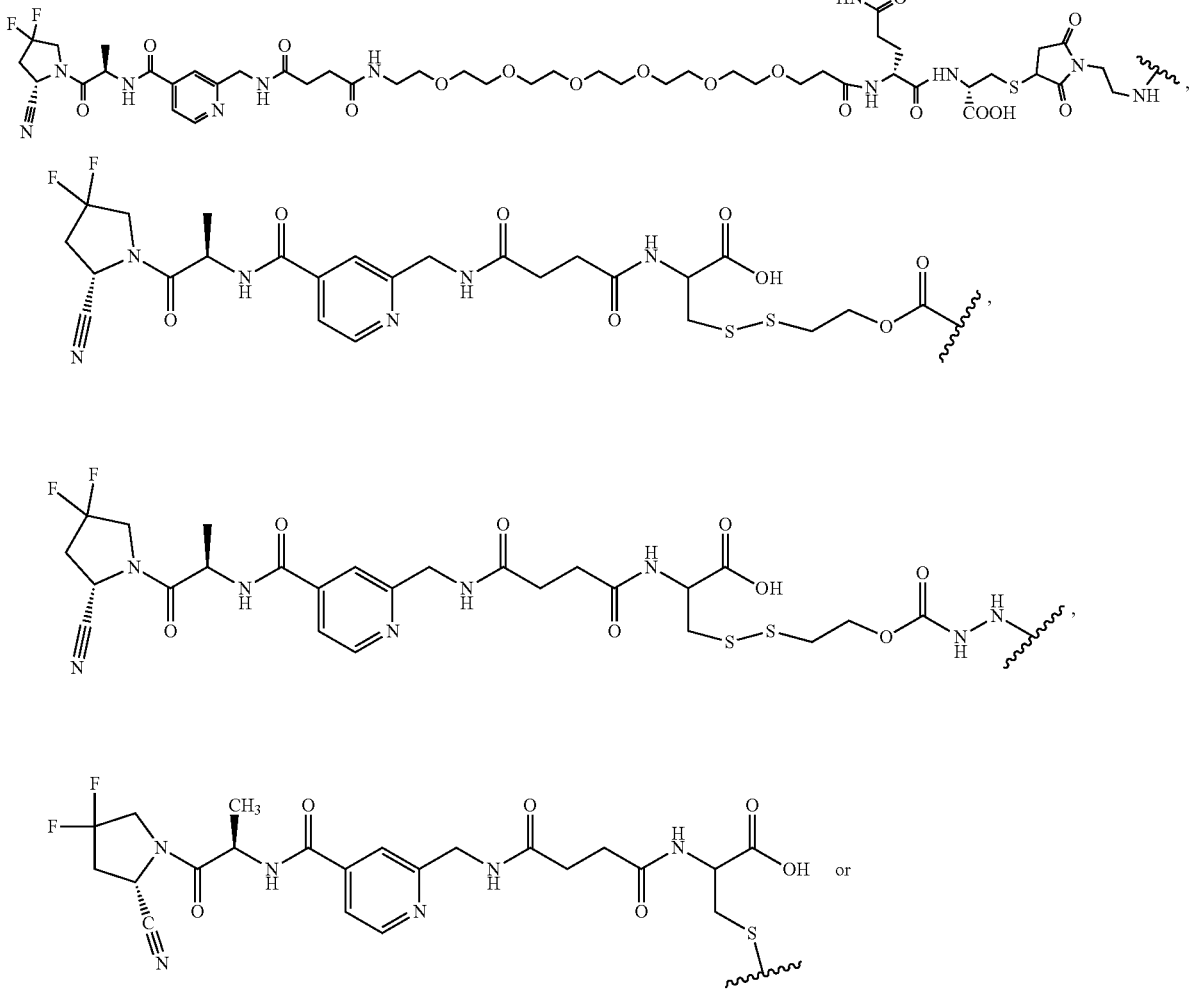

-continued

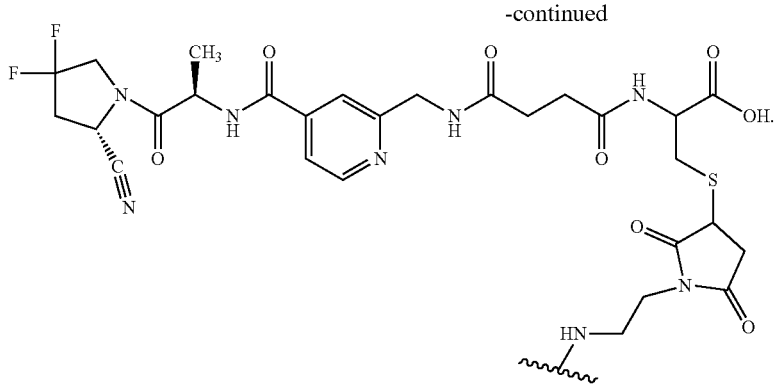

14. A pharmaceutical composition comprising a conjugate of claim 1, or a pharmaceutically acceptable salt thereof, and optionally at least one pharmaceutically acceptable excipient.

15. A method of treating cancer in a subject, comprising administering to the subject an effective amount of a conjugate of claim 1, or a pharmaceutically acceptable salt thereof.

16. A method of imaging a population of cells in vitro, comprising contacting the cells with a conjugate of claim 1, to provide labelled cells, and visualizing the labelled cells.

17. A method of imaging a population of cells in vivo, comprising administering to a patient an effective amount of a conjugate of claim 1, or a pharmaceutically acceptable salt thereof, to provide labelled cells; and visualizing the labelled cells.

18. A pharmaceutical composition comprising a conjugate of claim 7, or a pharmaceutically acceptable salt thereof, and optionally at least one pharmaceutically acceptable excipient.

19. A method of treating cancer in a subject, comprising administering to the subject an effective amount of a conjugate of claim 7, or a pharmaceutically acceptable salt thereof.

20. A method of imaging a population of cells in vitro, comprising contacting the cells with a conjugate of claim 7, to provide labelled cells, and visualizing the labelled cells.

21. A method of imaging a population of cells in vivo, comprising administering to a patient an effective amount of a conjugate of claim 7, or a pharmaceutically acceptable salt thereof, to provide labelled cells; and visualizing the labelled cells.

22. A method of imaging a population of cells, comprising contacting the cells with a conjugate of claim 4, to provide labelled cells, and visualizing the labelled cells.

* * * * *